(12) United States Patent
Anderson et al.

(10) Patent No.: US 11,590,020 B2
(45) Date of Patent: Feb. 28, 2023

(54) METHODS AND DEVICES FOR SELECTIVE DISRUPTION OF FATTY TISSUE BY CONTROLLED COOLING

(71) Applicant: The General Hospital Corporation, Boston, MA (US)

(72) Inventors: Richard R. Anderson, Boston, MA (US); Dieter Manstein, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 50 days.

(21) Appl. No.: 14/493,333

(22) Filed: Sep. 22, 2014

(65) Prior Publication Data
US 2015/0112412 A1 Apr. 23, 2015

Related U.S. Application Data

(63) Continuation of application No. 11/016,196, filed on Dec. 17, 2004, now Pat. No. 8,840,608, which is a
(Continued)

(51) Int. Cl.
*A61B 18/02* (2006.01)
*A61F 7/00* (2006.01)
*A61B 5/00* (2006.01)
*A61F 7/10* (2006.01)
*A61B 8/08* (2006.01)
(Continued)

(52) U.S. Cl.
CPC .............. *A61F 7/00* (2013.01); *A61B 5/6804* (2013.01); *A61B 8/485* (2013.01); *A61B 18/02* (2013.01); *A61F 7/10* (2013.01); *A61B 2017/00084* (2013.01); *A61B 2090/378* (2016.02); *A61F 2007/0001* (2013.01);
(Continued)

(58) Field of Classification Search
CPC .......... A61B 18/02; A61B 2018/00791; A61B 2018/025; A61B 2018/00464; A61B 2018/0262; A61B 2018/0268; A61B 2018/0237; A61F 2007/0056; A61F 2007/029
See application file for complete search history.

(56) References Cited

U.S. PATENT DOCUMENTS 3,093,135 A 6/1963 Hirschhorn et al.
3,502,080 A 3/1970 Hirschhorn
(Continued)

FOREIGN PATENT DOCUMENTS

CH 333982 12/1958
DE 532976 5/1974
(Continued)

OTHER PUBLICATIONS

Examiner's First Report, Australian Patent Application No. 2005316277 (Mar. 11, 2010).
(Continued)

*Primary Examiner* — Michael Peffley

(57) ABSTRACT

The present invention relates to methods for use in the selective disruption of lipid-rich cells by controlled cooling. The present invention further relates to a device for use in carrying out the methods for selective disruption of lipid-rich cells by controlled cooling.

4 Claims, 35 Drawing Sheets

Related U.S. Application Data continuation-in-part of application No. 10/391,221, filed on Mar. 17, 2003, now Pat. No. 7,367,341.

(60) Provisional application No. 60/365,662, filed on Mar. 15, 2002.

(51) Int. Cl.
 A61B 17/00 (2006.01)
 A61F 7/02 (2006.01)
 A61B 90/00 (2016.01)

(52) U.S. Cl.
 CPC ............... *A61F 2007/0056* (2013.01); *A61F 2007/0094* (2013.01); *A61F 2007/029* (2013.01)

(56) References Cited

U.S. PATENT DOCUMENTS

| | | |
|---|---|---|
| 3,942,519 A | 3/1976 | Shock et al. |
| 3,986,385 A | 10/1976 | Johnston et al. |
| 4,026,299 A | 5/1977 | Sauder |
| 4,202,336 A | 5/1980 | Man et al. |
| 4,381,009 A | 4/1983 | Del et al. |
| 4,483,341 A | 11/1984 | Witteles |
| 4,528,979 A | 7/1985 | Marchenko et al. |
| 4,531,524 A | 7/1985 | Mioduski |
| 4,566,455 A | 1/1986 | Kramer |
| 4,585,002 A | 4/1986 | Kissin et al. |
| 4,614,191 A | 9/1986 | Perler |
| 4,644,955 A | 2/1987 | Mioduski |
| 4,700,701 A | 10/1987 | Montaldi et al. |
| 4,718,429 A | 1/1988 | Smidt et al. |
| 4,741,338 A | 5/1988 | Miyamae et al. |
| 4,802,475 A | 2/1989 | Weshahy et al. |
| 4,832,022 A | 5/1989 | Tjulkov et al. |
| 4,869,250 A | 9/1989 | Bitterly |
| 4,905,697 A | 3/1990 | Heggs et al. |
| 4,961,422 A | 10/1990 | Marchosky et al. |
| 4,979,502 A | 12/1990 | Hunt |
| 5,007,433 A | 4/1991 | Hermsdoerffer et al. |
| 5,018,521 A | 5/1991 | Campbell |
| 5,024,650 A | 6/1991 | Hagiwara et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner et al. |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton et al. |
| 5,241,951 A | 9/1993 | Mason et al. |
| 5,269,369 A | 12/1993 | Faghri |
| 5,277,030 A | 1/1994 | Miller |
| 5,327,886 A | 7/1994 | Chiu |
| 5,330,745 A | 7/1994 | Mcdow |
| 5,339,541 A | 8/1994 | Owens |
| 5,351,677 A | 10/1994 | Kami et al. |
| 5,358,467 A | 10/1994 | Milstein et al. |
| 5,372,608 A | 12/1994 | Johnson |
| 5,411,541 A | 5/1995 | Bell et al. |
| 5,486,207 A | 1/1996 | Mahawili et al. |
| 5,507,790 A | 4/1996 | Weiss et al. |
| 5,507,792 A | 4/1996 | Mason et al. |
| 5,531,742 A | 7/1996 | Barken et al. |
| 5,575,812 A | 11/1996 | Owens |
| 5,628,769 A | 5/1997 | Saringer et al. |
| 5,634,940 A | 6/1997 | Panyard |
| 5,647,051 A | 7/1997 | Neer |
| 5,647,868 A | 7/1997 | Chinn et al. |
| 5,654,546 A | 8/1997 | Lindsay et al. |
| 5,660,836 A | 8/1997 | Knowlton |
| 5,665,053 A | 9/1997 | Jacobs et al. |
| 5,672,172 A | 9/1997 | Zupkas et al. |
| 5,700,284 A | 12/1997 | Owens |
| 5,725,483 A | 3/1998 | Podolsky |
| 5,733,280 A | 3/1998 | Witall |
| 5,741,248 A | 4/1998 | Stern et al. |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,769,879 A | 6/1998 | Richards et al. |
| 5,792,080 A | 8/1998 | Ookawa et al. |
| 5,800,490 A | 9/1998 | Patz et al. |
| 5,817,149 A | 10/1998 | Owens |
| 5,817,150 A | 10/1998 | Owens |
| 5,830,208 A | 11/1998 | Muller |
| 5,833,685 A | 11/1998 | Tortal et al. |
| 5,871,524 A | 2/1999 | Knowlton |
| 5,871,526 A | 2/1999 | Gibbs et al. |
| 5,895,418 A | 4/1999 | Saringer |
| 5,902,256 A | 5/1999 | Benaron |
| 5,919,219 A | 7/1999 | Knowlton |
| 5,948,011 A | 9/1999 | Knowlton |
| 5,954,680 A | 9/1999 | Augustine |
| 5,964,749 A | 10/1999 | Eckhouse et al. |
| 5,967,976 A | 10/1999 | Larsen et al. |
| 5,989,286 A | 11/1999 | Owens |
| 6,010,528 A | 1/2000 | Augustine et al. |
| 6,017,337 A | 1/2000 | Pira et al. |
| 6,023,932 A | 2/2000 | Johnston |
| 6,032,675 A | 3/2000 | Rubinsky et al. |
| 6,041,787 A | 3/2000 | Rubinsky |
| 6,102,885 A | 8/2000 | Bass |
| 6,104,959 A | 8/2000 | Spertell et al. |
| 6,106,517 A | 8/2000 | Zupkas et al. |
| 6,113,626 A | 9/2000 | Clifton et al. |
| 6,120,519 A | 9/2000 | Weber et al. |
| 6,152,952 A | 11/2000 | Owens |
| 6,241,753 B1 | 6/2001 | Knowlton et al. |
| 6,273,884 B1 | 8/2001 | Altshuler et al. |
| 6,311,090 B1 | 10/2001 | Knowlton et al. |
| 6,312,453 B1 | 11/2001 | Stefanile et al. |
| 6,350,276 B1 | 2/2002 | Knowlton et al. |
| 6,354,297 B1 | 3/2002 | Eiseman et al. |
| 6,375,673 B1 | 4/2002 | Clifton et al. |
| 6,377,854 B1 | 4/2002 | Knowlton et al. |
| 6,377,855 B1 | 4/2002 | Knowlton et al. |
| 6,381,497 B1 | 4/2002 | Knowlton et al. |
| 6,381,498 B1 | 4/2002 | Knowlton et al. |
| 6,387,380 B1 | 5/2002 | Knowlton et al. |
| 6,401,722 B1 | 6/2002 | Krag et al. |
| 6,405,090 B1 | 6/2002 | Knowlton et al. |
| 6,413,255 B1 | 7/2002 | Stern et al. |
| 6,425,912 B1 | 7/2002 | Knowlton et al. |
| 6,430,446 B1 | 8/2002 | Knowlton et al. |
| 6,432,124 B1 | 8/2002 | Worthen et al. |
| 6,453,202 B1 | 9/2002 | Knowlton et al. |
| 6,461,378 B1 | 10/2002 | Knowlton et al. |
| 6,470,216 B1 | 10/2002 | Knowlton et al. |
| 6,471,693 B1 | 10/2002 | Carroll et al. |
| 6,494,844 B1 | 12/2002 | Van Bladel et al. |
| 6,497,721 B2 | 12/2002 | Ginsburg et al. |
| 6,508,831 B1 | 1/2003 | Kushnir et al. |
| 6,519,964 B2 | 2/2003 | Bieberich et al. |
| 6,527,765 B2 | 3/2003 | Kelman et al. |
| 6,527,798 B2 | 3/2003 | Ginsburg et al. |
| 6,544,248 B1 | 4/2003 | Bass et al. |
| 6,548,728 B1 | 4/2003 | Faries et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,602,246 B1 * | 8/2003 | Joye ............... A61B 5/01 606/20 |
| 6,605,080 B1 * | 8/2003 | Altshuler ......... A61B 18/203 606/13 |
| 6,606,080 B2 | 8/2003 | Altshuler |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,635,053 B1 | 10/2003 | Lalonde et al. |
| 6,645,162 B2 | 11/2003 | Friedman et al. |

(56) References Cited

U.S. PATENT DOCUMENTS

| | | |
|---|---|---|
| 6,645,229 B2 | 11/2003 | Matsumura et al. |
| 6,648,904 B2 | 11/2003 | Altshuler et al. |
| 6,656,208 B2 | 12/2003 | Grahn et al. |
| 6,682,550 B2 | 1/2004 | Clifton et al. |
| 6,685,731 B2 | 2/2004 | Kushnir et al. |
| 6,695,874 B2 | 2/2004 | Machold et al. |
| 6,699,267 B2 | 3/2004 | Voorhees et al. |
| 6,741,895 B1 | 5/2004 | Gafni et al. |
| 6,749,624 B2 | 6/2004 | Knowlton et al. |
| 6,764,493 B1 | 7/2004 | Weber et al. |
| 6,789,545 B2 | 9/2004 | Littrup et al. |
| 6,840,955 B2 | 1/2005 | Ein et al. |
| 6,918,903 B2 | 7/2005 | Bass et al. |
| 6,927,316 B1 | 8/2005 | Faries et al. |
| 6,945,942 B2 | 9/2005 | Van Bladel et al. |
| 7,037,326 B2 | 5/2006 | Lee et al. |
| 7,060,061 B2 | 6/2006 | Altshuler et al. |
| 7,276,058 B2 | 10/2007 | Altshuler et al. |
| 7,367,341 B2 | 5/2008 | Anderson et al. |
| 7,572,268 B2 | 8/2009 | Babaev et al. |
| 7,615,016 B2 | 11/2009 | Barthe et al. |
| 7,713,266 B2 | 5/2010 | Elkins et al. |
| 7,824,437 B1 | 11/2010 | Saunders |
| 8,133,180 B2 | 3/2012 | Slayton et al. |
| 8,275,442 B2 | 9/2012 | Allison et al. |
| 8,285,390 B2 | 10/2012 | Levinson et al. |
| 8,333,700 B1 | 12/2012 | Barthe et al. |
| 8,366,622 B2 | 2/2013 | Slayton et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,535,228 B2 | 9/2013 | Slayton et al. |
| 8,603,073 B2 | 12/2013 | Allison et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,834,547 B2 | 9/2014 | Anderson |
| 8,840,608 B2 | 9/2014 | Anderson |
| 9,308,120 B2 | 4/2016 | Anderson |
| 9,358,149 B2 | 6/2016 | Anderson |
| 9,649,220 B2 | 5/2017 | Anderson |
| 10,582,960 B2 | 3/2020 | Avram |
| 2001/0005791 A1 | 6/2001 | Ginsburg et al. |
| 2001/0007952 A1 | 7/2001 | Shimizu et al. |
| 2001/0023364 A1 | 9/2001 | Ahn et al. |
| 2001/0047191 A1 | 11/2001 | Lasersohn et al. |
| 2001/0047196 A1 | 11/2001 | Ginsburg et al. |
| 2002/0026226 A1 | 2/2002 | Ein et al. |
| 2002/0032473 A1 | 3/2002 | Kushnir et al. |
| 2002/0049483 A1* | 4/2002 | Knowlton ............ A45D 44/22 607/101 |
| 2002/0058975 A1 | 5/2002 | Bieberich |
| 2002/0082668 A1 | 6/2002 | Ingman et al. |
| 2002/0107558 A1 | 8/2002 | Clifton et al. |
| 2002/0151830 A1 | 10/2002 | Kahn |
| 2002/0183667 A1 | 12/2002 | Kitadou et al. |
| 2002/0188286 A1 | 12/2002 | Quijano et al. |
| 2003/0032900 A1 | 2/2003 | Ella et al. |
| 2003/0069618 A1 | 4/2003 | Smith, III et al. |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0187488 A1 | 10/2003 | Kreindel et al. |
| 2003/0199859 A1 | 10/2003 | Altshuler et al. |
| 2003/0220635 A1 | 11/2003 | Knowlton et al. |
| 2003/0220674 A1 | 11/2003 | Anderson et al. |
| 2004/0024437 A1 | 2/2004 | Machold et al. |
| 2004/0034341 A1 | 2/2004 | Altshuler et al. |
| 2004/0049178 A1 | 3/2004 | Abboud et al. |
| 2004/0073079 A1 | 4/2004 | Altshuler et al. |
| 2004/0077977 A1 | 4/2004 | Rave et al. |
| 2004/0082886 A1 | 4/2004 | Timpson |
| 2004/0093042 A1 | 5/2004 | Altshuler et al. |
| 2004/0162596 A1 | 8/2004 | Altshuler et al. |
| 2004/0199226 A1 | 10/2004 | Shadduck et al. |
| 2004/0210214 A1 | 10/2004 | Knowlton et al. |
| 2004/0210287 A1 | 10/2004 | Greene et al. |
| 2004/0260211 A1 | 12/2004 | Maalouf |
| 2005/0049526 A1 | 3/2005 | Baer |
| 2005/0113725 A1 | 5/2005 | Masuda |
| 2005/0203446 A1 | 9/2005 | Takashima |
| 2005/0251120 A1 | 11/2005 | Anderson et al. |
| 2006/0036300 A1 | 2/2006 | Kreindel et al. |
| 2006/0094988 A1 | 5/2006 | Tosaya et al. |
| 2007/0010861 A1 | 1/2007 | Anderson et al. |
| 2007/0255362 A1 | 11/2007 | Levinson et al. |
| 2008/0139901 A1 | 6/2008 | Altshuler et al. |
| 2008/0287839 A1 | 11/2008 | Rosen et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0112134 A1 | 4/2009 | Avni |
| 2009/0149929 A1 | 6/2009 | Levinson et al. |
| 2009/0171334 A1 | 7/2009 | Elkins et al. |
| 2009/0264969 A1 | 10/2009 | Gammons |
| 2010/0015190 A1 | 1/2010 | Hassler |
| 2010/0036295 A1 | 2/2010 | Altshuler et al. |
| 2010/0081971 A1 | 4/2010 | Allison et al. |
| 2010/0152824 A1 | 6/2010 | Allison |
| 2010/0268220 A1 | 10/2010 | Johnson et al. |
| 2010/0280582 A1 | 11/2010 | Baker et al. |
| 2011/0040235 A1 | 2/2011 | Castel et al. |
| 2011/0040299 A1 | 2/2011 | Kim et al. |
| 2011/0046523 A1 | 2/2011 | Altshuler et al. |
| 2011/0066083 A1 | 3/2011 | Tosaya et al. |
| 2011/0112520 A1 | 5/2011 | Michael et al. |
| 2011/0172651 A1 | 7/2011 | Altshuler et al. |
| 2011/0196365 A1 | 8/2011 | Kim et al. |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2011/0313412 A1 | 12/2011 | Kim et al. |
| 2012/0010609 A1 | 1/2012 | Deem et al. |
| 2012/0022518 A1 | 1/2012 | Levinson |
| 2012/0022622 A1 | 1/2012 | Johnson et al. |
| 2012/0083862 A1 | 4/2012 | Altshuler et al. |
| 2012/0109041 A1 | 5/2012 | Munz |
| 2012/0209363 A1 | 8/2012 | Williams et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark et al. |
| 2012/0310232 A1 | 12/2012 | Erez et al. |
| 2013/0018236 A1 | 1/2013 | Altshuler et al. |
| 2013/0019374 A1 | 1/2013 | Schwartz |
| 2013/0073017 A1 | 3/2013 | Liu |
| 2013/0079684 A1 | 3/2013 | Rosen et al. |
| 2013/0116758 A1 | 5/2013 | Levinson et al. |
| 2013/0150730 A1 | 6/2013 | Altshuler et al. |
| 2013/0150844 A1 | 6/2013 | Deem et al. |
| 2013/0158440 A1 | 6/2013 | Allison |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2014/0005759 A1 | 1/2014 | Fahey et al. |
| 2016/0317346 A1 | 11/2016 | Kovach |

FOREIGN PATENT DOCUMENTS

| | | |
|---|---|---|
| DE | 1213584 A1 | 11/1992 |
| DE | 1224595 A1 | 1/1994 |
| EP | 0263069 B1 | 4/1988 |
| EP | 0397043 B1 | 11/1990 |

(56) References Cited

FOREIGN PATENT DOCUMENTS

| | | |
|---|---|---|
| EP | 0406244 B1 | 1/1991 |
| EP | 0263069 B1 | 4/1998 |
| FR | 854937 A | 4/1940 |
| FR | 2744358 A1 | 8/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 313679 A | 6/1929 |
| GB | 387960 A | 2/1933 |
| GB | 2120944 B | 12/1983 |
| GB | 2286660 | 3/1995 |
| JP | 01-223961 | 9/1989 |
| WO | WO 91/14417 A1 | 10/1991 |
| WO | 9623447 A1 | 8/1996 |
| WO | WO 97/24088 A1 | 7/1997 |
| WO | WO 98/31321 A1 | 7/1998 |
| WO | WO 98/41157 A1 | 9/1998 |
| WO | WO 99/09928 A1 | 3/1999 |
| WO | WO 99/16502 A1 | 4/1999 |
| WO | 9949937 A1 | 10/1999 |
| WO | WO 00/44346 * | 3/2000 |
| WO | WO 00/44346 A1 | 8/2000 |
| WO | 0100269 A1 | 1/2001 |
| WO | 0134048 A1 | 5/2001 |
| WO | WO 03/078596 A2 | 9/2003 |
| WO | WO 2004/000098 A2 | 12/2003 |
| WO | WO 2004080279 A2 | 9/2004 |

OTHER PUBLICATIONS

Examiner's First Report, Australian Patent Application No. 2009200451 (Feb. 16, 2011).
Written Opinion, Brazilian Patent Application No. PI0308642-9 (May 25, 2012).
Requisition, Canadian Patent Application No. 2,590,567 (Dec. 23, 2008).
Requisition, Canadian Patent Application No. 2,478,887 (Mar. 29, 2011).
Requisition, Canadian Patent Application No. 2,478,887 (Mar. 8, 2012).
First Office Action, Chinese Patent Application No. 038109387 (dated Jan. 9, 2007).
Second Office Action, Chinese Patent Application No. 038109387 (dated Nov. 7, 2008).
Notification of Re-Examination Decision, Chinese Patent Application No. 038109387 (Jun. 23, 2010).
Third Office Action, Chinese Patent Application No. 200910146673.7 (dated Apr. 25, 2013).
First Office Action, German Patent Application No. 10 2005 060 387.4-35 (dated Jan. 26, 2007).
Communication, European Patent Application No. 03716609 (Nov. 11, 2005).
Minutes of the oral proceedings, European Patent Application No. 07117532.7 (August 9,2010).
Communication, European Patent Application No. 101677565 (Auqust 31, 2010).
Communication, European Patent Application No. 101677565 (Oct. 25, 2010).
Communication, European Patent Application No. 101677565 (Jul. 4, 2011).
Summons to Attend Oral Proceedings, European Patent Application No. 101677565 (Dec. 29, 2011).
Communication, European Patent Application No. 101816973 (Sep. 19, 2012).
Result of Consultation, European Patent Application No. 101677565 (Mar. 19, 2012).
Result of Consultation, European Patent Application No. 101677565 (Mar. 26, 2012).
Provision of a Copy of the Minutes, European Patent Appl. No. 101677565 (Apr. 10, 2012).
First Examination Request for Indian Patent Application No. 2607/CHENP/2007 (Aug. 1, 2011).
Hearing Notice for Indian Patent Application No. 2607/CHENP/2007 (Jun. 12, 2013).
Official Action, Japanese Patent Application No. 2008-182599 (Dec. 21, 2010).
Official Action, Japanese Patent Application No. 2008-182599 (Jun. 28, 2011).
Office Action, Korean Patent Application No. 10-2011-7002259 (Mar. 22, 2011).
Notice of Final Rejection, Korean Patent Application No. 10-2011-7002259 (Mar. 26, 2012).
Notice Requesting Submission of Opinion, Korean Patent Application No. 10-2007-7015553 (Jun. 24, 2010).
Notice of Decision of Final Rejection, Korean Patent Application No. 10-2007-7015553 (Dec. 28, 2010).
Decision of Final Rejection, Korean Patent Application No. 10-2007-7015553 (Jun. 28, 2012).
Office Action, Korean Patent Application No. 10-2011-7022066 (dated Jan. 16, 2012).
Official Action, Mexican Patent Application No. MX/a/2007/007208 (Apr. 8, 2009).
Invitation to Respond to Written Opinion, Singapore Patent Application No. 200704450-6 (Apr. 9, 2009).
Examination Report, Great Britian Patent Application No. GB0525638.3 (Apr. 8, 2009).
Examination Report, Great Britian Patent Application No. GB0525638.3 (Jul. 14, 2009).
Invalidity Excerpts from Clinipro Technical Report for Spanish Patent ES 2 359 581 T3 (May 18, 2012).
Schoning, at al., "Experimental Frostbite: Freezing Times, Rewarming Times, and Lowest Temperatures of Piq Skin Exposed to Chilled Air," 27 Cryobiology 189-193 (1990).
Hong et al., "Patterns of Ice Formation in Normal and Malignant Breast Tissue," Cryobiology, 31:109-120 (1994).
Office Action, U.S. Appl. No. 10/391,221 (dated Jul. 22, 2005).
Office Action, U.S. Appl. No. 10/391,221 (dated Jan. 25, 2006).
Office Action, U.S. Appl. No. 10/391,221 (dated Aug. 24, 2006).
Office Action, U.S. Appl. No. 10/391,221 (dated May 30, 2007).
Office Action U.S. Appl. No. 13/895,285 (dated Sep. 5, 2013).
Office Action U.S. Appl. No. 13/895,287 (dated Aug. 30, 2013).
Office Action U.S. Appl. No. 13/896,291 (dated Sep. 5, 2013).
Office Action U.S. Appl. No. 13/896,637 (dated Sep. 13, 2013).
L'Vova, "[Lipid levels and lipid peroxidation in frog tissue during hyperthermia using an inductive aperture-type applicator: evaluation of the effect of tumour size and depth." Med Biol Eng Comput 37(3):285-90 (1999).
Kuroda et al., "Thermal distribution of radio-frequency inductive hyperthermia using an inductive aperture-type applicator: evaluation of the effect of tumour size and depth," 37(3) Med. Biol. Eng. Comput. 285-90 (1999).
Kundu et al., "Breath acetone analyzer:diagnostic tool to monitor dietary fat loss." Clin Chem Jan:39(1):87-92 (1993).
Kundu et al., "Novel solid-phase assay of ketone bodies in urine." Clin Chem Sep;37(9): 1565-9 (1991).
Hale et al., "Influence of chronic heat exposure and prolonged food deprivation on excretion of magnesium, phosphorus, calcium, hydrogen & ketones," Aerosp Med 39(9):919-26 (1968).
Nagao et al., "Dietary diacyglycerol suppresses accumulation of body fat compaired to triacylglycerol in men a double-blind controlled trial," J. Nutr. 130(4):792-7 (2000).
Bohm et al., "Saline-enhanced radiofrequency ablation of breat tissue; an in vitro feasibility study," Invest Radio 35 (3): 149-57 (2000).
Henry et al., Rev Med Liege 54(11):864-866 (Abstract translation) (1999).
Donski et al., "The Effects of Cooling no Experimental Free Flap Survival," Brit. J. Plas. Surg. 33:353-360 (1980).
Nielsen, "Thermoregulation In Rest and Exercise," Acta Phys Scan Supp 323:6-74 (1969).

(56) References Cited

OTHER PUBLICATIONS

Nagore et al., "Lipoatrophia semicircularis-a traumatic panniculitis: Report of seven cases and review of the iterature," Journal of the American Academy of Dermatology 879-881 (1998).
Heller Page et al., "Temperature-dependent skin disorders", Journal of the American Academy of Dermatology 18 (5): 1003-1019(1988).
Shephard, "Adaptation to Exercise in the Cold", Sports Medicine 2:59-71 (1985).
Henry et al., "LesDermatoses Hivermales" Rev Med Liege 54:11, 864-866 (1999).
Hong, "Patterns of Ice Formation in Normal and Malignant Breast Tissue" Cryobiology 31, 109-120 (1994).
Ardevol, "Cooling rates of tissue samples during freezing with liquid nitrogen" J. of Biochem. And Biophysical Methods 27, 77-86 (1993).
Holman, "Variation in cryolesion penetration due to probe size and tissue thermal conductivity" Ann. Thorac. Surg. 53, 123-126(1992).
Pech, "Attenuation values, vol. changes and artifacts in tissue due to freezing" Acta Radiologica 6, 779-782 (1987).
Hemmingsson, "Attenuation in Human Muscle and Fat Tissue in Vivo and in Vitro" Acta Radiologica Diagnosis 23, 149-151 -(1982).
Gage, "Current Progress in Cryosurgery" Cryobiology 25, 483-486 (1988).
Rubinsky, "Cryosurgery; advances in the application of low temperatures to medicine", Int. J. Refrig. 190-199 (1991).
Pease, An Integrated Probe for Magnetic Resonance Imaging Monitored Skin Cryosurgery: Journal of Biomedical Engineering 117, 59-63 (1995).
Rabi, "Metabolic adaptations in brown adipose tissue of the hamster in extreme ambient temperatures" American Journal of Physiology 231,153-160 (1976).
Laugier, et al., "In Vivo Results with a New Device for Ultrasonic Monitoring of Pig Skin Cryosurgery: The Echographic Cryoprobe", The Society for Investigative Dermatology, Inc., vol. 111(2) (Aug. 1998).
Bondei, E. et al., "Disorders of Subcutaneous Tissue (Cold Panniculitis)," Dermatology in General Medicine Chapter 108, Section 16 1333-1334 (1993).
Burge, S.M. et al., "Hair Follicle Destruction and Regeneration in Guinea Pig Skin after Cutaneous Freeze Injury," Cryobiology, 27(2):153-163 (1990).
Duncan, W.C. et al., "Cold Panniculitis," Arch Derm., 94:722-24 (1966).
Epstein, E.H. et al., "Popsicle Panniculitis" The New England Journal of Medicine, 282(17):966-67 (1970).
Kellum, R.E. et al., "Sclereme Neonatorum; Report of Case and Analysis of Subcutaneous and Epidermal-Dermal Lipids by Chromatographic Methods" Arch. Derm., 97:372-380 (1968).
Oska, J. et al., "Endocrine Regulation of Subcutaneous Fat Metabolism During Cold Exposure in Humans," Ann, N. Y. Acad. Sci 967:500-05 (2002).
Maize, J.C., "Panniculitis," Cutaneous Pathology, Chapter 13:327-344 (1998).
Malcom, G. et al., "Fatty Acid Composition of Adipose Tissue in Humans: Differences between Subcutaneous Sites," Am. J. Clin. Nutr., 60:725-29 (1994).
Moschella, S.L. et al., "Diseases of the Subcutaneous Tissue," Derm., Section 2:1169-1181 (1985).
Murphy, J.V. et al., "Frostbite: Pathogensesis and Treatment," The Journal of Trauma: Injury, Infection and Critical Dare, 48(1 ):171-178 (2000).
Phinney, S.D. et al., "Human Subcutaneous Adipose Tissue Shows Site Specific Differences in Fatty Acid Composition," Am. J. Clin. Null., 60:725-29 (1994).
Renold, A.E., "Adipose Tissue," Handbook of Physiology, Chapter 15:170-76, (1965).
Young, H.E. et al., "Isolation of Enbryonic Chick Myosatellite and Pluripotent Stem Cells," J. Tiss. Cult. Meth., 14:85-92 (1992).

First Action Interview Pilot Program Pre-Interview Communication, U.S. Appl. No. 11/434,478 (May 6, 2010).
First Action Interview Office Action Summary, U.S. Appl. No. 11/434,478 (dated Aug. 3, 2010).
Office Action, U.S. Appl. No. 11/434,478 (dated Nov. 10, 2010).
Office Action, U.S. Appl. No. 11/434,478 (dated Jun. 20, 2013).
Notification of Reexamination of State Intellectual Property Office, Chinese Patent Application No. 200910146673.7 (Jun. 27, 2014).
Rejection Decision, Chinese Patent Application No. 200910146673.7 (Oct. 29, 2013).
Judgment No. 169/2014, Barcelona Provincial Court (May 13, 2014).
Complaint, *ZELTIQ Aesthetics, Inc.* v. *Fischer*, District Court Munich—Patent Litigation Court (May 27, 2014).
Judgment No. 13/2013, *The General Hospital Corporation & Zeltiq Aesthetics Inc.* v. *Clinipro S.L. & Aquaestetica Consultores S.L.*, Commercial Court No. 5 of Barcelona (Jan. 25, 2013).
Opinion on Validity of the Patent EP1490005B1 (Validated in Spain as ES2300569T3) and EP1917935B1 (Validated in Spain as ES2359581) (Sep. 6, 2012).
Oppositional Document for Clinipro, S.L., Mercentile Court No. 5 of Barcelon (Mar. 22, 2013).
Pleading on behalf of Mace and Clinipro against The General Hospital Corporation and Zeltiq Aesthetics Inc., Docket No. 11/18480 (May 7, 2012).
Pleading No. 2 on behalf of Mace and Clinipro Against The General Hospital Corporation and Zeltiz Aesthetics Inc., Docket No. 11/18480 (Dec. 18, 2012).
Pleading No. 3 on behalf of Mr. Patrick Mace and Clinipro against The General Hospital Corporation and Zeltiq Aesthetics Inc, Docket No. 11/18480 (Mar. 19, 2013).
Judgment, *The General Hospital Corporation* v. *Mace*, Tribunal de Grande Instance de Paris, Docket No. 11/18480 (May 23, 2013).
Pleading, *Mace* v. *The General Hospital Corporation*, Division 5—Chamber 1, Docket No. 13/13050 (Sep. 26, 2013).
Authorized Statement of Defence of B&B Groups S.R.L, against New Technology Research Medical Equipment s.r.L and against Zeltiq Aesthetics Inc., Court of Milan, Business Division, Docket No. 41207/2012 (Mar. 25, 2013).
Examiner's First Report, Australian Patent Application No. 2003220311 (Apr. 16, 2007).
Requisition, Canadian Patent Application No. 2,478,887 (Dec. 22, 2009).
Requisition, Canadian Patent Application No. 2,590,567 (Apr. 30, 2009).
Requisition, Canadian Patent Application No. 2,590,567 (Oct. 15, 2009).
First Office Action, Chinese Patent Application No. 038109387 (dated Mar. 2, 2007).
Notice of Re-examination, Chinese Patent Application No. 038109387 (Nov. 16, 2009).
Rejection Decision, Chinese Patent Application No. 03810938.7 (Feb. 27, 2009).
Notice of Re-examination Decision, Chinese Patent Appl. No. 03810938.7 (Jun. 23, 2010).
First Office Action, Chinese Patent Application No. 20050048173.X (dated Jan. 23, 2009).
Second Office Action, Chinese Patent Application No. 20050048173.X (dated Jul. 10, 2009).
Rejection Decision, Chinese Patent Application No. 20050048173.X (Dec. 25, 2009).
Communication, European Patent Application No. 03716609.7 (Apr. 19, 2006).
Summons to attend oral proceedings, European Patent Application No. 03716609.7 (Jun. 12, 2007).
Supplementary Partial European Search Report, European Patent Application No. 03716609 (dated Nov. 11, 2005).
Communication, European Patent Application No. 05854660.7 (Nov. 27, 2007).
Communication, European Patent Application No. 05854660.7-2319 (Mar. 11, 2010).
Summons to Attend Oral Heading, European Patent Application No. 07117532.7 (Apr. 15, 2 010).

(56) References Cited

OTHER PUBLICATIONS

Communication, European Patent Application No. 07117532.7 (Jul. 10, 2009).
Communication, European Patent Application No. 07117532.7 (Sep. 9, 2008).
Communication, European Patent Application No. 07117532.7 (Apr. 3, 2008).
Examination Report, Great Britain Patent Application 0525638.3 (Jul. 14, 2009).
Notice Regarding Deficiencies, Israeli Patent Application No. 164115 (Aug. 4, 2008).
Notice Regarding Deficiencies, Israeli Patent Application No. 164115 (Sep. 16, 2009).
Office Action, Japanese Patent Application No. 2003-576590 (dated Aug. 5, 2008).
Office Action, Japanese Patent Application No. 2003-576590 (dated Apr. 7, 2009).
Office Action, Japanese Patent Application No. 2003-576590 (dated Dec. 17, 2009).
International Preliminary Examination Report, International Application No. PCT/US03/08014 (Mar. 29, 2004).
International Search Report, International Application No. PCT/US03/08014 (dated Sep. 23, 2003).
International Preliminary Report on Patentability, International Application No. PCT/US2005/045988 (Jun. 19, 2007).
Written Opinion, International Application No. PCT/US2005/045988 (Jun. 19, 2007).
Communication, European Patent Application No. 05 854 660 (Sept. 1,2008).
International Search Report, International Application No. PCT/US2005/045988 (Apr. 25, 2006).
Office Action, Japanese Patent Application No. 2007-547008 (dated Sep. 24,2008).
Examination Report, United Kingdom Patent Application GB052638.3 (Sep. 25, 2008).
Requisition, Canadian Patent Application No. 2,478,887 (Dec. 23, 2008).
Final Rejection, Japanese Patent Application No. 2007-547008 (Feb. 3, 2009).
Search Report and Written Opinion, Singapore Patent Application No. 200704450-6 (dated Apr. 9, 2009).
Nago et al., "Dietary diacyglycerol suppresses accumulation of body fat compared to triacylgycerol in men a doubleMind controlled trial," J. Nutr. 130(4):792-7 (2000).
Lidagoster et al., "Comparison of Autologous Fat Transfer in Fresh, Refrigerated, and Frozen Specimens: An Animal Model." Presented at the 16th Annual Meeting of the Northeastern Society of Plastic Surgeons: Burlington, VT, 512-515(1999).
Peterson et al. "Bilateral Fat Necrosis of the Scrotum," 116 Journal of Urology 825-826 (1976).
Levchenko et al., "[Effect of dehydration on lipid metabolism]." WMJ 50(l):95-7 (1978).
U.S. Appl. No. 20/120,158, filed Jun. 21, 2012, Schomacker.
Commuincation Pursuant to Rule 114(2) EPC, European Patent Application No. 10181697.3, Feb. 25, 2015, 121 pages.
Communication Pursuant to Article 94(3) EPC, European Patent Application No. 10181697.3, Jan. 30, 2014, 7 pages.
Communication Pursuant to Rule 114(2) EPC, European Patent Application No. 10181697.3, Jan. 15, 2014, 47 pages.
Decision of Appeal, Brazilian Patent Application No. 0308642-9, May 15, 2019, 6 pages.
Examination Decision of the Patent Examination Board, Chinese Patent Application No. 201010299471.9, Nov. 3, 2015, 22 pages.
Extended European Search Report, European Patent Application No. 17150653.8, dated Apr. 25, 2017, 9 pages.
First Office Action, Chinese Patent Application No. 201010299471.9, dated Dec. 7, 2011, 5 pages.
First Office Action, Chinese Patent Application No. 201510066314.6, 47 pages.
Notification of Reexamination of State Intellectual Property Office, Chinese Patent Application No. 201010299471.9, Jun. 9, 2015, 6 pages.
Office Action, U.S. Appl. No. 11/434,478, filed Mar. 20, 2014, 19 pages.
Office Action, U.S. Appl. No. 13/895,923, filed Aug. 30, 2013,18 pages.
Office Action, U.S. Appl. No. 13/896,285, filed Dec. 30, 2015, 20 pages.
Office Action, U.S. Appl. No. 13/896,285, filed Mar. 27, 2014, 20 pages.
Office Action, U.S. Appl. No. 13/896,285, filed Mar. 27, 2015, 21 pages.
Office Action, U.S. Appl. No. 13/896,287, filed Apr. 10, 2014, 19 pages.
Office Action, U.S. Appl. No. 13/896,287, filed Dec. 31, 2015, 8 pages.
Office Action, U.S. Appl. No. 13/896,287, filed Mar. 26, 2015, 20 pages.
Office Action, U.S. Appl. No. 13/896,291, filed Feb. 4, 2015, 44 pages.
Office Action, U.S. Appl. No. 13/896,291, filed Mar. 6, 2014, 35 pages.
Office Action, U.S. Appl. No. 13/896,291, filed Sep. 1, 2015, 24 pages.
Office Action, U.S. Appl. No. 13/896,637, filed Apr. 23, 2014, 23 pages.
Office Action, U.S. Appl. No. 13/896,637, filed Jan. 13, 2016, 12 pages.
Office Action, U.S. Appl. No. 13/896,637, filed Mar. 27, 2015, 15 pages.
Office Action, U.S. Appl. No. 15/374,762, filed Jan. 23, 2019, 11 pages.
Office Action, U.S. Appl. No. 15/374,784, filed Jan. 23, 2019, 13 pages.
Patent Examination Report No. 1, Australian Patent Application No. 2012204124, Nov. 29, 2013, 4 pages.
Patent Examination Report No. 1, Australian Patent Application No. 2015218441, Nov. 25, 2016, 5 pages.
Rejection Decision, Chinese Patent Application No. 201010299471.9, Sep. 4, 2013, 6 pages.
Second Office Action, Chinese Patent Application No. 201010299471.9, dated Sep. 10, 2012, 3 pages.
Summons to attend Oral Proceedings Pursuant to Rule 115(1) EPC, European Patent Application No. 10181697.3, Jul. 28, 2015, 6 pages.
Third Office Action, Chinese Patent Application No. 201010299471.9, dated Feb. 18, 2013, 6 pages.
Written Opinion, Brazilian Patent Application No. PI0308642-9, Jun. 21, 2011, 1 page.
Communication pursuant to Article 94(3) EPC, European Patent Applicaiton No. 17150653.8, Jun. 19, 2019, 65 pages.
Decision of Reexamination, Chinese Patent Application No. 201510066314.6, May 17, 2019, 6 pages.
Office Action, U.S. Appl. No. 13/374,762, filed Oct. 22, 2019, 12 pages.
Office Action, U.S. Appl. No. 13/374,784, filed Oct. 22, 2019, 9 pages.
Communication, European Patent Application No. 17 150 653.8 (Sep. 7, 2020).
Otten & Rubinsky, "Cryosurgical monitoring using bio-impedance measurements—a feasibility study for electrical mpedance tomography", IEEE Trans, of Biomedical Eng, vol. 27, No. 10, pp. 1376-1382, Oct. 2000.
Otten et al., "Distributed Network Imaging and Electrical Impedance Tomography of Minimally Invasive Surgery", 3(2) Tech. Cancer Res. & Treatment, Apr. 2004.
Hartov et al., "Using multiple-electrode impedance measurements to monitor cryosurgery", 29(12) Med. Phys. 2806-14, Dec. 2002.
Hearing Notice, Indian Patent Application No. 7028/CHENP/2013 (May 13, 2021).

* cited by examiner

METHODS AND DEVICES FOR SELECTIVE DISRUPTION OF FATTY TISSUE BY CONTROLLED COOLING

RELATED APPLICATIONS/PATENTS & INCORPORATION BY REFERENCE

This application is a continuation of U.S. patent application Ser. No. 11/016,196, filed Dec. 17, 2004 and issued as U.S. Pat. No. 8,840,608 on Sep. 23, 2014, which is a continuation-in-part of U.S. patent application Ser. No. 10/391,221, filed Mar. 17, 2003 and issued as U.S. Pat. No. 7,367,341 on May 6, 2008, which claims priority to U.S. Provisional Patent Application Ser. No. 60/365,662, filed Mar. 15, 2002.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

Not applicable.

FIELD OF THE INVENTION

The present invention relates to methods for use in the selective disruption of lipid-rich cells by controlled cooling. The present invention further relates to devices for use in carrying out the methods for selective disruption of lipid-rich cells by controlled cooling and for monitoring, detecting, influencing or acting upon conditions arising or otherwise present prior to, during and following the selective disruption methods. Other aspects of the invention are described in or are obvious from the following disclosure (and within the ambit of the invention).

BACKGROUND

The subcutaneous fatty tissue of newborns is unusually sensitive to the cold. In newborns, the intracellular lipid content of the subcutaneous fat cells, or "adipocytes," comprises increased ratios of highly saturated triglycerides. Even moderately cold temperatures can adversely affect cells having a highly saturated lipid content, rendering newborn subcutaneous fatty tissue vulnerable to adipocyte necrosis following exposure to the cold. Hypothermia of subcutaneous fatty tissue can result in associated inflammation of the dermis and/or epidermis. For example, disorders of cold panniculitis in newborns are known to produce painful skin lesions.

As newborns mature, the ratio of saturated to unsaturated fatty acids among intracellular triglycerides of adipocytes gradually decreases. Having a higher content of unsaturated fatty acids is more protective against the cold, and the occurrence of cold panniculitis in infants gradually subsides. For detailed reviews on the subject of cold panniculitis, see Epstein et al. (1970) New England J. of Med. 282(17):966-67; Duncan et al. (1966) Arch. Derm. 94:722-724; Kellum et al. (1968) Arch. Derm. 97:372-380; Moschella, Samuel L. and Hurley, Harry J. (1985) Diseases of the Corium and Subcutaneous Tissue. In Dermatology (W.B. Saunders Company):1169-1181; John C Maize (1998) Panniculitis In Cutaneous Pathology (Churchill Livingstone): 327-344; Bondei, Edward E. and Lazarus, Gerald S. (1993) Disorders of Subcutaneous Fat (Cold Panniculitis). In Dermatology in General Medicine (McGraw-Hill, Inc.): 1333-1334

In adults, the intracellular lipid content varies among cell types. Dermal and epidermal cells, for instance, are relatively low in unsaturated fatty acids compared to the underlying adipocytes that form the subcutaneous fatty tissue. For a detailed review of the composition of fatty tissue in mammals, see Renold, Albert E. and Cahill, Jr., George F. (1965) Adipose Tissue. In Handbook of Physiology (American Physiology Society):170-176. As a result, the different cell types, e.g., lipid-rich and non-lipid-rich cells, have varying degrees of susceptibility to the cold. In general, non-lipid-rich cells can withstand colder temperatures than lipid-rich cells.

It would be highly desirable to selectively and non-invasively damage adipocytes of the subcutaneous fatty tissue without causing injury to the surrounding dermal and epidermal tissue. Both health and cosmetic benefits are known to result from reduction of fatty tissue, however, current methods, such as liposuction, involve invasive procedures with potentially life threatening risks (e.g., excessive bleeding, pain, septic shock, infection and swelling).

Current methods for non-invasive removal of subcutaneous fatty tissue include the use of radiant energy and cooling solutions. U.S. Pat. Nos. 5,143,063; 5,507,790; and 5,769,879 describe methods for using radiant energy to reduce subcutaneous fatty tissue, however, the applied energy levels are difficult to control and often there is collateral damage to the dermis and/or epidermis. Cooling solutions proposed by International Publication No. WO 00/44346 do not stabilize skin surface temperatures and therefore, also fail to adequately protect against collateral damage to the dermis and/or epidermis.

A previous study conducted in Guinea Pigs described the removal of subcutaneous fatty tissue by cryo-damage. Burge, S. and Dawber, R. (1990) Cryobiology 27:153-163. However this result was achieved using relatively aggressive cooling modalities (e.g., liquid nitrogen), which induced epidermal damage. Ideally, removal of subcutaneous fatty tissue by cooling would not cause associated damage to the epidermis.

Temperature controlled methods and devices for selectively damaging lipid-rich cells (e.g., adipocytes comprising the subcutaneous fatty tissue) without causing injury to non lipid-rich cells (e.g., dermis and/or epidermis) were heretofore unknown.

SUMMARY OF THE INVENTION

It has now been shown that adipose tissue comprising lipid-rich cells can be selectively disrupted without causing injury to the surrounding non lipid-rich tissue (e.g., dermal and epidermal tissue) by controlling the temperature and/or pressure applied to the respective tissues.

In one aspect, the invention relates to cooling methods for selective disruption of lipid rich cells in a non-infant human treatment subject, the methods comprising applying at least one cooling element proximate to an application site of the treatment subject; utilizing the cooling element to decrease the temperature beneath the application site, wherein the temperature decrease is sufficient to disrupt and thereby reduce lipid rich cells therein; and while the temperature is decreased, utilizing at least one feedback device to provide feedback information sufficient to confirm that non lipid rich cells proximate to the cooling element are not disrupted, thereby selectively disrupting lipid rich cells in the subject.

In one embodiment, the method can further comprise applying pressure proximate to the application site of the treatment subject, wherein the pressure applied is effective to decrease blood flow beneath the application site.

In another aspect of the invention, a system for providing feedback information in connection with selective disruption of lipid rich cells in a non-infant human treatment subject is provided, the system comprising at least one cooling element proximate to an application site of the treatment subject, wherein the cooling element is effective to decrease the temperature beneath the application site, and wherein the temperature decrease is sufficient to disrupt and thereby reduce lipid rich cells beneath the application site; and at least one feedback device in communication with at least one cooling element, wherein the feedback device provides feedback information sufficient to confirm that non lipid rich cells proximate to the cooling element are not disrupted.

In yet another aspect of the invention, a system for providing feedback information in connection with selective disruption of lipid rich cells in a non-infant human treatment subject is provided, the system comprising at least one cooling element proximate to an application site of the treatment subject, wherein the cooling element is effective to decrease the temperature beneath the application site, and at least one feedback device in communication with at least one cooling element, wherein the feedback device provides feedback information sufficient to confirm that the temperature decrease is sufficient to disrupt and thereby reduce lipid rich cells beneath the application site.

In any aspect of the invention, the feedback information can comprise information (e.g., data, signals) about physiological parameters of the dermis, epidermis or subcutaneous adipose tissue indicating that non lipid rich cells proximate to the cooling element are not disrupted.

One or more feedback devices can be included to provide feedback information relating to the cooling process. The feedback device(s) can be in communication with (e.g., connected to, in direct contact or in indirect contact with) at least one cooling element and/or can be in communication with (e.g., in direct contact or in indirect contact with) the application site. For example, the feedback device(s) can be integrated within small channels of the cooling element. In such an embodiment of the invention, the channels are generally less than about 1 cm in diameter.

In accordance with an exemplary aspect of the cooling method of the present invention, the feedback information provided can pertain to one or more pieces of information, including, but not limited to information relating to at least one physiological parameter of the dermis, epidermis and/or subcutaneous adipose tissue. For example, this information can indicate/confirm that non lipid rich cells proximate to the cooling element have not been disrupted by the cooling process, and/or that disruption of lipid rich cells has occurred. The lipid rich cells that are cooled/disrupted can be, e.g., adipocytes within the subcutaneous adipose tissue.

Another exemplary physiological parameter for which feedback information can be provided is the presence of substantial crystal formation in the subject's dermis and/or epidermis or subcutaneous adipose tissue. In such an embodiment of the invention, the presence/absence of substantial crystal formation can be indicated by an electrical impedance of between about 10 k$\Omega$/mm to about 50 k$\Omega$/mm in the subject's dermis or epidermis and above about 10 k$\Omega$/mm in the subject's subcutaneous adipose tissue, or by an ultrasound acoustic velocity of between about 1450 to less than about 2700 M/S in the subject's dermis or epidermis and above about 2700 M/S in the subject's subcutaneous adipose tissue.

Still another physiological parameter for which feedback information can be provided is the amount of stiffness in the subject's dermis, epidermis and/or subcutaneous adipose tissue.

Yet another physiological parameter for which feedback information can be provided is the amount of pressure in the subject's dermis, epidermis and/or subcutaneous adipose tissue, wherein the pressure reading should be at least about 240 mm Hg in subcutaneous adipose tissue in the dermis and epidermis and between about 120 mm Hg and about 240 mm Hg in accordance with a specific embodiment of the present invention.

An additional physiological parameter for which feedback information can be provided is whether there has been a phase transition in the subject's dermis or epidermis.

A further physiological parameter for which feedback information can be provided is the acoustic velocity in the subject's dermis or epidermis, wherein an acoustic velocity should be in the range of about 1450 M/S to less than about 2700 M/S in the subject's dermis or epidermis and greater than about 2700 M/S in the subject's subcutaneous adipose tissue in accordance with a specific embodiment of the present invention.

A still further physiological parameter for which feedback information can be provided is reflectance or transmittance from within the subject's dermis, epidermis and/or subcutaneous adipose tissue, wherein the spectrum of reflectance is monitored in accordance with a specific embodiment of the present invention.

An exemplary feedback device is an invasive or non-invasive temperature probe. The temperature probe can be a thermoprobe, such as a radiation thermometer, fiber optical temperature sensor and thermal imaging thermoprobe. Suitable thermoprobes include, but are not limited to a thermocouple, a thermistor, a bimetallic thermometer, color changing thermal indicator paper, a semiconductor thermometer, a fiber optical thermometer, and a liquid in glass thermometer.

Examples of other exemplary feedback devices are an electrical feedback probe, an ultrasound probe (e.g., an echographic cryoprobe), an oscillating feedback probe (e.g., a piezoelectric vibrator), a contact probe (e.g., a pressure probe, such as a spring loaded cooling element), an optical coherence tomographic device, optical spectropic device, and/or a magnetic resonance imaging device.

In this disclosure, "comprises," "comprising," "containing" and "having" and the like can have the meaning ascribed to them in U.S. patent law and can mean "includes," "including," and the like; "consisting essentially of or" consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

These and other objects and embodiments are described in or are obvious from and within the scope of the invention, from the following Detailed Description.

DESCRIPTION OF THE DRAWINGS

So that those having skill in the art will understand how to enjoy the systems and methods of the subject matter, embodiments thereof shall be described herein below with reference to the drawings wherein:

FIG. 7A shows the low magnification view and FIG. 7B shows the high magnification view, FIG. 15A depicts a low magnification view. FIG. 15B depicts a high magnification view, FIG. 16A depicts a low magnification view. FIG. 16B depicts a high magnification view.

DETAILED DESCRIPTION

Figure 1A:
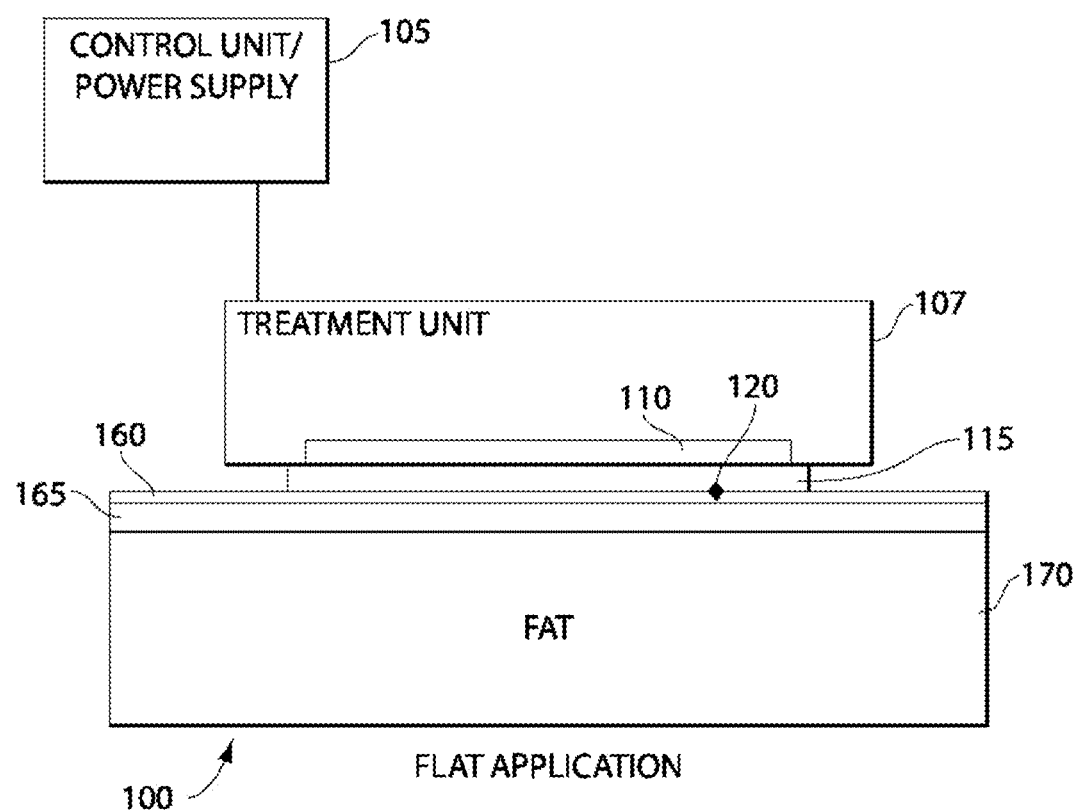
FIG. 1A illustrates a treatment system.

The present invention relates to a method for locally reducing adipose tissue comprising applying a cooling element to a subject at a temperature sufficient to selectively disrupt lipid-rich cells, wherein the temperature does not produce unwanted effects in non lipid-rich cells. Preferably, the cooling element is coupled to or contains a cooling agent.

Methods of the invention comprise for treating a region of a subject's body to achieve a desired reduction in subcutaneous adipose tissue, by a) applying a cooling element proximate to the subject's skin in the region where subcutaneous adipose tissue reduction is desired to create a temperature gradient within said region sufficient to selectively disrupt lipid-rich cells therein, and, simultaneously therewith maintain the subject's skin at a temperature wherein non lipid-rich cells proximate to the cooling element are not disrupted; b) repeating the application of the cooling element to the subject's skin of step (a) a plurality of times until the desired reduction in subcutaneous adipose tissue has been achieved.

Cooling elements of the present invention can contain cooling agents in the form of a solid, liquid or gas. Solid cooling agents can comprise, for example thermal conductive materials, such as metals (e.g., copper, silver, aluminum), metal plates, glasses, ceramics, gels and ice or ice slurries. In one embodiment, the solid cooling agent is a Peltier element which is in contact with the cooling element. Peltier elements are well known in the art (e.g., Peltier elements made of bismuth telluride are manufactured by Applied Biosystems). Liquid cooling agents can comprise, for example, saline, glycerol, alcohol, or water/alcohol mixtures. Where the cooling element includes a circulating cooling agent, preferably the temperature of the cooling agent is constant and preset to the desired temperature. The appropriate temperature of the cooling agent can vary according to the thermal conductivity, heat capacity and/or flow rate of the cooling agent and can be readily determined by one skilled in the art. Salts or other additives can be combined with liquid mixtures to obtain desired temperatures. Gasses can include, for example, cold air or liquid nitrogen.

Cooling elements of the invention provide cooling to an application site. Cooling applied to the application site can be direct, indirect, active or passive. In one embodiment, cooling elements can be applied such that direct contact is made with a subject, via either the agent or the element. In another embodiment, direct contact is made via the agent alone. In yet another embodiment, no direct contact is made via either the agent or the element; cooling is carried out by proximate positioning of the cooling element and/or agent.

Preferably, the temperature of the cooling agent is less than about 37° C., but not less than −196° C. (i.e., the temperature of liquid nitrogen).

Preferably, the temperature range of the administered cooling element is between about 40° C. and −15° C., more preferably between 4° C. and −10° C. and even more preferably between 0° C. and −3° C. if the cooling agent is a liquid or a solid. Generally, the cooling element is preferably maintained at an average temperature of between about −15° C. and about 35° C., 30° C., 25° C., 20° C., 15° C., 10° C., or 5° C.; about −10° C. and about 35° C., 30° C., 25° C., 20° C., 15° C., 10° C., or 5° C.; about −5° C. and about 20° C., 15° C., 10° C., or 5° C.

The cooling element and/or agent can be applied for up to two hours. Preferably, the cooling element is applied for between 1 to 30 minutes. The cooling element can be applied for at least one hundred milliseconds (e.g., shorter durations are envisioned, for instance, with sprays). For example, liquid nitrogen can be applied in very short intervals (e.g., about 1 second), repeatedly (e.g., about 10-100 times) and between applications, a temperature that does not cause epidermal damage is maintained (e.g., about 0° C. to −10° C., depending on the length of exposure). In a gentle cooling regime, for example, the liquid nitrogen can be sprayed from a distance (e.g., from about 10 to 30 cm) wherein some portion of the liquid nitrogen droplets evaporate during the spraying and/or mix with ambient air.

Cooling elements and/or agents of the present invention are applied, for example, to the skin surface through either direct or indirect contact. Indirect contact can be mediated by a conductive material, such as a membrane, lotion, liquid (e.g., water) or a gel to alter or moderate thermoconductivity as desired.

A subject's skin comprises the epidermis, dermis or a combination thereof. The cooling element and/or agent is a non-toxic cooling agent when applied directly to the skin surface.

The cooling element and/or agent can be applied more than once, for example, in repetitious cycles. The cooling agent can be applied in a pulsed or continuous manner. The cooling element and/or agent can be applied by all conventional methods known in the art, including topical application by spray if in liquid form, gas or particulate solid material. Preferably, application is by external means, however, cooling elements and/or agents of the present invention can also be applied subcutaneously by injection or other conventional means. For example, the cooling agent can be applied directly to the subcutaneous tissue and then either removed after contact or left in the subcutaneous tissue to achieve thermal equilibration and therefore cooling of the lipid-rich tissue (e.g., subcutaneous injection of a liquid cooling agent or of small cooling particles, such as pellets or microbeads).

Preferably, methods of the present invention are non-invasive (e.g., superficial, laparoscopic or topical procedures not requiring invasive surgical techniques).

The cooling element and/or agent can be applied to one defined area or multiple areas. Spatial distribution of the cooling element and/or agent can be controlled as needed. Generally, the dimension of the surface area (e.g., where the cooling agent is in contact with the skin) should be at least three times the depth of subcutaneous fatty tissue that is targeted for cooling. Preferably, the minimum diameter of the surface area is at least 1 cm$^2$. Even more preferably, the diameter of the surface area is between 3 to 20 cm$^2$ for each application site. Multiple cooling applicators can be used, either in a substantially simultaneous or successive or sequential manner.

Determination of the optimal surface area will require routine variation of several parameters. For example, larger surface areas, such as those over 3500 cm$^2$, can be cooled according to the methods of the present invention if hypothermia is prevented by additional means. Hypothermia can be prevented by compensating for the heat transfer away from the body at other sites (e.g., applying warm water at one or more additional sites). Multiple cooling elements and/or agents can be employed, for example, in contacting larger surface areas (e.g., greater than 3500 cm$^2$).

The cooling element and/or agent can follow the contour of the area to which it is applied. For example, a flexible apparatus can be used to follow the contour of the surface area where cooling is applied. The apparatus can also modify the shape of the contacted surface such that the surface is contoured around or within the cooling agent or the apparatus containing the cooling agent upon contact. The cooling element and/or agent can contact more than one surface at once, for example, when the surface is folded and contacted on either side by the cooling element and/or agent. Preferably, one or more skin folds are contacted on both sides by the cooling element and/or agent to increase the efficiency of cooling (e.g., at a desired depth through successive layers).

Preferably, the solid cooling element and/or agent is shaped to enhance thermodynamic heat exchange ("thermal exchange") at the contacted surface (e.g., skin surface). In order to enhance conduction, a liquid can be used at the interface between the solid cooling agent and the contacted surface.

Where necessary, application of the cooling element and/or agent can be coupled with use of a pain management agent, such as an anesthetic or analgesic (cooling alone has analgesic properties, thus use of additional pain management agents is optional). Local anesthetics, for example, can be topically applied at the point of contact either before, after or during application of the cooling agent. In addition, co-administration of local anesthetics having vasoconstrictive properties (e.g. lidocaine with epinephrine or EMLA) will decrease dermal blood flow, thereby enhancing the cooling of subdermal tissue.

Where necessary, systemic administration of the anesthetic can be provided through conventional methods, such as injection or oral administration. The temperature of the cooling agent can be changed during the treatment, for example, so that the cooling rate is decreased in order to provide a treatment causing less discomfort. In addition, methods of the present invention can be performed in combination with other fat reduction procedures known in the art, such as liposuction.

Preferably, lipid-rich cells of the present invention are adipocytes within subcutaneous fatty tissue or cellulite. Thus, lipid-rich cells comprising the subcutaneous adipose tissue are targeted for disruption by methods of the present invention. In addition, it is within the ambit of the invention to target disruption of lipid-rich cells comprising adventicia surrounding organs or other internal anatomical structures.

The intracellular lipids of adipocytes are confined within the paraplasmatic vacuole. There are univacular and plurivacular adipocytes within the subcutaneous fatty tissue. Most are univacular, and greater than about 100 um in diameter. This size can increase dramatically in obese subjects due to an increase in intracellular lipid content.

Preferably, lipid-rich cells of the present invention have a total intracellular lipid content of between 20-99%. Preferably, lipid-rich cells of the present invention have an intracellular lipid content comprised of about 20-50% saturated triglycerides, and even more preferably about 30-40% saturated triglycerides. Intracellular triglycerides include, but are not limited to, saturated fatty acids e.g., myristic, palmitic and stearic acid; monounsaturated fatty acids, e.g., palmitoleic and oleic acid; and polyunsaturated fatty acids e.g., linoleic and linolenic acid.

Preferably, lipid-rich cells of the present invention are located within subcutaneous adipose tissue. The saturated fatty acid composition of subcutaneous adipose tissue varies at different anatomical positions in the human body. For example, human subcutaneous adipose tissue in the abdomen can have the following composition of saturated fatty acids: myristic (2.6%), palmitic (23.8%), palmitoleic (4.9%), stearic (6.5%), oleic (45.6%), linoleic (15.4%) and linolenic acid (0.6%). The subcutaneous adipose tissue of the abdominal area can comprise about 35% saturated fatty acids. This is comparatively higher than the buttock area, which can comprise about 32% saturated fatty acids. At room temperature, saturated fatty acids of the abdominal area are in a semisolid state as a result of the higher fatty acid content. The buttock area is not similarly affected. Malcom G. et al., (1989) Am. J. Clin. Nutr. 50(2):288-91. One skilled in the art can modify temperature ranges or application times as necessary to account for anatomical differences in the response to cooling methods of the present invention.

Preferably, non lipid-rich cells of the present invention have a total intracellular lipid content of less than 20%, and/or are not disrupted by cooling methods of the present invention. Preferably, non lipid-rich cells of the present invention include cells having an intracellular lipid content comprising less than about 20% highly saturated triglycerides, even more preferably less than about 7-10% highly saturated triglycerides. Non lipid-rich cells include, but are not limited to, those surrounding the subcutaneous fatty tissue, such as cells of the vasculature, peripheral nervous system, epidermis (e.g., melanocytes) and dermis (e.g., fibrocytes).

Damage to the dermis and/or epidermis that is avoided by the methods of the present invention can involve, for example, inflammation, irritation, swelling, formation of lesions and hyper or hypopigmentation of melanocytes.

Without being bound by theory, it is believed that selective disruption of lipid-rich cells results from localized crystallization of highly saturated fatty acids upon cooling at temperatures that do not induce crystallization of highly saturated fatty acids in non lipid-rich cells. The crystals rupture the bilayer membrane of lipid-rich cells, causing necrosis. Thus, damage of non lipid-rich cells, such as dermal cells, is avoided at temperatures that induce crystal formation in lipid-rich cells. It is also believed that cooling induces lipolysis (e.g., metabolism) of lipid-rich cells, further enhancing the reduction in subcutaneous adipose tissue. Lipolysis may be enhanced by local cold exposure inducing stimulation of the sympathetic nervous system.

It has been determined that the effects of cooling on the disruption of fatty tissue are enhanced by the simultaneous application of mechanical force (e.g., vibration). The stiffness of fatty tissue increases at temperatures below physiological body core temperature, thereby becoming more susceptible to physical disruption. Without being bound by theory, it is believed that the disruptive effects of crystal formation on a cell membrane are enhanced by physical movement provided after cooling or concomitantly therewith. Accordingly, methods of the invention can further comprise the application of mechanical force, such as vibration at a frequency in the range of about 5 to about 200 Hz.

In one embodiment, the temperature of the lipid-rich cells is not less than about −10° C. Preferably, the temperature of the lipid-rich cells is between −10° C. and 37° C. More preferably, the temperature of the lipid-rich cells is between −4° C. and 20° C. Even more preferably, the temperature of the lipid-rich cells is between −2° C. and 15° C. Preferably, the lipid-rich cells are cooled to less than 37° C., for up to two hours. Generally, the lipid-rich cells are preferably maintained at an average temperature of between about −10° C. and about 37° C., 35, 30° C., 25° C., 20° C., 15° C., 10° C., or 4° C.; about −4° C. and about 35° C., 30° C., 25° C., 20° C., 15° C., 10° C., or 4° C.; about −2° C. and about 35° C., 30° C., 25° C., 20° C., 15° C., 10° C., or 5° C.; and between about 5° C. and about 15° C. or 20° C.

Cooling methods of the present invention advantageously eliminate unwanted effects in the epidermis. In one embodiment, the temperature of the epidermis is not less than about −15° C. Preferably, the temperature of the epidermis is between about −10° C. and 35° C. More preferably, the temperature of the epidermis is between about −5° C. and 10° C. Even more preferably, the temperature of the epidermis is between about −5° C. and 5° C. Even more preferably, the temperature of the epidermis is between about 0° C. and 5° C.

Cooling methods of the present invention advantageously eliminate unwanted effects in the dermis. In one embodiment, the temperature of the dermis is not less than about −15° C. Preferably, the temperature of the dermis is between about −10° C. and 20° C. More preferably, the temperature of the dermis is between about −8° C. and 15° C. Even more preferably, the temperature of the dermis is between about −5° C. and 10° C. Even more preferably, the temperature of the dermis is between about −3° C. and 0° C.

In a preferred embodiment, the lipid-rich cells are cooled to about −5° C. to 5° C. for up to two hours and the dermal and epidermal cells maintain an average temperature of about 0° C. In a most preferred embodiment, the lipid-rich cells are cooled to about −5 to 15° C. or about 5 to 15° C. for times ranging from about a minute, up to about two hours.

Methods of the present invention can be applied in short intervals (e.g., 1 minute, 5 minute, 15 minute, 30 minute and 60 minute time intervals) or long intervals (e.g., 12 hour and 24 hour time intervals). Preferably intervals are between 5 and 20 minutes. Heat can optionally be applied between intervals of cooling.

Various feedback mechanisms, devices or apparatus can be employed in accordance with the present invention in order to monitor and control physiologic parameters of the skin (i.e., dermis, epidermis or a combination thereof) and/or the subcutaneous adipose tissue. A feedback mechanism can include one or more devices working independently, in concert, and/or with other devices disclosed herein for the purpose of monitoring, gauging or otherwise detecting various aspects (e.g., temperature, duration, etc.) of the cooling process, and/or to control, modify, or otherwise influence the operating conditions (e.g., level of cooling, pressure, etc.) of the equipment utilized in accordance with the cooling process.

According to a currently preferred embodiment of the present invention, at least one of the feedback devices is capable of determining not only when a desired cooling temperature (or temperature range) is reached, but also if a temperature (or temperature range) threshold has been exceeded or is approaching the point at which it would be exceeded. This temperature determination can be made at the cooling site, within the cooling device, and/or remote from the cooling site. This, in turn, enables the feedback device to reliably provide sufficient feedback information to prevent both over- and under-treatment, both of which are undesired for various reasons (e.g., inefficacious results, unwanted side effects, potential harm to the device and/or treatment subject, etc.).

The one or more feedback devices also can provide other feedback options in addition to or in lieu of temperature-based feedback. Such alternate feedback information can determine or can assist in determining, inter alia, (a) whether appropriate contact exists between the treatment device and the treatment surface, (b) whether phase transitions have occurred in the skin, (c) whether and/or to what extent a skin color change has occurred, (d) whether the optical reflection or transmission spectrum has changed, and/or (e) whether the electrical resistance of the skin has changed, and also can measure or assist in measuring, inter alia, (a) the pressure that is being exerted on the treatment surface, and/or (b) the changes in the level of stiffness of the skin.

The feedback device(s) can provide feedback information in a variety of ways, including, but not limited to, visually (e.g., graphically), electronically and aurally (e.g., verbally). Feedback information can be provided such that the operating conditions of one or more devices in the cooling system are automatically adjusted (e.g., via control logic or programmable logic), or such that an operator must assess the feedback information and then take appropriate action.

The recipient of the feedback information can be one or more operators, including, but not limited to the treatment subject, medical personnel (e.g., doctor, nurse, resident, medical student), technician, and/or anyone else involved in the treatment process. Based on the feedback information received, the operator(s) can elect to halt the treatment process or to modify (e.g., manually or via input controls) certain treatment parameters, such as the duration of the treatment process, the site at which treatment process is occurring, and/or the current or future cooling temperature for the treatment process.

The determination as to whether to halt the process or to modify the treatment conditions can be based upon, e.g., operator judgment, or, as is currently preferred, actual or experimental data gathered from previous treatments to which the current treatment can be likened. For example, data from animal experiments can be utilized to determine how to set and/or modify operating parameters when treating humans. Also, data relating to certain treatment areas of the body can be relied upon to set and/or modify treatment parameters for future treatments of the same or similar body parts of the same or similar treatment subject.

Alternatively, the feedback information can be delivered to control logic, such as a central control unit, or to a programmable logic device (e.g., a computer) as would be known to one of ordinary skill in the art.

According to an exemplary embodiment of the present invention, a feedback mechanism can monitor the temperature of a subject's skin to ensure that the temperature therein does not fall below or above a predetermined minimum temperature (e.g., about $-10°$ C. to about $30°$ C.), and/or that the temperature is within a desired range during either the entirety of the process or predetermined portions thereof. Thus, a feedback mechanism can monitor and/or control whether a level of cooling is achieved, and, if so, for how long (i.e., for what portions of the process) and/or under what circumstances (i.e., constant or intermittent cooling).

A feedback device can be invasive, non-invasive or applicable to usage under both such conditions, with the specific choice between invasive or non-invasive being dependent on a variety of circumstances including, but not limited to, the location of the treatment site, the duration of treatment, the age of the treatment subject, the general health of the treatment subject, and/or the size and shape of the cooling equipment being used. The following definitions of the terms "non-invasive" and "invasive" are illustrative and are not intended to exclude other definitions that would be acceptable to one of ordinary skill in the art.

A non-invasive feedback device is one that is located external to the treatment subject—that is, a non-invasive feedback device does not perforate the application site in accordance with its intended usage. When used, a non-invasive feedback device generally does not require accompanying sedation or anesthesia for the treatment subject. It is understood, however, that a treatment subject may be given or may decide to receive accompanying sedation or anesthesia due to certain circumstances (e.g., anxiety regarding the treatment process, underlying medical condition).

Invasive feedback devices perforate the treatment surface (i.e., they are wholly or partially internal) during at least a portion of the feedback process. Invasive feedback devices include, but are not limited to, devices that, when used, generally call for the treatment subject to receive sedation, anesthesia (e.g., local or general), or other type of medicinal pain relief prior to, during and/or following the treatment process. Analgesia can also be provided by cooling.

Feedback mechanisms can include all known in the art to monitor temperature and/or crystal formation. Crystal formation can be measured, for example by ultrasound imaging and acoustical, optical, and mechanical measurements. Mechanical measurements can include, for example, measurements of tensile strength.

In one embodiment, a multilayer model can be employed to estimate temperature profiles over time and within different depths. Temperature profiles are designed to produce a temperature gradient within the tissue, having a lower temperature at the surface. In a preferred embodiment, temperature profiles are designed to minimize blood flow during cooling. Feedback mechanisms comprising, for example, thermocouples, ultrasound (e.g., to detect phase changes of the subcutaneous adipose tissue) or shock wave propagation (e.g., propagation of a shock wave is altered if a phase transition occurs) can be employed to achieve optimal temperature gradients.

Temperature probes (i.e., thermoprobes) are currently preferred for non-invasive applications because they can be sited in a variety of locations and serve a variety of purposes.

In other embodiments, the probes can be used invasively. Thermoprobes can include devices capable of measuring temperature by direct contact with a measurement site/location (e.g., thermocouples, thermistors, bimetallic thermometers, color changing thermal indicator paper, semiconductor thermometers, fiber optical thermometers, liquid in glass thermometers), or, alternatively, devices which do not make contact with a site (e.g., radiation thermometers, fiber optical temperature sensors, thermal imaging).

There are several types of thermoprobe feedback devices that may be employed. In generally, the type, purpose and location of a thermoprobe are at least somewhat dependant upon each other. For example, the purpose of a thermoprobe (i.e., the reason for using the thermoprobe) can influence its placement location, which, in turn, can influence factors involved in deciding which type of thermoprobe to use.

In embodiments wherein the purpose of the thermoprobe is to provide a reliable, current temperature measurement of the portion of the cooling device that is (or will be) in communication with a treatment surface, it is currently preferred to locate the thermoprobe such that it is in communication with the surface of a cooling element/device but not in thermal contact with the actual treatment surface during the treatment process. For example, the thermoprobe can be temporarily attached to the cooling device (e.g., as a disposable thermally conductive plate), or it can be permanently fixed thereto. In accordance with both such embodiments, it is currently preferred that the type of thermoprobe is a thermocouple, thermistor or semiconductor thermometer.

When used, feedback devices that are attached to the surface of a cooling device are placed in communication with the skin surface (i.e., upper epidermis) of a treatment subject. Thus, such feedback devices are advantageous in that they provide a reliable assessment of the cold exposure of the upper epidermis, which is especially prone to the rapid onset of unwanted side effects (e.g., epidermal damage or pigmentary changes) due to cold exposure.

According to an alternate embodiment of the present invention, the temperature of the surface of the upper epidermis is measured by a feedback device that is detachably affixed to the surface of the treatment site/area. In such an embodiment, the method of affixture should allow for reliably adherent, yet temporary joinder of the device to the treatment surface—that is, the device should be reliably affixed to the treatment surface, yet should also be capable of being easily removable from the surface at a desired instance (e.g., at the culmination of the process, or, if a problem occurs, at some earlier point in time). Suitable affixture methods include, but are not limited adhesives such as tape or glue. In an embodiment wherein the thermoprobe is affixed to the treatment surface via glue, the thermoprobe can be removed from the treatment surface using an appropriate solvent.

As noted above, it is currently preferred that the minimum temperature of the upper epidermis of the treatment subject (i.e., the temperature below which the upper epidermis should not drop during the cooling treatment) is −10° C. during treatment, with minimum temperature of −4° C. being currently more preferred, and a minimum temperature between −4° C. and 0° C. being currently even more preferred.

Generally, the characteristics of a thermoprobe that is attached to the surface of the cooling device are the same as a thermoprobe that is attached to the treatment surface. The thermoprobe and its holder should be thin and small (e.g., having a diameter less than 2 mm, or, as is currently preferred, less than 1 mm) to allow for the thermocouple to be fixed at a well defined depth relative to the cooling surface of the element (e.g., within less than about one millimeter from the cooling surface). In a preferred embodiment, the thermocouple exhibits good thermal conductivity (i.e., similar to the thermal conductivity of water) in order to minimize inhibition of the cooling process. In one embodiment, the thermoprobe is embedded within the cooling surface of the cooling element.

The thermoprobe can be disposable (i.e., single-use) or it can be reusable, and, in either case, can be in communication with a handpiece or control unit of the cooling device. A non-limiting example of a disposable thermoprobe is a thermally-conductive plate.

In use, detecting a temperature increase can be delayed depending upon the location of the thermoprobe. Thus, a thermoprobe cooling plate can be utilized to determine a thermal gradient measurement. Assuming that the thermal conductivity of the thermoprobe is precisely known, this thermal gradient can be used to determine the heat flux into the cooling device according to various formulae/equations.

Heat conduction is defined as the transfer of heat from warm areas to cooler areas, and effectively occurs by diffusion. Thus, the heat flux $\Phi_Q$ is defined as:

$$\Phi_Q = \frac{[\text{heat per unit area}]}{[\text{escape time}]} \approx \frac{\rho C_P \Delta T d}{\frac{d^2}{\kappa}}, \quad (1)$$

where $\rho$ is the density, $C_P$ is the mass heat capacity in $$\frac{\text{erg}}{\text{g} \cdot \text{K}},$$

d is the diffusion distance, and $\kappa$ is the thermal diffusivity in $$\frac{\text{cm}^2}{\text{s}}.$$

$$\Phi_Q \approx \rho C_P \kappa \frac{\Delta T}{d} \quad (2)$$

Defining the thermal conductivity $$\left( \text{with units of } \frac{\text{erg}}{\text{cm} \cdot \text{K} \cdot \text{s}} \right)$$

$$k = \rho C_P \kappa \quad (3)$$

and noting that $$\frac{\Delta T}{d}$$

is the temperature gradient, this becomes Fourier's law $$\Phi_Q = k \nabla T. \quad (4)$$

These formulae/equations show that the temperature gradient between different positions within a thermoprobe cooling plate can be used to determine the heat removed by the cooling device. In addition, placement of thermoprobes can be used to monitor heat flow. Such data, in turn, can be used make other important determinations, e.g. deciding whether/when to provide an appropriate amount of heating to another body area for homeostasis of the body core temperature. The data can also be used to determine the appropriate amount of localized cooling for thermal damage of a specific volume of fatty tissue.

According to another exemplary embodiment of the present invention, a thermoprobe can be sited at a location away from the treatment site. Such a placement can be useful for a variety of purposes, including to monitor body core temperature or determine heat flow. Preferred remote localizations for placement of this type of "body core thermoprobe" are the tympanic membrane, sublingual, rectal or other remote skin surfaces. Among the currently preferred types of body core thermoprobes are an analog or digital thermocouple, a thermistor or a semiconductor thermometer.

Another suitable remote location for placement of a body core thermoprobe is the meatus *auricularis* externus. In accordance with such an embodiment, it is currently preferred to utilize—as a body core thermoprobe—a radiation measurement thermometer, which, optionally could also be combined with stereo headphones (or like devices) to be worn by a treatment subject in order to provide the subject with information (e.g., the remaining duration of the procedure, reminders regarding movement or lack thereof) and/or acoustic entertainment prior to or during the treatment.

It is useful to measure the body core temperature in order to ensure that the localized cooling does not cause a significant reduction in body core temperature, which could be accompanied by systemic side effects associated with hypothermia (e.g., cardiac arrhythmia, slowing down of metabolism, pain/discomfort caused by the general cold sensation). When a normal body core temperature is 37-38° C., any core temperature of 36° C. or lower could be indicative of the existence or onset of at least mild hypothermia, and thus should be sought to be avoided. Thus, if a body core temperature thermoprobe measures such a temperature, cooling should be discontinued, at least temporarily.

According to an alternate embodiment of the present invention, a body core thermoprobe may also be used to monitor external heat application in order to maintain a substantially constant body core temperature and to avoid a predetermined amount of temperature drop during the treatment process.

A thermoprobe also can be utilized to determine/monitor whether a cooling device is properly functioning. In such cases, currently preferred localizations for placement of the thermoprobe are within the tubing of a cooling agent or within a cooling agent reservoir, and preferred types of thermoprobes for such locations are a thermocouple, a thermistor, a semiconductor thermometer or a bimetallic thermometer. During use in such an embodiment, the thermoprobe gathers information to determine the temperature and/or temperature gradient within different locations of the cooling device. That data, in turn, indicates potential problematic conditions such as, e.g., lack of cooling agent, insufficient cooling temperature, failure of the cooling device, ice formation within the cooling agent, etc.

In addition to or instead of a thermoprobe, various other sensors can be placed in communication with the cooling device to monitor/verify proper functioning thereof. Suitable sensors include, but are not limited to, sensors for determining/monitoring the flow of cooling agent. By monitoring cooling agent flow, it is possible to determine, e.g., when/whether freezing of the cooling agent has occurred.

Another feedback system for monitoring/determining whether the cooling device is functioning properly is a sensor that measures the concentration of anti-freeze within the cooling agent. Among the sensors suitable for such a purpose are one or more optical sensors (which measure the optical density of the anti-freezing agent) and one or more sensors for detecting the density of the cooling agent and/or for determining the concentration of anti-freezing agent within the coolant agent.

Electrical feedback probes also can be utilized to provide feedback information in accordance with the present invention. Such probes can include bipolar probes, monopolar probes or a plurality of bipolar and/or monopolar probes. As described in various articles (see, e.g., D. M. Otten & B. Rubinsky, "Cryosurgical monitoring using bioimpedance measurements—a feasibility study for electrical impedance tomography," 47(10) *IEEE Trans. Biomed. Eng.* 1376-81 (October 2000); D. M. Otten et al., "Distributed network imaging and electrical impedance tomography of minimally invasive surgery," 3(2) *Technol. Cancer Res. Treat.* 125-34 (April 2004); A. Hartov et al., "Using multiple-electrode impedance measurements to monitor cryosurgery," 29(12) *Med. Phys.* 2806-14 (December 2002); A. A. Gage, "Correlation of electrical impedance and temperature in tissue during freezing," 16(1) *Cryobiology* 56-62 (1979)), electrical impedance measurements can be reliably utilized to monitor/determine the onset of freezing, the extent of freezing that has occurred within the skin, and/or the level of tissue damage that has occurred. It is currently preferred to site such electrical probes at the surface of the cooling device.

In an embodiment in which a plurality of electrical probes are utilized, it is possible to arrange such probes in a manner or an array to enable or otherwise facilitate three-dimensional imaging (e.g., by electrical impedance tomography (EIT)) of the phase transition within the dermis and the subcutaneous fatty tissue. At freezing temperatures, electrical impedance is typically markedly increased. Such information, in combination with electrical impedance imaging, can be used to determine if/when it is appropriate to either discontinue or decrease the cooling exposure. Such a determination is generally based on the onset of epidermal or dermal phase transition, which is representative of ice formation within aqueous tissue and which should be avoided lest the occurrence of unwanted side effects due to overtreatment.

Oscillating feedback probes (as described, e.g., in O. A. Lindahl et al., "A tactile sensor for detection of physical properties of human skin in vivo," 22(4) *J. Med. Eng. Technol.* 147-53 (July-August 1998)) also can be utilized to provide feedback information by monitoring the mechanical properties of the skin. Generally, such probes are utilized to detect changes in stiffness and elasticity of human skin that are related to age, environmental agents, day-to-day variations and application of cosmetics. However, such probes can also be easily combined with a cooling device of the present invention to assess/monitor skin stiffness. This is a useful determination, since at freezing temperatures the dermal stiffness becomes markedly increased, even to an extent whereby there can be undesired dermal ice formation. If the oscillating feedback probe senses increased dermal stiffness, the cooling treatment should be discontinued for an appropriate time.

An example of a suitable oscillating feedback probe is a spring loaded tactile sensor with displacement sensing capabilities that has been evaluated for non-invasive assessment of physical properties, stiffness and elasticity, of human skin in vivo. A tactile sensor of this type generally includes a piezoelectric vibrator (61 kHz) with a vibration pickup, electronics and programmable logic (e.g., a computer with software) for measurement of the change in frequency when the sensor is attached to an object. Integrated with the displacement sensor is a tactile sensor to show the compression of the spring that loads the sensor element against the object during measurement. Under certain conditions (e.g. fixed contact pressure) this change in frequency monitors the acoustic impedance of the object and is related to the stiffness of soft tissue.

It is also possible to implement ultrasound technology as a feedback device in accordance with the present invention. In practicing methods of the invention, cooling will reach the a proper depth, without causing damage the skin surface, such as the formation of so-called "ice balls" at freezing temperatures of the dermis. An ultrasound feedback device can detect (and provide feedback as to) the formation of an ice ball, thus indicating that the cooling regime should be modified or halted altogether in order to prevent initial/further damage to the skin. Ultrasound technology is also effective to detect and provide feedback information as to the onset of phase transition within the subcutaneous fatty tissue. Such an occurrence would also generally call for modifying treatment conditions or ending treatment entirely.

An exemplary device that can be utilized as an ultrasound feedback device in accordance with the present invention is described in P. Laugier et al., "In vivo results with a new device for ultrasonic monitoring of pig skin cryosurgery: the echographic cryoprobe," 111(2) *J. Invest. Dermatol.* 314-19 (August 1998). The device described therein is an echographic cryoprobe, which combines a high-frequency (20 MHz) miniature ultrasonic transducer and a cooling device. It is known that the mean value of ultrasound velocity of frozen skin is comparatively higher than that of non-frozen skin. Thus, such a device can be utilized to determine changes in ultrasound velocity that would be suggestive of echo formation preceding phase transitioning or freezing and/or the formation of an "ice ball" after freezing. In particular, an echographic cryoprobe enables in vivo real-time monitoring of depth penetration of an ice ball and provides feedback information relating to the rate of growth of the ice ball. Such detection can be automatic (i.e., operator-independent), and entails, in particular, detection of the echo signal from the freezing front and calculation of the depth penetration of the ice ball.

Figure 20:
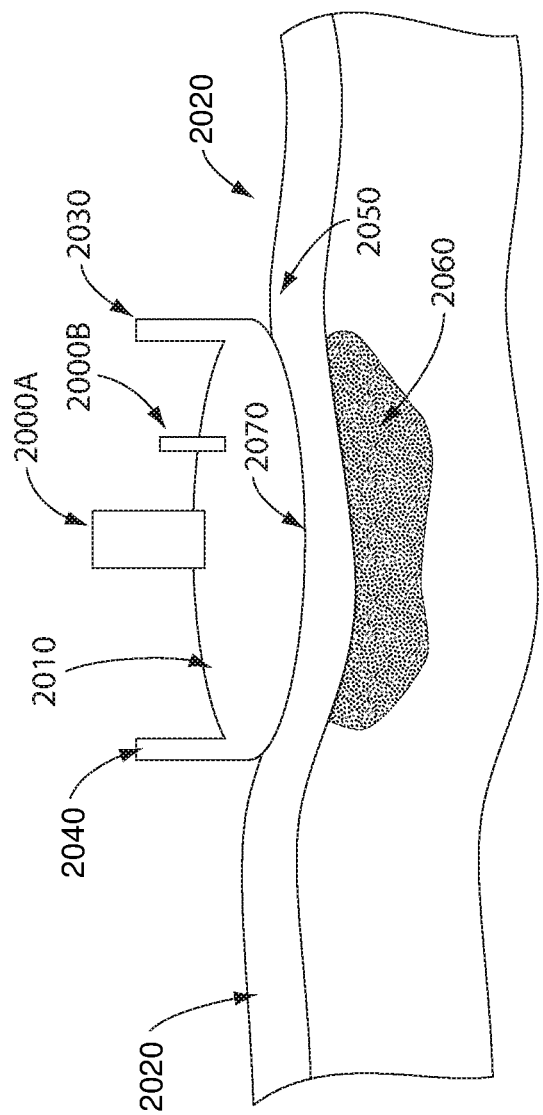
FIG. 20 depicts an exemplary embodiment of the present invention in which a cooling element is in communication with at least one feedback device.

FIG. 20 depicts an illustrative embodiment of the present invention in which an ultrasound-based feedback device 2000A is in communication with a cooling element 2010 during use of the cooling element at a treatment site 2020, which, in this embodiment is a patient's skin. An exemplary ultrasonic-based feedback device is an ultrasonic transducer, which, when employed, should have a diameter in the range of about 1 cm to 2 cm.

As shown in FIG. 20, the cooling element 2010 is in communication with the ultrasonic-based feedback device 2000A to allow for feedback to occur and also is contact with the skin 2020 to provide cooling thereto (e.g., by coolant being circulated into a coolant entry area 2030, through the cooling element, and, ultimately, out of the cooling element via coolant exit area 2040). The combination of the shape (e.g., convex) of the cooling element 2010 and the pressure exerted thereby causes the skin 2020 to compress such that the cooling element effects cooling of the dermis 2050 and, in turn, of the subcutaneous fat 2060 located beneath the dermis.

Optionally, but as is currently preferred, one or more objects or materials are placed at some or all of the interface surface 2070 between the cooling element 2010 and the skin 2020. By way of non-limiting example, a gel can be applied to the skin surface 2020, the cooling element 2010, or both. The gel should be thermally-conducting in order to improve the cooling effects of the cooling device, yet it also should be selected so as not to interfere with the gathering of feedback information. For example, in the embodiment depicted in FIG. 20, the gel should be ultrasound-transparent so as not to compromise the ability of the ultrasound transducer 2000A to obtain accurate measurements, and, in turn, to provide reliable feedback information.

Figure 21:
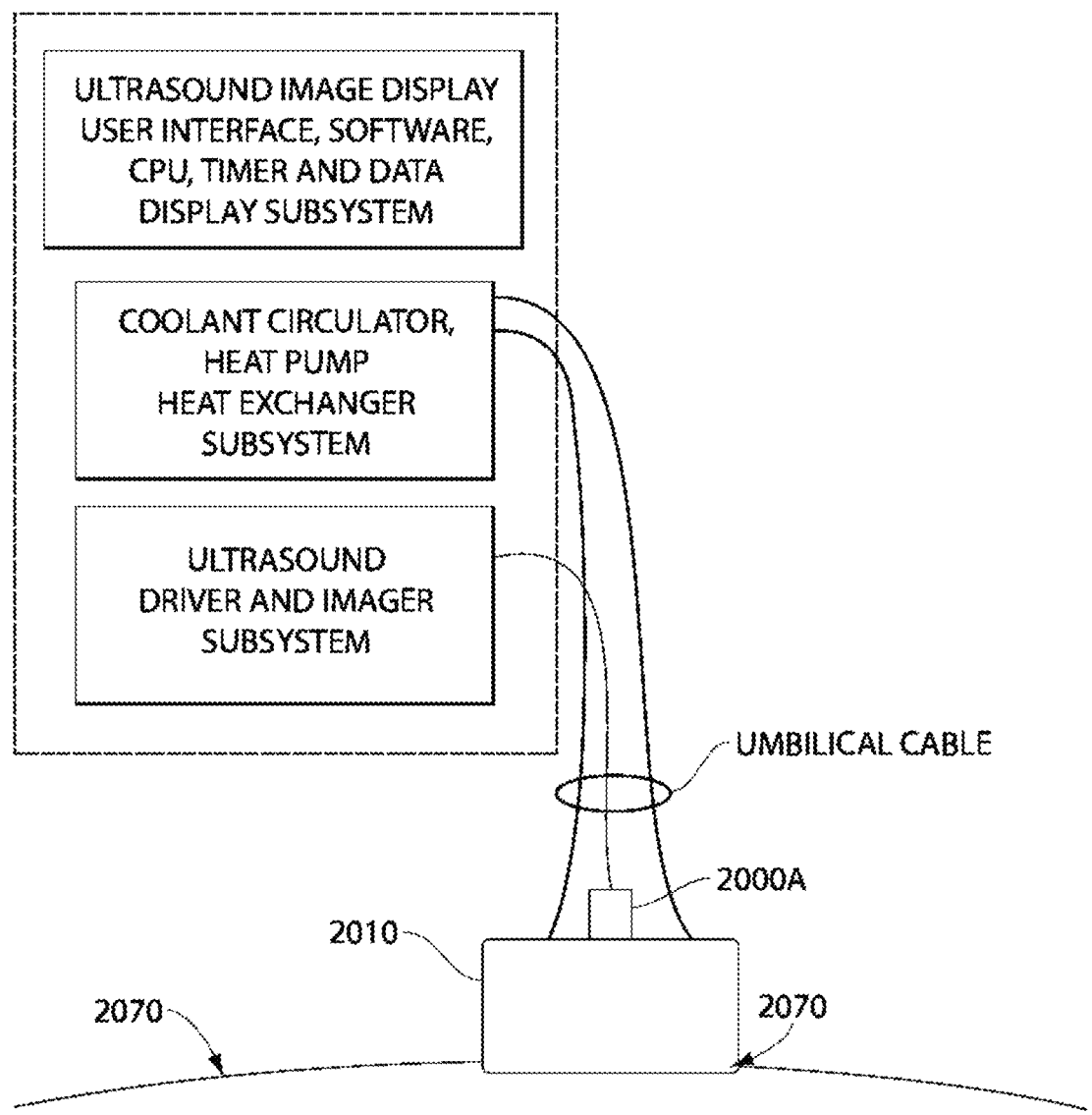
FIG. 21 is a schematic view of an exemplary embodiment of the present invention depicting the equipment with which the cooling element and/or the feedback device of FIG. 20 are connected in order to allow for feedback to occur.

The ultrasound transducer 2000A provides feedback information by gathering ultrasound data, which is passed along to and processed by other devices (shown schematically in FIG. 21) to which the ultrasonic transducer and/or the cooling element 2010 are connected.

It should be noted that the system depicted in FIG. 20 can include one or more additional feedback devices, such as a temperature sensor 2000B, in lieu of or in addition to feedback device 2000A. Such other feedback device(s) 2000B, if present, would be in communication with the cooling element 2010 and/or the treatment site 2020.

Another technique for gathering feedback is to utilize a combination of ultrasonic imaging and oscillating probes, such as sonoelastography and transient elastography. This technique is especially effective for determining the onset of ice formation within aqueous skin tissue by identifying phase transitions within different layers of skin. Such onset can signify an appropriate time to end a treatment cycle or it can indicate overtreatment prior to the end of a cycle.

Such combination devices define local tissue stiffness using Young's modulus, and, in particular, by characterizing the viscoelastic properties of soft tissues in different tissue layers and depths through investigation of their response to shear mechanical excitation. Because Young's modulus defines local tissue stiffness, it can be used to identify phase transitions within different layers of the skin. For example, and as described in J. L. Gennisson et al., "Assessment of elastic parameters of human skin using dynamic elastography," 51(8) *IEEE Trans. Ultrasonic Ferroelectric Freq. Control* 980-89 (August 2004), a high-resolution device with a spatial resolution sufficient to distinguish between dermal and fatty tissue layers can measure local Young's modulus in very thin layers (1-5 mm) in furtherance of in vivo evaluation of the elastic properties of human skin. The high-resolution device uses an ultrasonic probe (50 MHz) for tracking the displacements induced by a 300 Hz shear wave generated by a ring surrounding the transducer. The displacements are measured, e.g., through use of a cross-correlation technique between successive ultrasonic back-scattered echoes as would be known by one or ordinary skill in the art. The measurement technique described by Gennisson et al. was utilized to gather data in vivo on human forearms and was experimentally proven to be accurate for investigating elasticity in different skin-mimicking phantoms. The data showed that Young's modulus was higher in the dermis than in the hypodermis and other soft tissues.

For measuring the change in stiffness within the dermal and/or fatty tissue layers, ultrasound devices with a lower resolution and higher imaging depth can be employed.

Ultrasonic probes with frequencies in the range of between about 5 to about 30 MHz and more preferably, about 20 Mhz range are preferred.

In accordance with the present invention, the device described by Gennisson et al. can be combined with a cooling device of the present invention. As combined, the resulting device can be utilized to non-invasively determine phase transitions in different tissue layers, thus replacing less accurate/reliable current techniques (e.g., subjective palpation by an experienced observer.

Other techniques can also be utilized to determine phase transitions in accordance with the present invention, wherein such techniques include, but are not limited to optical coherence tomography and magnetic resonance imaging (MRI).

Yet another feedback technique pertains to the use of one or more probes to measure sound velocity in tissue. Acoustic velocity within tissue is temperature dependent, and increases significantly at lower temperatures. Acoustic velocity can be measured, e.g., by time-of-flight measurements as described in A. Mulet et al., "Ultrasonic velocity in cheddar cheese as affected by temperature," 64(6) *J. Food Sci.* 1038-41 (1999), wherein a 1 MHz narrow band ultrasonic transducer is utilized to measure the time of flight within an oscilloscope within a certain path length. These probes can be used to monitor temperature and phase transitions within the different layers of the skin. Onset of epidermal or dermal phase transition, which represents ice formation within aqueous tissue, should be avoided by discontinuing or reducing the cold exposure, at least temporarily. Onset of phase transition within the fatty tissue can be used as an endpoint to monitor effective cold exposure regimen.

Another technique that can be employed to detect ice crystal formation within the epidermis or dermis is IR-reflectoscopy. Skin is relatively transparent in the range from about 800 to about 1400 nm, which is part of the so called "optical window" of skin. In particular within the range from about 1000 to about 1400 nm, the skin has absorbing chromophores and scattering is thus limited. Thus, any kind/amount of ice crystal formation will cause a significant increase in reflective capacity.

In accordance with an exemplary IR-reflectoscopy embodiment of the present invention, a wavelength having a penetration depth into the skin which corresponds to the thickness of the dermis (e.g., about 2-4 mm) is applied, such that any increase of optical reflectance can be measured/detected due to ice crystal formation within the epidermis or dermis. The range of wavelengths used for determination of crystal formation within the dermis is therefore preferably in the range of about 400 to about 800 nm. For a wavelength of about 700 to about 800 nm, there is relatively little absorption by the blood and therefore, changes of perfusion during exposure do not affect the measurements.

For deeper penetrating wavelengths (e.g. about 1000 to about 1300 nm), the changes in reflective capacity can be caused by crystal formation in either the epidermis, dermis or subcutaneous fatty tissue. In one embodiment, the location of crystal formation can be determined by the measured change in maximum reflection wavelength, which will vary according to the characteristic morphology of the ice crystals within a particular tissue layer. In another embodiment, the location of crystal formation can be determined by considering the distance between the emitter and the detector. There is a maximum increase in signal upon crystal formation at different depths. For crystal formation at the epidermis and dermis, wherein the maximum increase of reflection occurs with an emitter-detector distance of approximately 1 mm. For subcutaneous crystal formation, the maximum increase of reflection occurs with an emitter-detector distance of approximately 3-5 mm.

In one embodiment, diffuse optical tomography can be applied to monitor the spatially diffuse spectrum of reflectance emitted from one or more tissues under observation (e.g., dermis, epidermis or subcutaneous adipose tissue). Methods of diffuse optical tomography are well known in the art, and can be carried out in accordance with standard practices.

Feedback information also can be provided in accordance with the present invention through the use of one or more optical probes, which measure, e.g., the blood content or blood flow within the dermis. For example, optical reflectroscopy can further be employed to monitor blood flow and therefore, to determine the contact pressure necessary to decrease local blood flow. Laser Doppler techniques and equipment can also be utilized to separately quantify the two components of blood flow, namely microvascular volume and red blood cell velocity. Data regarding blood flow and the microvascular volume, in turn, can be used to gauge the extent and/or sufficiency of contact pressure being exerted by the cooling device onto the treatment surface. Use of one or more such optical probes allows for decreased or ceased blood flow, which facilitates or enables cooling of deeper skin layers. An optical probe also can utilized to indicate whitening of the treatment surface, which is suggestive of the formation of unwanted ice crystals within the dermis and epidermis.

Another form of obtaining feedback information in accordance with the invention is to determine/monitor whether there is appropriate contact between the cooling device and the treatment surface. This can be a useful determination, since even if the cooling device is operating at the proper temperature, the proper level of cooling will not be achieved at the cooling surface unless appropriate contact exists.

Contact probes monitor the thermal contact with the skin surface and can provide a signal to a central control unit when the cooling device is in proper contact with the skin. Various methods can be used to monitor contact of the cooling element with the skin including, but not limited to, one or more electrical switches within the cooling element or at the edge/frame of the cooling element, one or more pressure sensors, a thermoprobe at the interface between a cooling probe and the skin (wherein the thermoprobe acts as a contact sensor as thermal contact provides a temperature rise), electrical resistance between two electrodes positioned at the edge of the cooling element, and one or more optical sensors to detect placement of the cooling device in contact with the skin.

In an embodiment of the present invention, wherein the contact probe is one or more pressure probes, the purpose of the pressure probe(s) is to monitor whether sufficient pressure is being applied onto the treatment surface by the cooling device. An exemplary pressure probe is a spring loaded cooling element, wherein the elongation of the spring is detected by a position detector and determines (along with the spring constant) the force/pressure that is being applied to the skin surface. Optionally, one or more feedback devices can be provided to measure vacuum levels, wherein it is currently preferred that the vacuum level be above zero pressure but also that the level not rise above approximately one-half atmospheric pressure (i.e., not above 500 millibars).

Still yet another technique for providing feedback is through measurement of the phase transition within the epidermis, dermis and/or subcutaneous fat. It is currently preferred to utilize such a technique in connection with an embodiment in which skin is being cooled while folded. This technique can be accomplished, by way of non-limiting example, by employing a detector and mechanical pulse emitter. The detector and emitter should be spaced apart from each other according to the depth level that is to be measured, wherein the detector and emitter are generally spaced farther apart in order to measure comparatively deeper levels. For example, the spacing between the detector and the emitter is generally in the range of about 0.1 mm to about 5.0 mm (with a spacing of 0.1 mm to about 1.0 mm being currently preferred) in order to measure the phase transition within the epidermis or dermis, whereas the spacing between the detector and the emitter is generally in the range of about 1.0 mm to about 15.0 mm (with a spacing of 5.0 mm to about 10 mm being currently preferred) in order to measure the phase transition within the subcutaneous fat.

The various feedback devices described herein can be utilized invasively as well. Invasive measurement can provide more accurate data under certain circumstances, and thus can be preferable under such circumstances. This is especially the case where conditions exist in which the normal drawbacks (e.g., pain, discomfort) relating to the use of invasive devices are not present. For example, if for some reason a treatment subject is under general anesthesia during the treatment process, then it might be preferable to utilize an invasive feedback device, since the treatment subject will not sense added pain and because more accurate readings could be obtained.

Instead of or in addition to the devices described above, feedback information can be provided by medical personnel, by one or more other persons involved in the treatment process, and/or by the treatment subject itself. Among the actions that can be taken by such personnel are shutting down the system, modifying one or more operating conditions or parameters, and/or limiting further temperature decrease. Such actions can be effected by adjustment to the central cooling unit, e.g., via remote control. This remote control can be in communication with the central cooling control unit via wired or wireless connection to the central cooling unit.

The treatment subject, medical personnel, or one or more other persons involved in the treatment process also can be entrusted to monitor the various process to determine the occurrence of certain observational side effects (i.e., side effects that cannot be readily gauged by devices). Such observational side effects include, but are not limited to pain, discomfort, fear, apprehension or nausea.

Substantial cooling of the subcutaneous adipose layer, for example to a target temperature between about −5° C. and 15° C., by cooling at the skin surface has several requirements. Heat extracted from the skin surface establishes a temperature gradient within the skin, which in turn cools first the epidermis, dermis, and finally subcutaneous adipose layers. Dermal blood flow brings heat from the body core to the dermis. Dermal blood flow can therefore severely limit cooling of the deep dermis and subcutaneous adipose. Therefore, it is preferred to temporarily limit or eliminate cutaneous blood flow, for example by locally applying a pressure to the skin greater than the systolic blood pressure, while cooling as a treatment to achieve reduction in subcutaneous adipose. Local pressure can be applied and controlled by a flexible substance, such as a garment or bandage, that is or can be adjusted to surround the treatment site or an area in close proximity to the treatment site. The garment can be constricted, e.g., drawn tighter, or loosened in intervals, or as otherwise desired, to modulate pressure during treatment.

In one embodiment, the flexible substance (e.g., garment) is comprised of a pattern, such as a mesh pattern, that mediates the application of heterogeneous pressure to the application site in order to effectively suppress superficial blood flow, which will enhance cooling efficacy as well as readings obtained from the various feedback devices of the invention. The pattern of localized compression can depend on, for example, skin stiffness and the anatomy of the dermal blood supply. In one embodiment, the optimum diameter is between about 2 to about 5 times the thickness of the dermis, or about to 2 to about 15 mm.

The diameter of the individual filaments of the flexible substance is selected such that the applied pressure does not cause damage (e.g. cutting, epidermal necrosis). In one embodiment, the optimum filament diameter is about 1 to about 3 mm. Individual filaments of the garment may have projections with a preset spring constant for angle deformation, which is set such that the localized pressure to the skin is controlled. Filaments within the treatment area can comprise hollow tubular structures having a cooling agent circulating within (e.g. liquid, gas). The filaments can also contain a temperature measurement element (e.g. thermocouple, wire) to monitor the surface temperature closely within individual micro-treatment sites. The flexible substance (e.g., garment) can further comprise a temperature sensitive color scale, which indicates by specific colors the efficacy or other effects of the treatment methods. In another embodiment, the flexible substance (e.g., garment) is applied such that mechanical movement is provided at the application site, thereby enhancing disruption of the adipose tissue.

A general requirement is that the time of cooling at the skin surface must be long enough to allow heat to flow from the dermis and subcutaneous adipose layers in order to achieve the desired temperature for treatment of the same. When the subcutaneous adipose is cooled to a temperature below that for crystallization of its lipids, the latent heat of freezing for these lipids must also be removed, by diffusion. The skin surface cooling temperature and cooling time can be adjusted to control depth of treatment, for example the anatomical depth to which subcutaneous adipose is affected. Heat diffusion is a passive process, and the body core temperature is nearly always close to 37° C. Therefore, another general requirement is that the skin surface temperature during cooling, must be lower than the desired target (e.g., adipocytes) temperature for treatment of the region, for at least part of the time during which cooling is performed. When cooling a diameter of skin greater than about 2 cm, and with no blood flow, one-dimensional heat diffusion offers a good approximation for estimating temperature profiles in skin over time during cooling. Heat diffusion is governed by the general diffusion equation, $\delta T/\delta t = \kappa \delta^2 T/\delta z^2$, where T (z,t) is the temperature in skin as a function of depth z and time t, and $\kappa$ is the thermal diffusivity, which is approximately $1.3 \times 10^{-3}$ cm$^2$s$^{-1}$ for skin tissue. Solutions and approximate solutions to the heat diffusion equation have been made for planar geometry of a semi-infinite slab, approximating the situation for skin. When the surface of the skin (z=0) is held at a given lower temperature, a useful approximation is that heat flow from a depth z requires a time of approximately $t \approx z^2$ to achieve a temperature difference ½ of the initial difference, where t is in seconds and z is in millimeters. Thus, $z^2$ can be considered an approximate value for a thermal time constant. For example, if the initial skin temperature is 30° C., and ice at 0° C. is placed firmly against the skin surface, it requires about 1 second for the temperature at a depth of 1 millimeter, to reach about 15° C. The subcutaneous fat layer typically begins at about z≅3 mm, and extends for millimeters up to many centimeters thick. The thermal time constant for heat transfer from the top of the subcutaneous adipose layer is therefore about 10 seconds. To achieve substantial cooling of subcutaneous adipose, at least several and preferably greater than 10 thermal time constants of cooling time are required. Therefore, cooling must be maintained for about 30-100 seconds at the skin surface, and in the absence of dermal blood flow, for the temperature of the topmost portion of subcutaneous adipose to approach that of the cooled skin surface. The latent heat of crystallization for lipids, mentioned above, must also be removed when the fat temperature drops below that for crystallization. Therefore in general, cooling times over 1 minute are desired, and cooling times greater than about 1 minute can be used to adjust the depth of adipocytes affected, for times up to more than an hour.

Accordingly, in yet another embodiment, the dermis is cooled at a rate sufficient to induce vasoconstriction. Blood circulation within the dermis stabilizes the temperature of the dermis close to body temperature. In order to cool subcutaneous adipose tissue to temperatures below body temperature, blood flow can be minimized. Fast cooling of the epidermal surface can achieve reflectory vasoconstriction that limits blood circulation in an appropriate way.

In yet another embodiment, a vasoconstrictive drug is administered to induce vasoconstriction. Vasoconstrictive drugs, for example, can be topically applied at the point of contact either before, after or during application of the cooling agent. Where necessary, systemic administration of the vasoconstrictive drug can be provided through conventional methods, such as injection or oral administration. The vasoconstrictive drug can be any known in the art. Preferably, the vasoconstrictive drug is EMLA cream or epinephrine.

In yet another embodiment, pressure is applied to a surface, either at the point of contact with the cooling agent or in proximity thereto, such that lateral blood flow is limited. Pressure can be applied, for example, to a skin surface by compressing the skin surface into a skin fold comprising single or multiple folds. Pressure can also be by applying a vacuum either at the point of contact with the cooling agent or in proximity thereto.

Without being bound by theory, it is believed that the rate of formation of crystals in lipid-rich cells can be altered by the application of pressure during the cooling process. Sudden crystallization, rather than a slow accumulation of crystals, would cause greater damage to the lipid-rich cells. It is also believed that the application of pressure can force the movement of the crystals within the lipid-rich cells, enhancing the damage to the bilayer membrane. Furthermore, different compartments of the subcutaneous adipose tissue have different viscosities. In general, the viscosity is enhanced at colder temperatures (e.g., those particularly close to the point of phase change). Because the phase change for lipid-rich cells occurs at higher temperatures than non lipid-rich cells, non-uniform tension lines form within the subcutaneous adipose tissue upon the application of pressure. It is believed that pronounced damage occurs within these tension lines.

In yet another aspect, the temperature of the dermis and/or epidermis oscillates between 35° C. and −15° C. More preferably, the temperature of the dermis and/or epidermis oscillates between −10° C. and 10° C. Even more preferably, the temperature of the dermis and/or epidermis oscillates between −8° C. and 8° C. Oscillating temperatures at the skin surface can provide intermittent warming to counteract potential side effects of the cooling process (e.g., crystal formation in the dermal or epidermal cells).

In yet another aspect, application of the cooling agent is coupled with the application of electric or acoustic fields, either constant or oscillating in time, localized in the dermis and/or epidermis to reduce or eliminate crystal formation therein.

FIG. 1A illustrates a treatment system 100 for cooling a target area in accordance with an embodiment of the invention. As shown in FIG. 1A, treatment system 100 may include a control unit 105 and a treatment unit 107, which may include a cooling/heating element 110 and a treatment interface 115.

Control unit 105 may include a power supply, for example, control unit may be coupled to a power source, for supplying power to treatment unit 107. Control unit 105 can also include a computing device having control hardware and/or software for controlling, based on inputted properties and/or parameters, cooling/heating element 110 and treatment interface 115. Treatment interface 115 can include a detector 120.

Figure 1B:
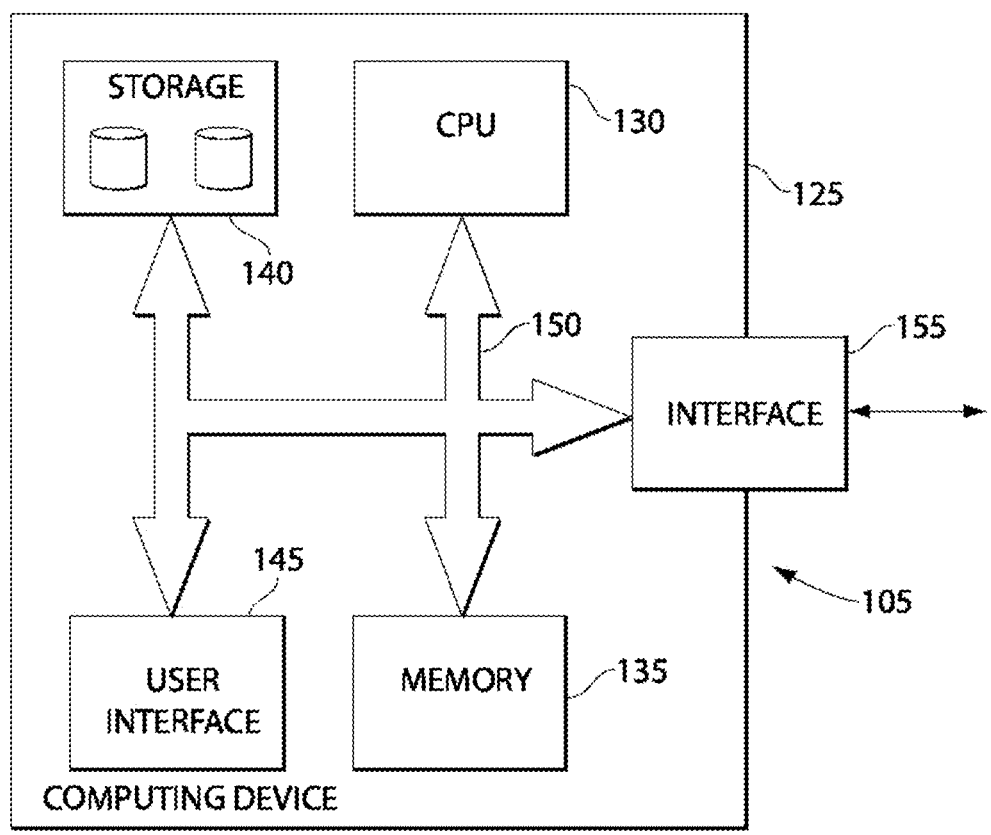
FIG. 1B depicts a diagram illustrating a configuration of control unit.

FIG. 1B is a diagram illustrating a configuration of control unit 105 in accordance with an embodiment of the invention. As shown in FIG. 1B, control unit 105 can comprise a computing device 125, which can be a general purpose computer (such as a PC), workstation, mainframe computer system, and so forth. Computing device 125 can include a processor device (or central processing unit "CPU") 130, a memory device 135, a storage device 140, a user interface 145, a system bus 150, and a communication interface 155. CPU 130 can be any type of processing device for carrying out instructions, processing data, and so forth. Memory device 135 can be any type of memory device including any one or more of random access memory ("RAM"), read-only memory ("ROM"), Flash memory, Electrically Erasable Programmable Read Only Memory ("EEPROM"), and so forth. Storage device 140 can be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). Storage device 140 can also include a controller/interface (not shown) for connecting to system bus 150. Thus, memory device 135 and storage device 140 are suitable for storing data as well as instructions for programmed processes for execution on CPU 130. User interface 145 may include a touch screen, control panel, keyboard, keypad, display or any other type of interface, which can be connected to system bus 150 through a corresponding input/output device interface/adapter (not shown). Communication interface 155 may be adapted to communicate with any type of external device, including treatment unit 107. Communication interface 155 may further be adapted to communicate with any system or network (not shown), such as one or more computing devices on a local area network ("LAN"), wide area network ("WAN"), the internet, and so forth. Interface 155 may be connected directly to system bus 150, or can be connected through a suitable interface (not shown). Control unit 105 can, thus, provide for executing processes, by itself and/or in cooperation with one or more additional devices, that may include algorithms for controlling treatment unit 107 in accordance with the present invention. Control unit 105 may be programmed or instructed to perform these processes according to any communication protocol, programming language on any platform. Thus, the processes may be embodied in data as well as instructions stored in memory device 135 and/or storage device 140 or received at interface 155 and/or user interface 145 for execution on CPU 130.

Referring back to FIG. 1A, treatment unit 107 may be a handheld device, an automated apparatus, and the like. Cooling/heating element 110 can include any type of cooling/heating component, such as a thermoelectric cooler and the like.

Figure 1C:
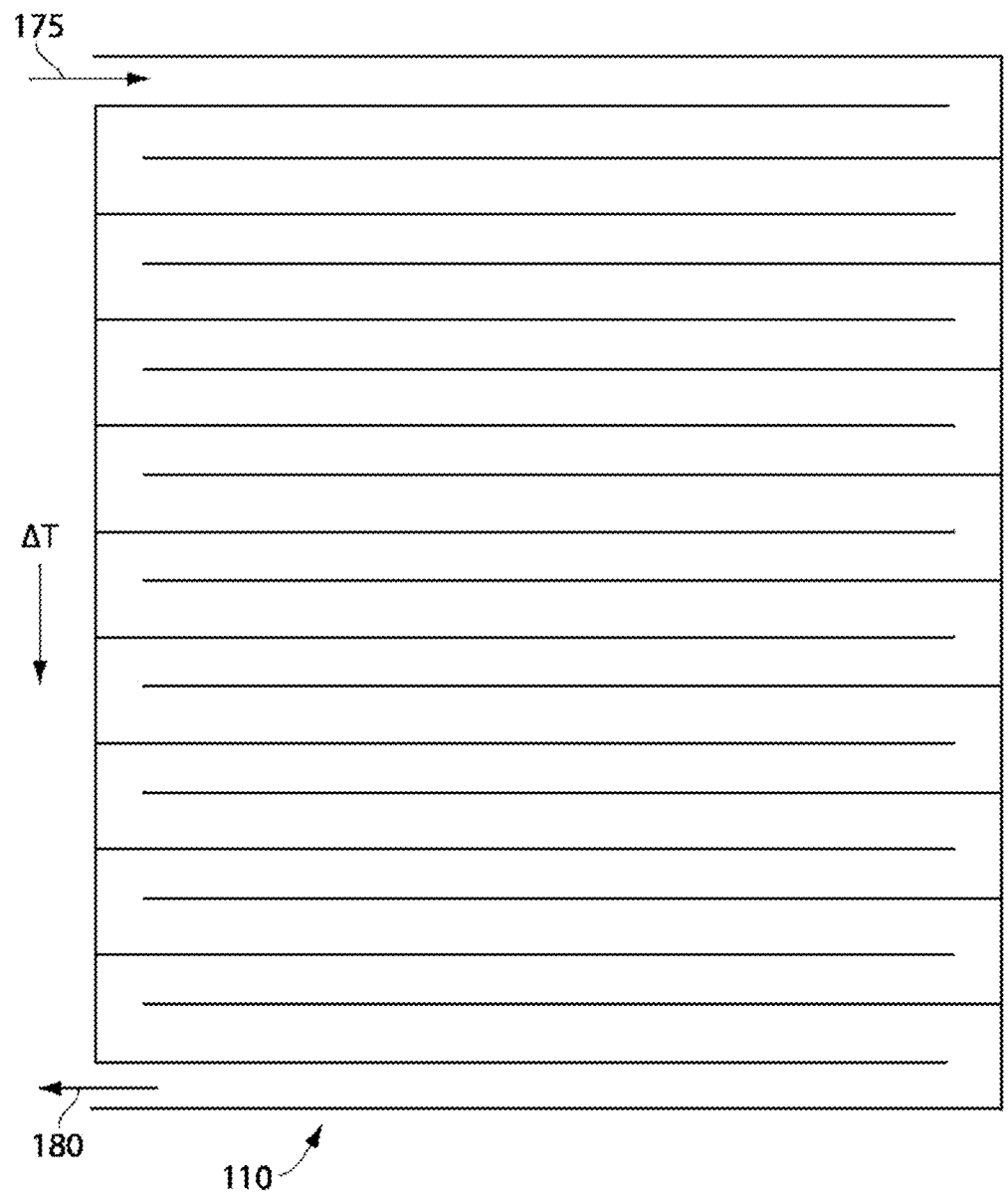
FIG. 1C depicts a diagram showing cooling/heating element.

FIG. 1C is a diagram showing cooling/heating element 110 in accordance with an embodiment with the present invention. As shown in FIG. 1C, cooling/heating element 110 can include a network of passages where a cooling/heating fluid flows through. The passages may be formed by any heat conducting tubing and the like. The cooling/heating fluid can be directed into element 110 through an input 175 and expelled through an output 180. The cooling/heating fluid may be any fluid having a controlled temperature, such as cooled air/gas or liquid. For example, a saltwater or acetone bath that is cooled using ice or frozen carbon dioxide may be used as a source of cooled liquid pumped through element 110. A circulating system may, thus, be formed where fluid expelled at output 180 is re-cooled at the fluid source and re-directed into input 175. The temperature of the fluid source and/or element 110, which may include the rate at which cooling fluid is pumped through element 110, can be monitored and controlled by control unit 105. Thus, the temperature of cooling/heating element 110 can be controlled or programmed using control unit 105. As further shown in FIG. 1C, there can be a temperature difference, ΔT, between regions of element 110. For example, heat from the target tissue may be transferred to the cooling fluid during treatment causing fluid near output 180 to have a higher temperature than the cooling fluid near input 175. Such ΔT may be reduced by reducing the size of element 110. In accordance with an embodiment of the invention, the configuration of the passages in element 110 and the corresponding application of element 110 to target tissue can account for any difference in temperature needed for treating various tissue targets. For example, the region of element 110 near exit 180 can be applied to treatment areas requiring a higher treatment temperature, and so forth. The passages of element 110 can, thus, be configured in accordance with the size, shape, formation, and so forth, of target tissue that require the various treatment temperatures. Cooling/heating fluid can also be pumped through element 110 in a pulsing manner.

Referring back to FIG. 1A, treatment interface 115 can be any type of interface between cooling/heating element 110 and the epidermis 160 for effecting treatment onto the epidermis 160, dermis 165 and fat cells 170. For example, treatment interface 115 may include a cooling (conductive) plate, a cooling fluid-filled vessel, a free-forming membrane (for a complementary interface with an uneven epidermis), a convex cooling element (for example, as shown in FIG. 3), and the like. Preferably, treatment interface 115 comprises a heat conducting material that complements the epidermis 160 for maximum heat transfer between cooling/heating element 110 and the epidermis 160, dermis 165 and/or fat cells 170. For example, treatment interface 115 can be a fluid-filled vessel or a membrane so that the change in pressure from cooling element 110 caused by a pulsing flow of cooling fluid may be transferred to the target tissue. Furthermore, treatment interface 115 may simply be a chamber where cooling/heating fluid may be applied directly to the target tissue (epidermis 160, dermis and fat cells 170), for example by using a spraying device and the like.

Detector 120 can be a temperature monitor, for example, a thermocouple, a thermistor, and the like. Detector 120 may include any thermocouple type, including Types T, E, J, K, G, C, D, R, S, B, for monitoring tissue cooling. Detector 120 may also include a thermistor, which can comprise thermally-sensitive resistors whose resistances change with a change in temperature. The use of thermistors may be particularly advantageous because of their sensitivity. In accordance with an embodiment of the invention, a thermistor with a large negative temperature coefficient of resistance ("NTC") can be used. Preferably, a thermistor used for detector 120 may have a working temperature range inclusive of about −15° C. to 40° C. Furthermore, detector 120 can include a thermistor with active elements of polymers or ceramics. A ceramic thermistor may be most preferable as these can have the most reproducible temperature measurements. A thermistor used for detector 120 can be encapsulated in a protective material such as glass. Of course, various other temperature-monitoring devices can also be used as dictated by the size, geometry, and temperature resolution desired. Detector 120 can also comprise an electrode which can be used to measure the electrical resistance of the skin surface area. Ice formation within superficial skin structures like the epidermis or dermis causes an increased electrical resistance. This effect can be used to monitor ice formation within the dermis. Detector 120 can further consist of a combination of several measurement methods.

Detector 120 can, thus, extract, inter alia, temperature information from the epidermis 160, dermis 165 and/or fat cells 170 as feedback to control unit 105. The detected temperature information can be analyzed by control unit 105 based on inputted properties and/or parameters. For example, the temperature of fat cells 170 may be determined by calculation based on the temperature of the epidermis 160 detected by detector 120. Thus, treatment system 100 may non-invasively measure the temperature of fat cells 170. This information may then be used by control unit 105 for continuous feedback control of treatment unit 107, for example, by adjusting the energy/temperature of cooling/heating element 110 and treatment interface 115, thus maintaining optimal treatment temperature of target fat cells 170 while leaving surrounding epidermis 160 and dermis 165 intact. As described above, the cooling/heating element 110 can provide adjustable temperatures in the range of about −10° C. up to 42° C. An automated temperature measurement and control sequence can be repeated to maintain such temperature ranges until a procedure is complete.

It is noted that adipose tissue reduction by cooling lipid-rich cells may be even more effective when tissue cooling is accompanied by physical manipulation, for example, massaging, of the target tissue. In accordance with an embodiment of the present invention, treatment unit 107 can include a tissue massaging device, such as a vibrating device and the like. Alternatively a piezoelectric transducer can be used within treatment unit 107 in order to provide mechanical oscillation or movement of the cooling/heating element 107. Detector 120 can include feedback devices for detecting changes in skin viscosity to monitor the effectiveness of treatment and/or to prevent any damage to surrounding tissue. For example, a vibration detecting device can be used to detect any change in the resonant frequency of the target tissue (or surrounding tissue), which can indicate a change in tissue viscosity, being mechanically moved or vibrated by a vibrating device contained in treatment unit 107.

To further ensure that the epidermis 160 and/or the dermis 165 is not damaged by cooling treatment, an optical detector/feedback device can be used to monitor the change of optical properties of the epidermis (enhanced scattering if ice formations occur); an electrical feedback device can be used to monitor the change of electric impedance of the epidermis caused by ice formation in the epidermis; and/or an ultrasound feedback device may be used for monitoring ice formation (actually to avoid) in the skin. Any such device may include signaling control unit 105 to stop or adjust treatment to prevent skin damage.

In accordance with an embodiment of the invention, treatment system 100 may include a number of configurations and instruments. Algorithms that are designed for different types of procedures, configurations and/or instruments may be included for control unit 105.

Figure 1D:
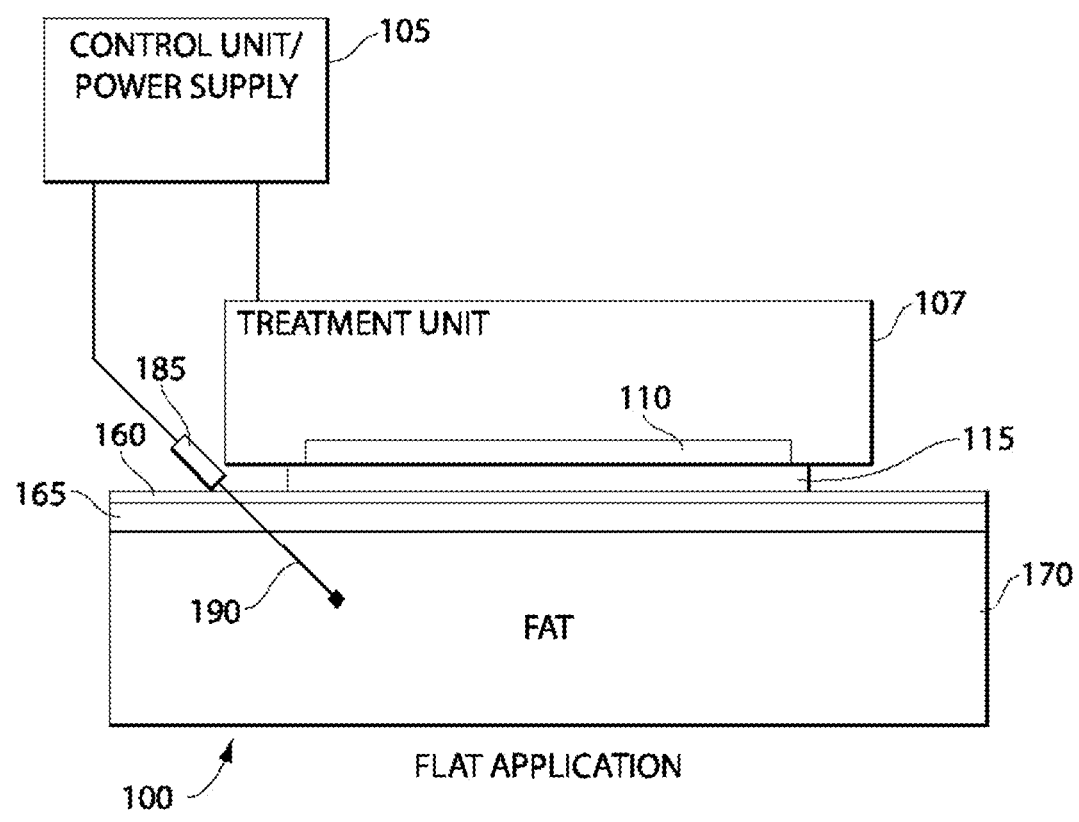
FIG. 1D illustrates a flat cooling treatment system with a probe controller.

As shown in FIG. 1D, treatment system 100 may include a probe controller 175 and a probe 180 for minimal invasive temperature measurement of fat cells 170. Advantageously, probe 180 may be capable of measuring a more accurate temperature of fat cells 170, thereby improving the control of treatment unit 107 and the effectiveness of treatment.

It is noted that treatment system 100 may be controlled remotely. For example, the link between control unit 105 and treatment unit 107 may be a remote link (wired or wireless) providing control unit 105 remote control over cooling/heating element 110, treatment interface 115, probe controller 175, and probe 180.

While the above exemplary treatment system 100 is illustrative of the basic components of a system suitable for use with the present invention, the architecture shown should not be considered limiting since many variations of the hardware configuration are possible without departing from the present invention.

Figure 2A:
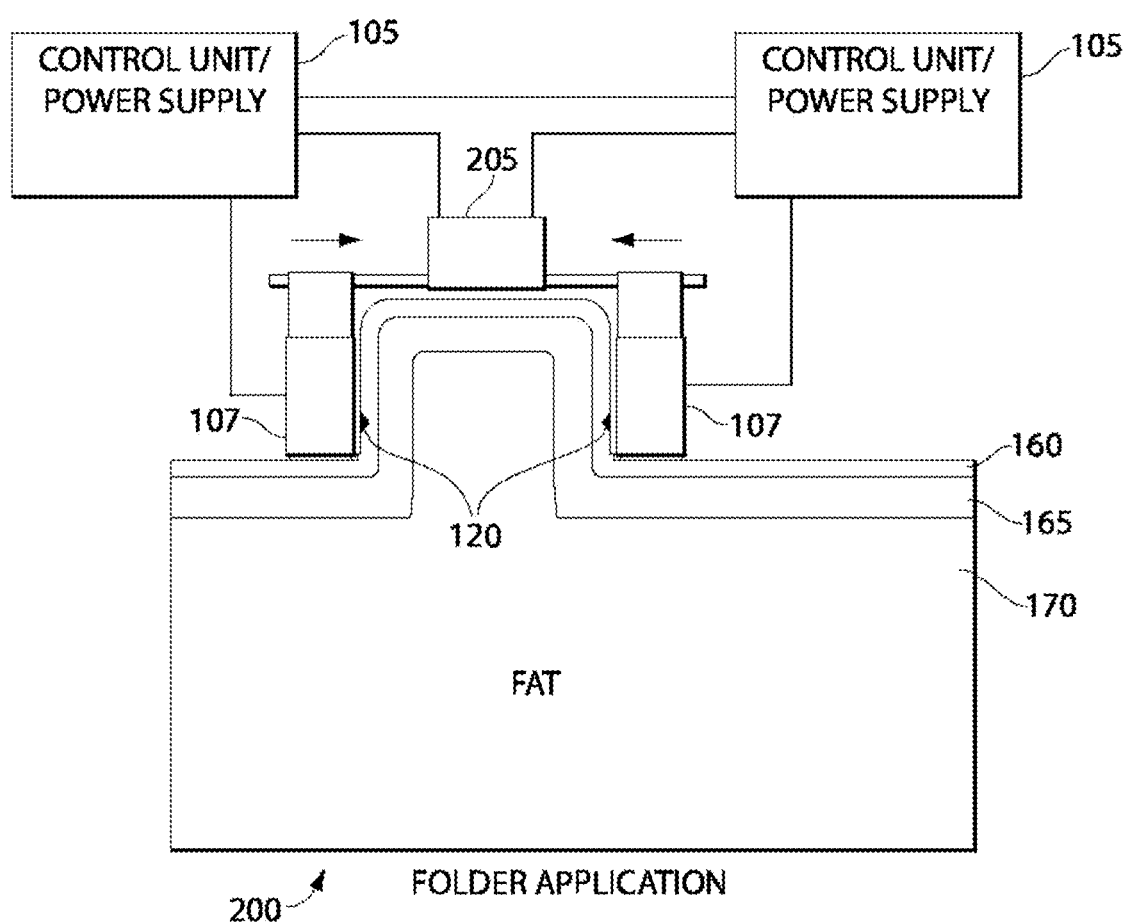
FIG. 2A illustrates a treatment system for cooling lipid-rich cells within a skin fold.

FIG. 2A illustrates a treatment system 200 for cooling fat cells 170 by folding the target tissue in accordance with an embodiment of the invention. As shown in FIG. 2A, treatment system 200 may include corresponding control units 105 and treatment units 107 on two sides coupled to a compression unit 205. Compression unit 205 may be adapted to pull treatment units 107 together, thereby folding (or "pinching") target tissue (epidermis 160, dermis 165 and fat cells 170) up between treatment units 107. The treatment interface 115 of the respective treatment units 107 on either side of the target tissue may thus cool fat cells 170 from multiple sides with greater effectiveness, as described above. Detectors 120 can be included to measure and monitor the temperature of the target tissue. As shown in FIG. 2A, control units 105 may be connected to form an integrated system. In accordance with an embodiment of the present invention, the various components of system 200 may be controlled using any number of control unit(s).

As described before, physical manipulation of target tissue may improve the effectiveness of cooling treatment. In accordance with an embodiment of the present invention, compression unit 205 may vary the force with which treatment units 107 are pulled together around the target tissue (epidermis 160, dermis 165 and fat cells 170). For example, compression unit 205 can apply a pulsing force for alternately tightening and loosening the fold (or "pinch") of the target tissue. Resistance to the tightening can further be monitored for detecting any changes in the characteristics (for example, the viscosity) of the target tissue, and thus ensuring the effectiveness and safety of the treatment.

Figure 2B:
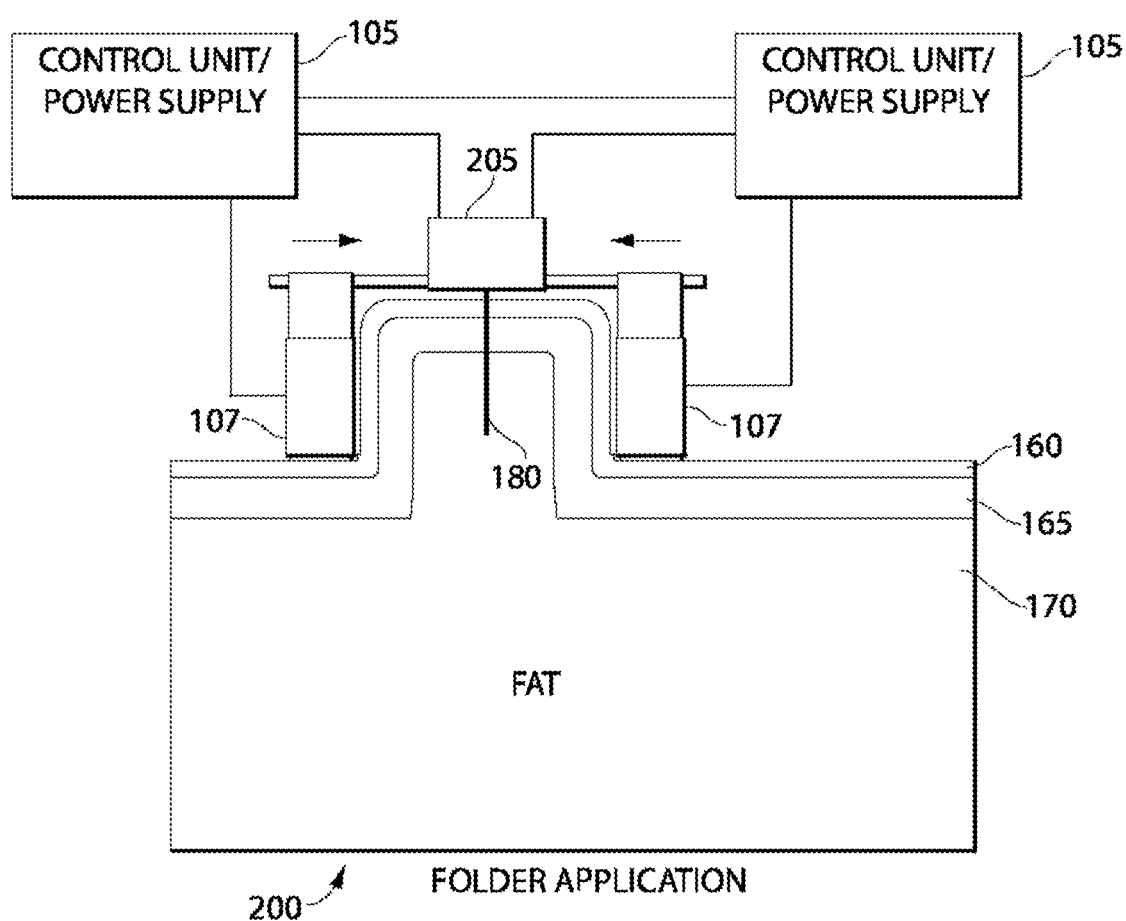
FIG. 2B illustrates a treatment system for cooling lipid-rich cells within a skin fold with a probe controller.

FIG. 2B illustrates system 200 with a probe 180 similar to that of system 100 shown in FIG. 1C for minimal invasive temperature measurement of fat cells 170. As described above, probe 180 may be capable of measuring a more accurate temperature of fat cells 170, thereby improving the control of treatment unit 107 and the effectiveness of treatment.

Figure 3A:
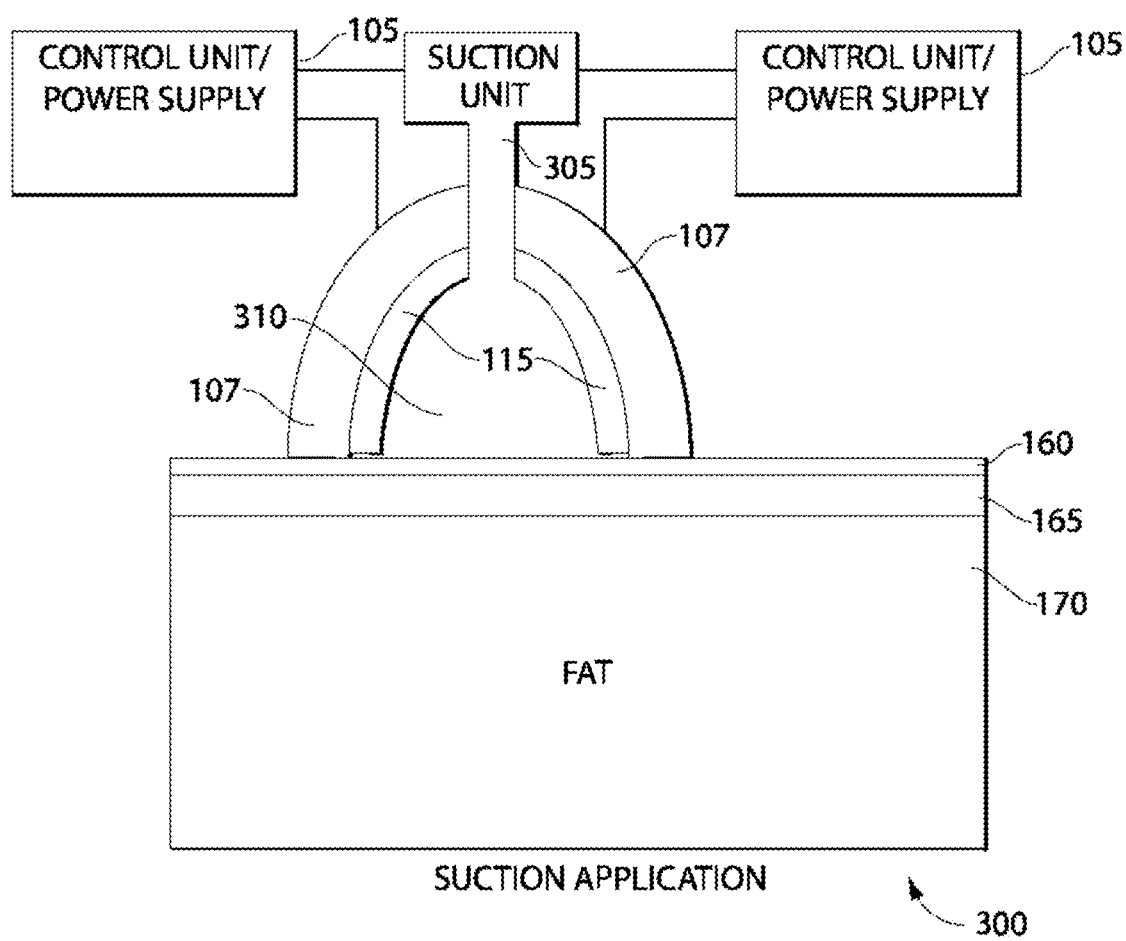
FIG. 3A illustrates a treatment system that includes a suction unit, FIG. 3B also illustrates a treatment system that includes a suction unit.
Figure 3B:
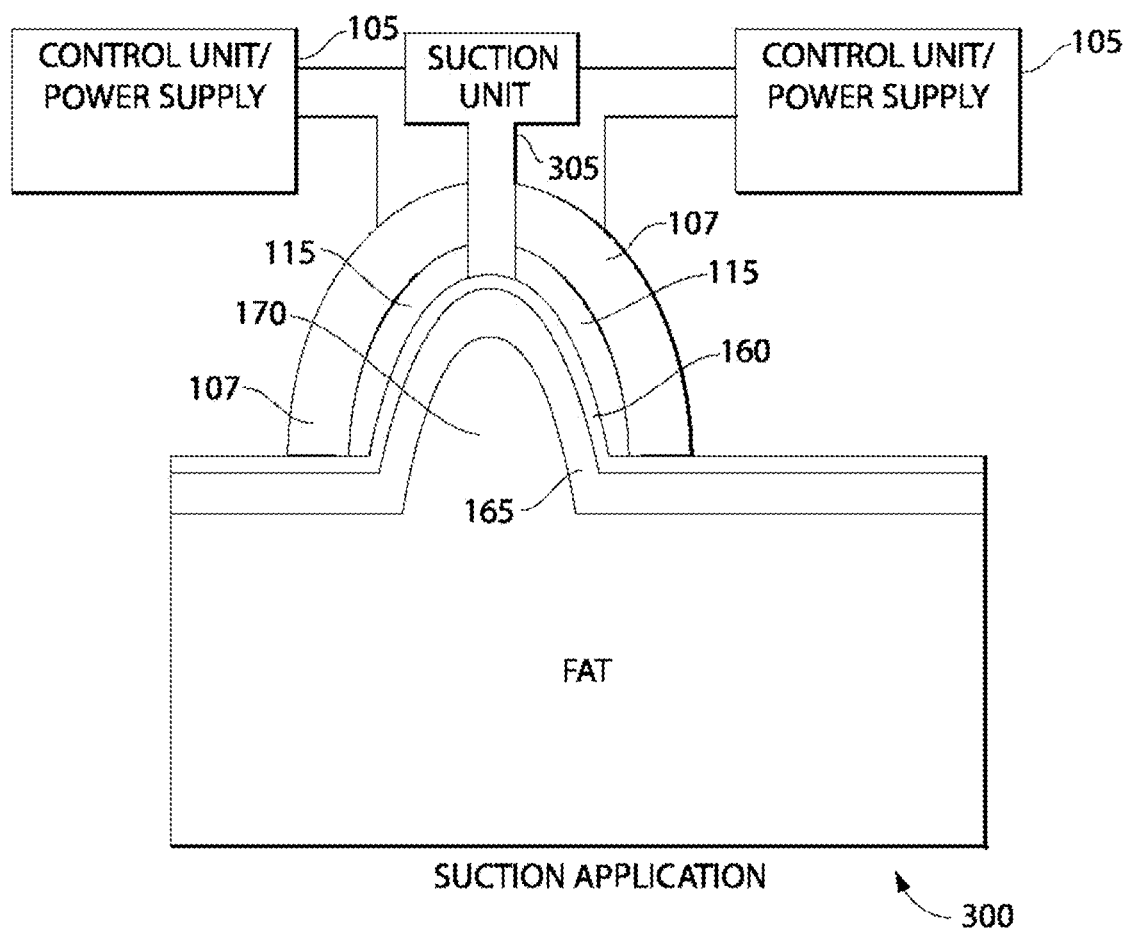

FIGS. 3A and 3B are diagrams showing a treatment system 300 in accordance with an embodiment of the present invention. As shown in FIG. 3A, system 300 may include a suction unit 305, and treatment unit 107 may include treatment interface 115 having a curved surface, which for example forms a dome, for forming and containing a chamber 310 above the epidermis 160. As shown in FIG. 3B, suction unit 305 may be activated to draw the air from chamber 310 or a liquid cooling agent treatment unit 107 into such that target tissue (epidermis 160, dermis 165 and fat cells 170) is pulled up into contact with treatment interface 115. Advantageously, treatment interface 115 may surround target fat cells 170 for more effective cooling. Treatment interface 115 can consist of a solid stiff or flexible material (e.g., a membrane), which is in contact with the skin or a thermal coupling agent between the skin surface and the treatment unit. The surface of the interface 115 can also have multiple openings connected to suction unit 305. The skin is partially entered into these multiple openings, which can increase the total surface area of the epidermis 160 in thermal contact to the treatment interface (e.g., stretching of the skin). Stretching of the skin decreases the thickness of the epidermis and dermis, facilitating cooling of the fat 170. A number of detector(s) 120 and/or probe(s) 180 can be included in treatment system 300 for monitoring tissue temperature during treatment, as described above with reference to FIGS. 1A, 1C, 2A and 2B, detailed description of which will not be repeated here.

Figure 4:
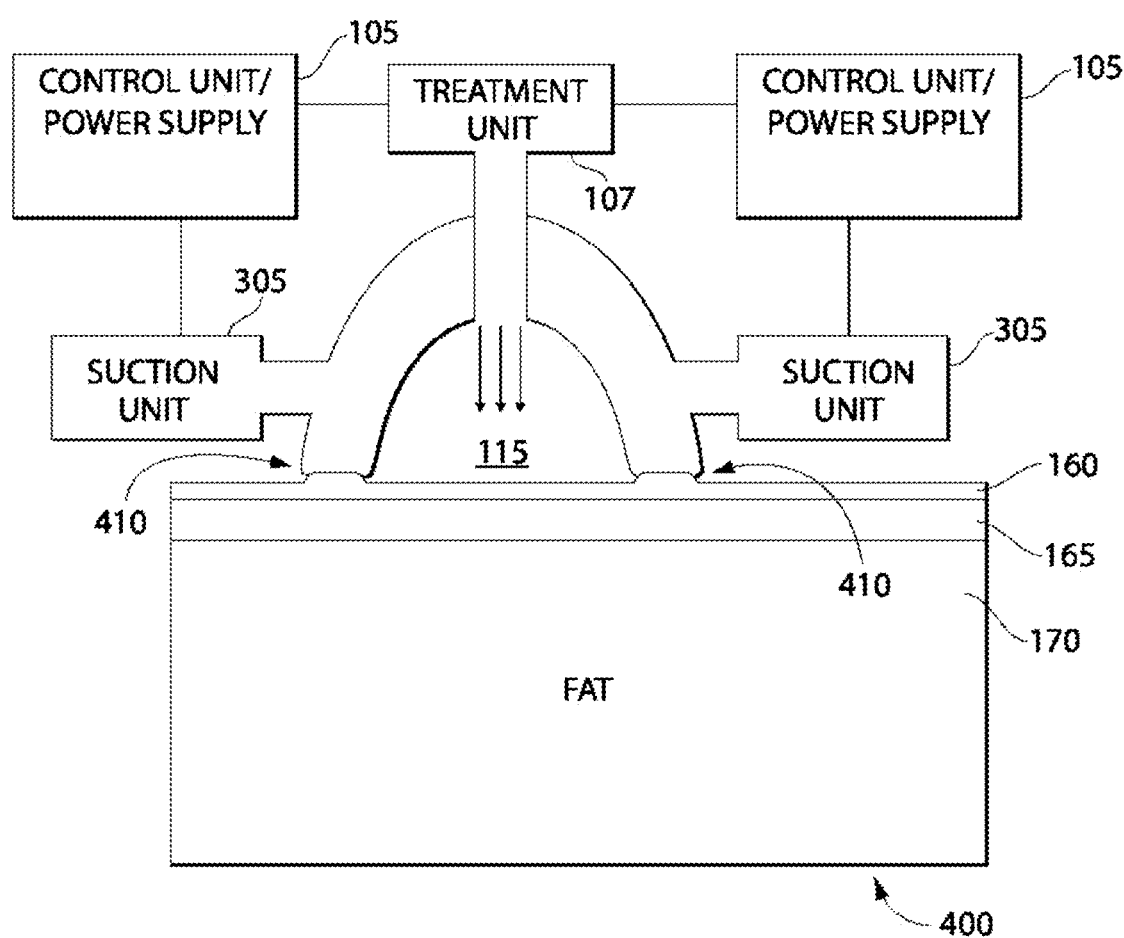
FIG. 4 illustrates a treatment system that is combined with suction system to provide treatment of an isolated area.

FIG. 4 illustrates a treatment system 400 in accordance with an embodiment of the invention. As shown in FIG. 4, suction unit 305 can be connected to a ring opening around treatment interface 115 so that, when activated, a suction seal 410 is formed with the epidermis 160 around treatment interface 115. As a result, treatment can be effected at treatment interface 115 to an isolated target tissue area. Advantageously, the subject or body part may be immersed in a warming bath and the treatment at interface 115 can be unaffected. Consequently, treatment area can be increased while a surrounding warming environment can prevent general hypothermia.

Figure 5A:
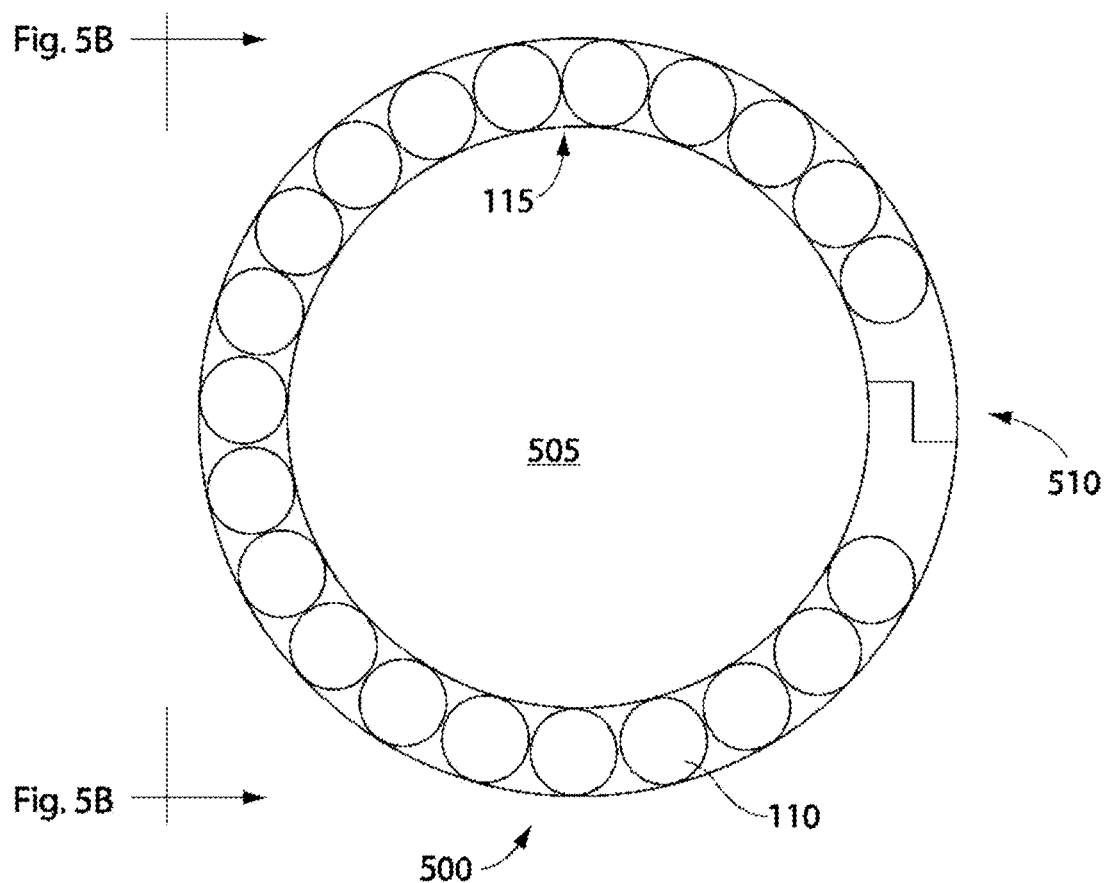
FIGS. 5A and 5B illustrate a treatment system that can enclose circumferentially a target tissue mass.
Figure 5B:
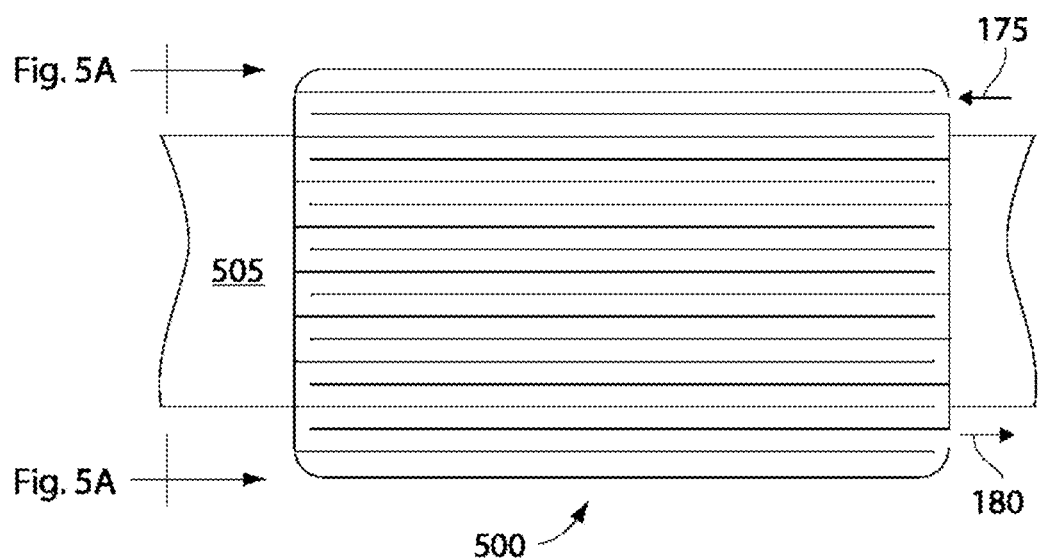

FIGS. 5A and 5B are diagrams showing a treatment system 500 in accordance with an embodiment of the present invention. As shown in FIGS. 5A and 5B, treatment system 500 may form a band (or cylinder) around a target tissue mass 515. Treatment system 500 may comprise any flexible or rigid material. Cooling/heating fluid can be pumped through treatment system 500 via input 175 and output 180, as shown in FIG. 5B. Cooling/heating element 110 can be formed by an internal vessel or a network of passages, such as tubing and the like. Heat transfer with target tissue mass 515 can be effected via treatment interface 115, which can include any heat conducting material. Treatment system 500 can further include a fastening mechanism 510, such as a hook and loop fastener and the like, for fastening and wrapping around tissue mass 515. Furthermore, treatment interface 115 can include a flexible material such that the pressure of cooling fluid pumped through treatment system 500 can be transferred to the target tissue 515. For example, with reference to FIG. 5A, treatment system 500 can apply inward pressure to target tissue mass 515. Target tissue mass 515 can be any section, body part or extremity of a subject. For example, target tissue mass 515 can be an arm, the upper or lower leg, the waist, and so forth, of a subject. The pressure and flow of the cooling fluid in system 500 can be controlled by control unit 105 to an optimal treatment temperature and/or pressure. A tight fit around tissue mass 515 and increased inward pressure can also allow for the subject to be immersed in a warming bath. As described before, fluid flow can be a pulsing flow.

The present invention is additionally described by way of the following illustrative, non-limiting Examples, that provide a better understanding of the present invention and of its many advantages

EXAMPLES

Example 1

Selective Damage to Fatty Tissue by Controlled Cooling In Vivo

Methods of the present invention were carried out on a white, 6 month old, female, Hanford miniature pig ("Pig I") and a black, 6 month old, female Yucatan Miniature Pig ("Pig II"). The pigs were anesthetized using TELAZOL®/xylazine (4.4 mg/kg intramuscular+2.2 mg/kg intramuscular). Inhalant anesthetics (halothane or isoflurane (1.5-3.0%) with oxygen (3.0 L/min) was delivered by mask and filtered with an F-Air canister only if the injectable anesthetics did not provide enough somatic analgesia. Several test sites were marked with micro tattoos by applying India Ink to the corners of each test sites. After mapping of the test sites, cold exposures were performed using a cooling device as described in FIG. 1A. The area of the treatment interface was a flat area of the size of 2×4 cm$^2$ with a built-in temperature sensor. The interface was in thermal contact with a thermoelectric chiller, which was electronically regulated by a control unit such that the temperature at the surface of the interface was kept constant to a pre-set temperature. During the cold exposure the cooling device was applied to the skin with minor to moderate pressure that did not cause significant mechanical compression of blood flow. The cooling element was applied to the skin without any manipulation of the surface profile.

Various combinations of pre-set cooling interface temperatures and exposure times were tested. For some sites a thermo-conductive lotion was applied between the skin and the cooling interface. This thermoconductive lotion consisted mainly of glycerol. Pig I was observed for 61 days until excision biopsies from all test sites were procured and the pig was sacrificed. From test Site C there was an additional punch biopsy procured at day 2.

The biopsies were processed for routine light microscopy and stained with hematoxylin and eosin. The indicated temperature is that of the applied cooling element. Table 1 depicts the parameters of the cooling application and the results obtained at various sites in Pig I:

TABLE 1

| Site | Temperature | Time | Lotion | Results |
|---|---|---|---|---|
| A | −6° C. | 1 minute | + | At 61 days: No epidermal damage. No dermal damage. No obvious indentation. No obvious histological alterations. |
| B | −6° C. | 1 minute | − | At 61 days: No epidermal damage. No dermal damage. No obvious indentation. No obvious histological alterations. |
| C | −6° C. | 5 minutes | + | At 61 days: No epidermal damage. No dermal damage. Indentation due to loss of subcutaneous adipose tissue (1 week to 61 days). Decreased average size of adipocytes at a depth of between about 3-6 mm. Obvious histological damage to the adipose tissue. At 2 days: Tissue inflammation and panniculitis. |
| D | −3.5° C. | 5 minutes | + | At 61 days: No epidermal damage. No dermal damage. No obvious indentation. Borderline histological damage to the adipose tissue. Decreased average size of adipocytes. |
| E | Control | | | Normal- no changes within the epidermis, dermis and subcutaneous adipose tissue. |

Pig II was observed for 50 days until excision biopsies from all test sites were procured and the pig was sacrificed. From test Site E an additional biopsy was procured at day 17. The biopsies were processed for routine light microscopy and stained with hematoxylin and eosin as described above. The indicated temperature is that of the applied cooling element. Table 2 depicts the parameters of the cooling application and the results obtained at various sites in Pig II:

TABLE 2

| Site | Temperature | Time | Lotion | Results |
|---|---|---|---|---|
| C | −6° C. | 5 minutes | − | At 50 days: Pronounced indentation (2-3 mm) due to loss of subcutaneous adipose tissue. No epidermal damage. No dermal damage. No pigmentary changes, however, decreased size of adipocytes and histological damage to adipose tissue. |
| D | −8° C. | 5 minutes | − | At 50 days: Pronounced indentation (2-3 mm) due to loss of subcutaneous adipose tissue. No epidermal damage. |

TABLE 2-continued

| Site | Temperature | Time | Lotion | Results |
|------|-------------|------|--------|---------|
| E | −9° C. | 5 minutes | − | No dermal damage.<br>No pigmentary changes, however, there was damage to the adipocytes to a depth of about 6 mm.<br>Decreased size of adipocytes and histological damage to adipose tissue.<br>At 50 days:<br>Pronounced indentation (2-3 mm) due to loss of subcutaneous adipose tissue.<br>No epidermal damage.<br>No dermal damage.<br>No pigmentary changes, however, there was damage to the adipose cells to a depth of about 6 mm.<br>Decreased size of adipocytes and histological damage to adipose tissue. |
| F | −22° C. | 5 minutes | − | At 17 days:<br>Signs of panniculitis.<br>At 50 days:<br>Pronounced epidermal damage with pronounced hypopigmentation.<br>Scar formation with dermal contraction and complete ablation of the subcutaneous adipose tissue. |

Figure 6:
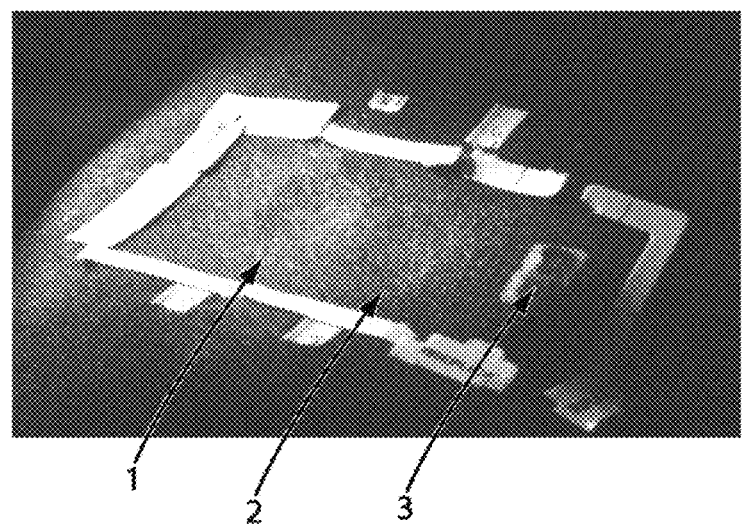
FIG. 6 depicts an image of the skin surface showing indentation after 17 days at some areas matching cold exposure sites.

FIG. 6 depicts an image of the skin surface of test Sites D, E and F of Pig II, 17 days after exposure. An indentation that matches the site of the cold exposure can be seen at 1, which matches test Site D and 2, which matches test Site E. No abnormal epidermal changes can be seen at these test sites. At 3, which matches the test Site F, where aggressive cooling methods were applied, damage to the epidermis is pronounced (e.g., loss of pigmentation and a central crust formation).

Figure 7A:
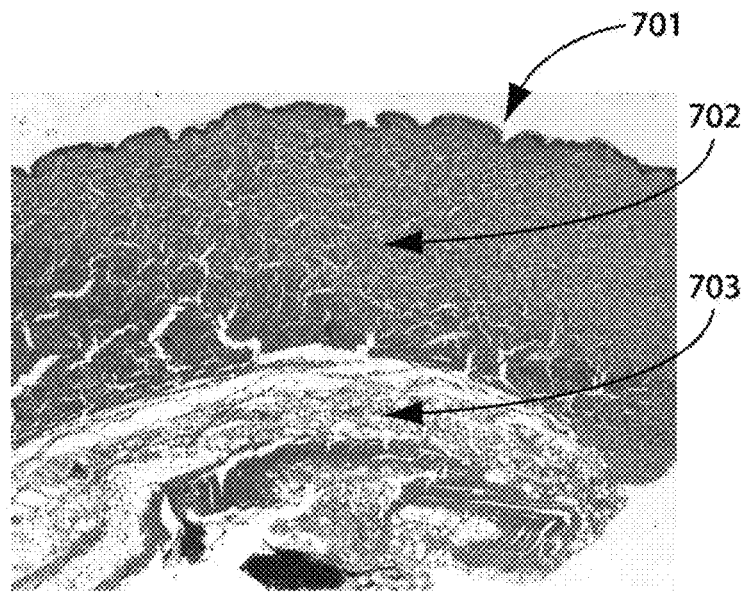
FIGS. 7A and 7B depicts histology of the subcutaneous adipose tissue 17 days after cold exposure (Pig II, Site E).
Figure 7B:
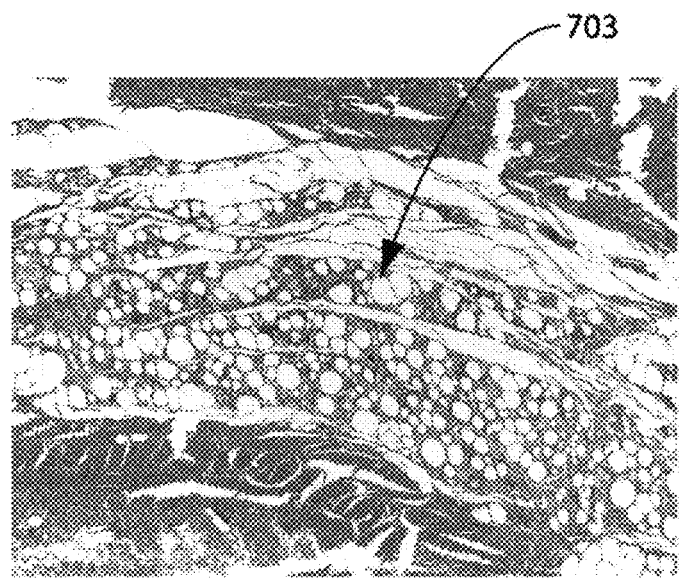

FIGS. 7A and 7B depict histology of test Site E (Pig II), 17 days after cold exposure at −9° C. for 5 minutes, in samples taken from an area below the site of cold exposure. FIG. 7A depicts a low power magnification (1.25×) and FIG. 7B depicts a close up with medium power magnification (5×) of the same specimen. The epidermis 701, dermis 702, subcutaneous adipose 703 and muscle layer 704 are shown. The histology reveals signs of lobular and septal panniculitis within subcutaneous adipose 703, which is an inflammation of the adipose tissue. The average size of fat cells is decreased compared to the sample from the unexposed area. No evidence of tissue alterations is seen in the epidermis, dermis or muscle layer.

Figure 8A:
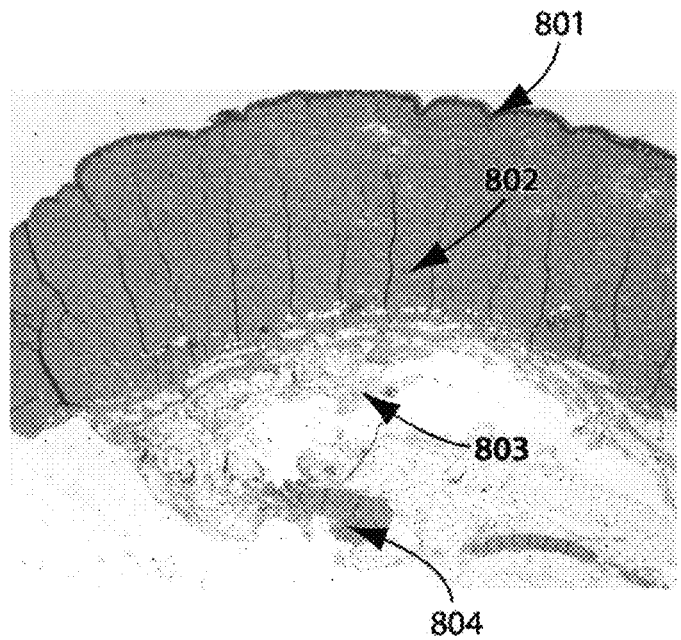
FIGS. 8A and 8B depict Site C.
Figure 8B:
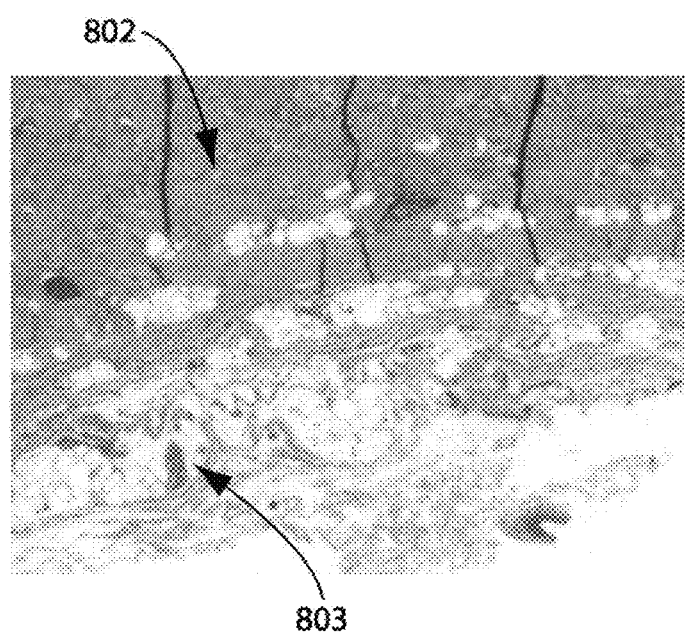
Figure 8C:
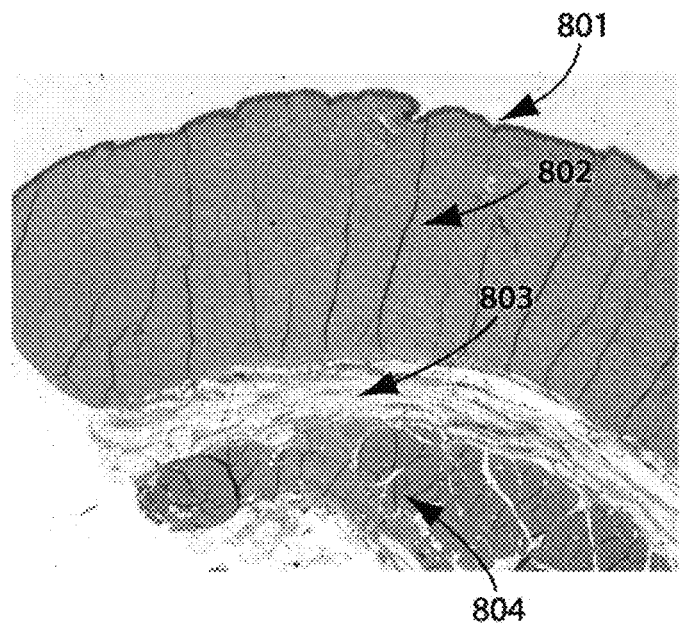
FIGS. 8C and 8D depicts Site E.
Figure 8D:
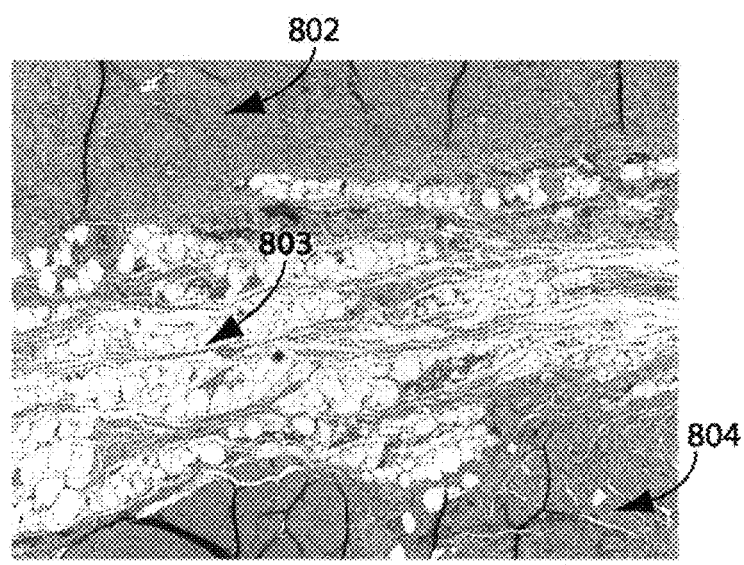
Figure 8E:
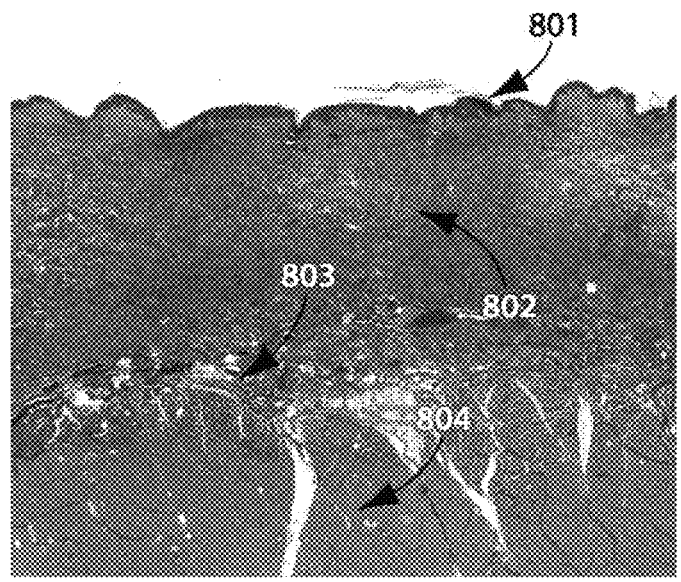
FIGS. 8E and 8F depicts Site F; each of which show histology of the subcutaneous adipose tissue 50 days after cold exposure (Pig II, Site C, E and F)
Figure 8F:
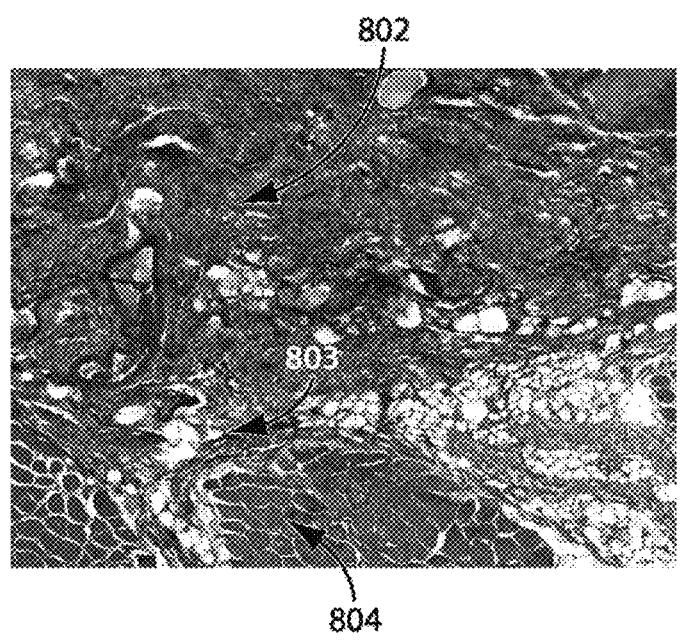

A decrease in subcutaneous adipose tissue was demonstrated by clinical observation of indentation within the skin surface at the precise site of cooling, as well as by histology (hematoxylin and eosin staining). FIGS. 8A, B, C, D, E, and F depicts histology 50 days after exposure with low power magnification of 2.5× (FIGS. 8A, 8C and 8E) and medium power magnification of 5× (FIGS. 8B, 8D and 8F) of test Site C (FIGS. 8A and 8B), test Site E (FIGS. 8C and 8D) and test Site F (FIGS. 8E and 8F). The epidermis 801 and dermis 802 is not damaged in test Sites C and E while the more aggressive cooling regime applied to test Site F resulted in damage to the epidermis and dermis (e.g., scar formation and inflammation can be seen). The subcutaneous adipose 803 shows a decrease of adipocyte size and structural changes (e.g., apparent condensation of the fat cell layer with fibrous septae is included in the condensated fat layer). As a result of the aggressive cooling regime applied to test Site F, almost the entire layer was removed, leaving only some residual fat cell clusters. Thus, where an aggressive cooling regime is applied (test Site F) non-selective and pronounced damage is observed in the epidermis and dermis.

Taken together, the results demonstrate that selective disruption of subcutaneous adipose tissue is achieved using cooling methods of the present invention without causing damage to the epidermis and dermis.

Measurement of temperature during skin surface cooling at −7° C. applied with pressure sufficient to stop skin blood flow, was performed to illustrate the time- and depth-dependence of cooling, in a live pig. Thermocouples inserted at depths of 0, 2, 4, and 8 millimeters were used to record temperature. Although the conditions of this experiment were not ideal (the skin cooler did not maintain strictly −7° C. at the surface), it is clear that cooling of the dermis (2 mm) and fat (4 mm, 8 mm) occurred generally as expected (see for example, FIGS. 10A-10J).

Example 2

Temperature Profile Measurements at Various Tissue Depths

This study was performed using a 6-month old female black, hairless Yucatan minipig (Sinclair Research Center, Columbia, Mo.). The pig will was anesthetized using TELAZOL®/xylazine (4.4 mg/kg intramuscular+2.2 mg/kg intramuscular). Inhalant anesthetic (Halothane or Isoflurane (1.5-3.0%) with Oxygen (3.0 L/min)) was delivered by mask and filtered with an F-Air canister only if the injectable anesthetic did not provide enough somatic analgesia. The test sites were marked with micro tattoos by applying India Ink to the corners of each test site and inserting hypodermic needles into such test site corners. The cold exposure was performed with a convex round copper plate attached to a heat exchanger, which was chilled by a circulating cooling agent tempered to −7° C. The exposure time ranged between 600 to 1200s. Table 3 depicts the parameters of the cooling application and the results obtained at various sites in Pig III. The cold plate had three central openings of approximately 1 mm in diameter through which thermocouples were placed to monitor the temperature profile at different depth of the tissue during cold exposure. The cold exposure device, shown in FIG. 9, was firmly held to the test site during cold exposure. Cold exposures were performed on two different experimental days, one week apart. On the first experimental day the thermocouples were occasionally displaced during the cold exposure leading to a 0.5 mm variability of the thermocouple depth measurement. An additional set of exposures with thermocouples were performed on the second experimental day at well-defined depths with minimal to no variability in the depth of the thermocouples. The location of the thermocouples on the first experimental day for test Sites 1, 2, 3, 7, 11 and 12 was at 2.5, 4.5 and 10 mm depth (+/−0.5 mm). Test Sites 14, 15, 16 and 18 were treated on the second experimental day at a thermocouple depth of 2, 4 and 8 mm, with minimal to no displacement. A certain variability of the thermocouple depth may still be present due to tissue compression during the cold exposure. A glycol containing solution was used to ensure good thermal contact at the skin surface. The pig was observed for 3½ months after treatment, until sacrificed and the tissue of the test sites harvested for analysis. Table 3 depicts the parameters of the cooling application and the results obtained at various sites in Pig III:

The temperature within 4-5 mm depth is within the range of about 0° C. to 7° C. depending on variations in contact pressure and anatomical area. This location demonstrated a high variability of the different temperature plots. The temperature within 8-10 mm depth, which corresponds to a depth within the subcutaneous fat layer had a temperature in the range of 7-24° C.

Histology of a control (Site 9) and cold exposed site (Site 8) (−7° C., 600s) was procured 6 days post exposure and analyzed by a dermatopathologist. The following was described at the control and the cold exposed site:

The epidermis of both samples is normal and exhibits basket-woven stratum corneum with normal thickness, normal rete ridges as compared to the control. Within the cold exposed site there is a mild perivascular, lymphocytic infiltrate present. However no frank signs of vasculitis present in both samples.

The subcutaneous fat of the control exhibits the normal morphology. The subcutaneous fat of the cold exposed site exhibits clear signs of lobular and septal panniculitis. Most of the adipocytes are surrounded by lymphocytic infiltrate with occasional lipid containing macrophages. The thickness of the subcutaneous septae is increased. Mild vascular

TABLE 3

| Site | Temp (coolant agent) | Exposure time | Location | $Temp_{min}$ @ depth | $Temp_{min}$ @ depth | $Temp_{min}$ @ depth | Indentation 3½ months | Relative decrease of superficial fat layer @ 3½ months |
|---|---|---|---|---|---|---|---|---|
| 1 | −7° C. | 5 minutes | Flank | 0° C.@2.5 mm | 7° C.@5 mm | 24° C.@10 mm | + | 66% |
| 2 | −7° C. | 5 minutes | Flank | −2° C.@2.5 mm | N/A | 21° C.@10 mm | + | |
| 3 | control | | Flank | | | | − | 9% |
| 7 | −7° C. | 10 minutes | Abdomen | −3° C.@2.5 mm | 7° C.@5 mm | 19° C.@10 mm | + | |
| 9 | control | | Abdomen | | | | | |
| 11 | −7° C. | 10 minutes | Buttock | N/A | N/A | 12° C.@10 mm | ++ | 79% |
| 12 | −7° C. | 10 minutes | Buttock | −4° C.@2.5 mm | N/A | 13° C.@10 mm | + | 57% |
| 13 | −7° C. | 10 minutes | Buttock | −4° C.@2 mm | N/A | 7° C.@10 mm | + | |
| 14 | −7° C. | 21 minutes | Buttock | −4° C.@2 mm | 3° C.@4 mm | 12° C.@8 mm | + | |
| 15 | −7° C. | 11 minutes | Buttock | −4° C.@2 mm | 1° C.@4 mm | 12° C.@8 mm | + | |
| 16 | −7° C. | 10 minutes | Buttock | −4° C.@2 mm | 0° C.@4 mm | 14° C.@8 mm | ++ | |
| 18 | −7° C. | 15 minutes | Flank | −3° C.@2 mm | N/A | 15° C.@8 mm | + | 66% |

The test sites were exposed to the device, set to a coolant temperature of −7° C. and exposed for 600 to 1200s. The dermis hardened immediately after the cold exposure, as determined by palpation, and became viscose as it returned to its normal temperature, approximately a minute after exposure. There was no epidermal damage or alteration evident by close-up examination with polarized magnifier lens minutes after exposure. There was no blister formation and Nikolsky-sign was negative. During the entire survival period there was no gross damage to the epidermis. No crusting, blister or pronounced pigmentary changes were observed. Some test sites exhibit a minor increase in epidermal pigmentation. This mild hyperpigmentation could be removed after few months by gentle rubbing of the epidermis.

Figure 11:
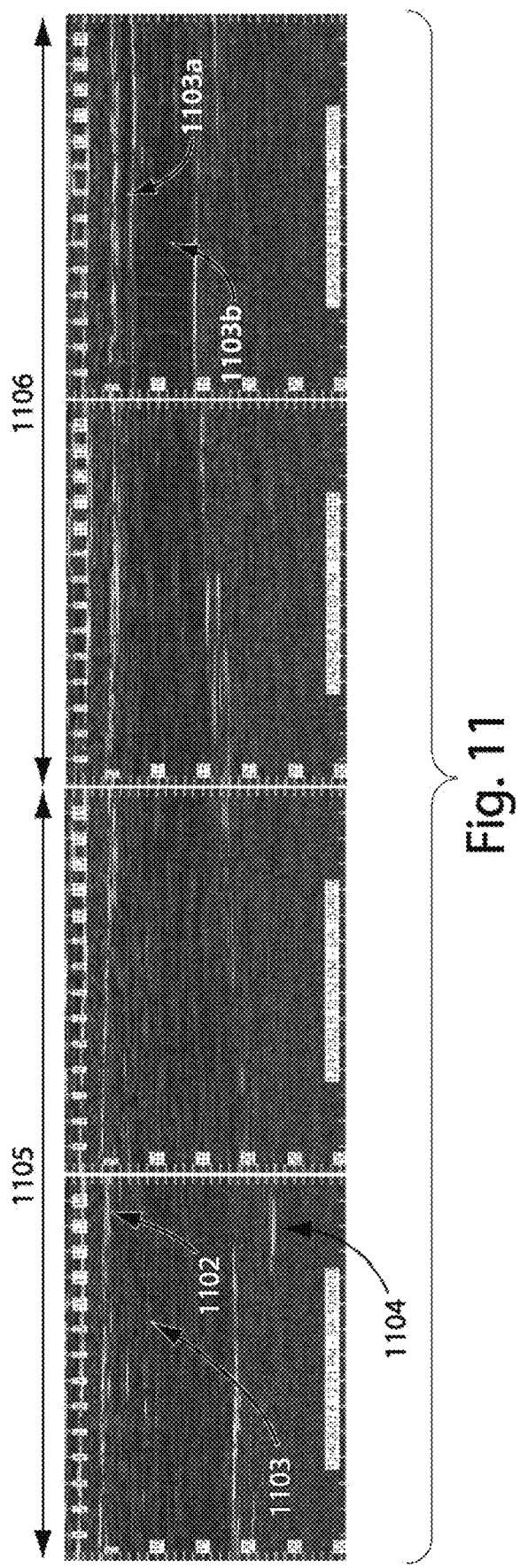
FIG. 11 depicts an ultrasound image of test Site 11, 3.5 months after exposure.

The temperature measurements of the thermocouples depended on depth, body location, and the pressure with which cooling was applied. The temperature plots at different tissue depths during the cold exposure are shown in FIGS. 10A-10J for various test sites and are also summarized in Table 3. For some test sites, temperature oscillations that might be related to a nearby blood vessel was observed. Some temperature plots were not considered due to movements or misplacement of the thermocouple (labeled 'error' in Table 3). The temperature within the deep dermis or superficial fat layer is within the range of −2° C. to −4° C.

changes however no frank signs of vasculitis. Three and one half months after the cold exposure the pig was sacrificed and tissue at the exposure sites was harvested by full thickness excision, after 20 MHz ultrasound imaging was performed through selected test sites. The in-vivo ultrasound images clearly demonstrated loss of fatty tissue in the area of treatment by skin cooling vs. the non-cold exposed surrounding tissue. An in-vivo ultrasound image 3½ months after cold exposure is shown in FIG. 11.

The harvested tissue was cut macroscopically through the test sites and images were taken from the macroscopic tissue cross-sections. The macroscopic cross sections of Sites 1, 3, 11, 12 and 18 are shown in FIG. 13A-13E. A decrease of the thickness of the subcutaneous fat layer was observed for all cold exposed sites vs. the non-cold exposed adjacent fat layer. The macroscopic cross sections matched well with the ultrasound images. Two different compartments within the subcutaneous fat could be identified, a superficial fat layer and a deep fat layer. Thickness of the superficial fat layer was dramatically reduced at sites of cold treatment, while the deep fat layer was not significantly changed. The percentage of decrease of the superficial fat layer inside the test area vs. outside is listed for some test sites in Table 3. A change of the subcutaneous fat layer was observed for cold exposed Sites 1, 11, 12 and 18. The average decrease of thickness for the superficial fat layer within the evaluated test sites was 47%. For the unexposed control side, no significant decrease of thickness was found in either fat layer.

These examples confirm that it is possible in a pig model to achieve selective tissue damage of the subcutaneous adipose tissue by external cooling within a specific range of external cooling temperature and exposure time, without significant damage to the epidermis and dermis. Removal of subcutaneous fat was also demonstrated by an obvious indentation at the treated skin surface, which matched exactly with the cooling exposure, and with the measurements of the fat layer in relation to the cold exposure site by ultrasound and macroscopic cross sections after sacrifice. Pronounced histological changes, which were selective to the subcutaneous adipose tissue were observed 6 days after cold exposure. Histologically a panniculitis with a decrease in fat cell size was observed. There was evidence that the response to the cold can vary for different sites and that the more superficial fat layer is more affected by tissue loss than the deeper fat layer. The results of Pig III however imply that there is enhanced fat removal at the superficial fat layer vs. the deeper layer. The explanation for this is a) the superficial fat layer is exposed to colder temperatures because of the gradient and/or b) the deeper fat layer in pigs may be less susceptible to selective cold damage.

Figure 9:
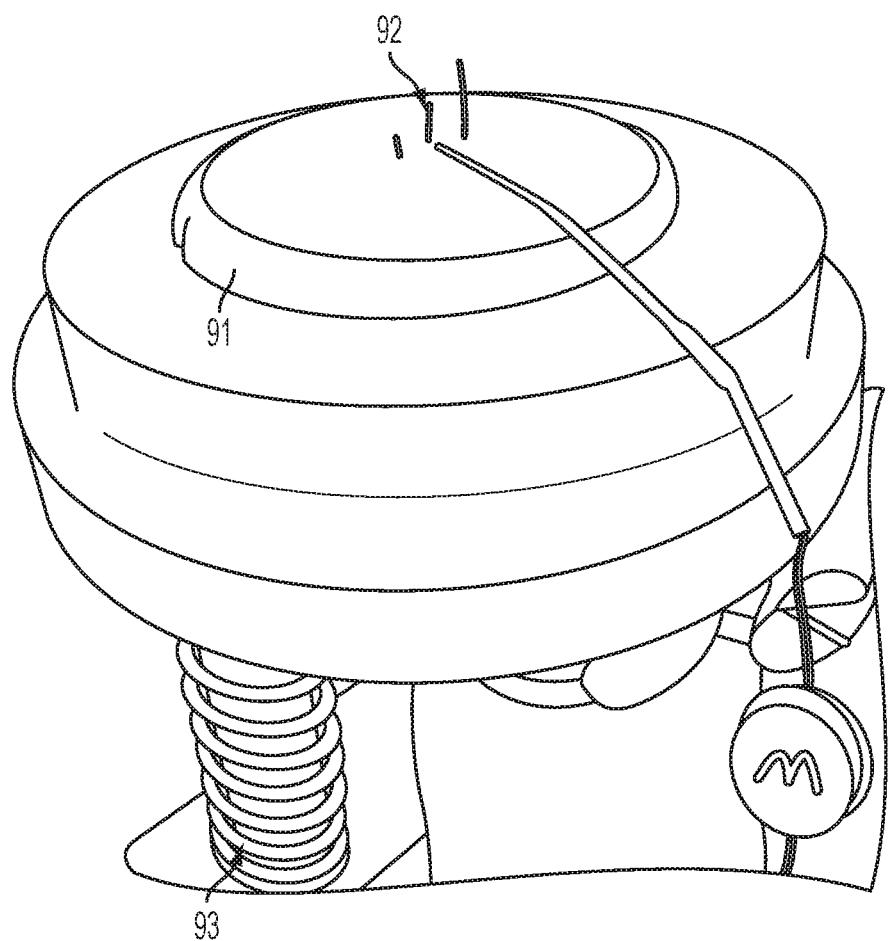
FIG. 9 depicts an image of the device used to administer cooling to Pig III.
Figure 10A:
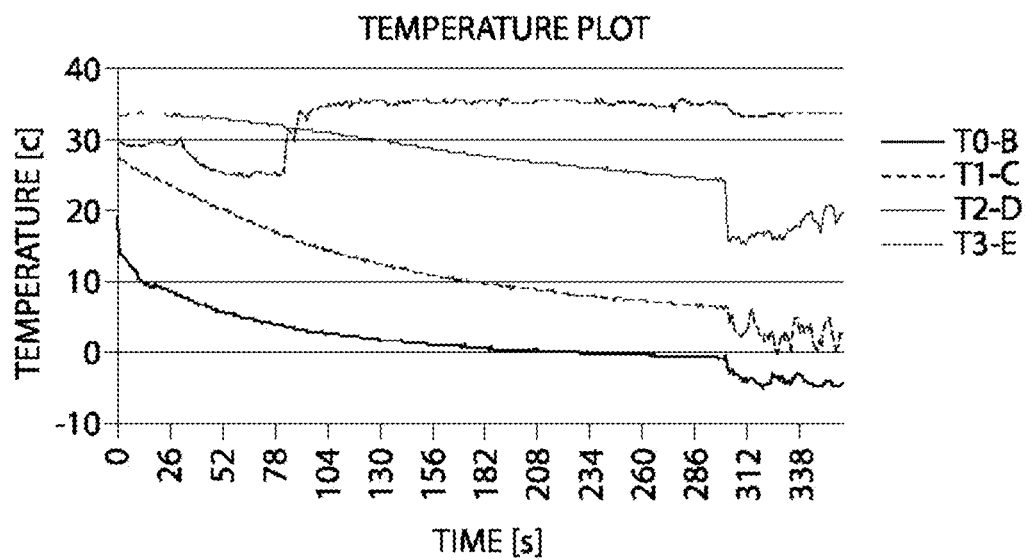
FIGS. 10A, 10B, 10C, 10D, 10E, 10F, 10G, 10H, 10I, and 10J depict temperature plots of the exposure sites 1, 2, 7, 11, 12, 13, 14, 15, 16 and 18 of Pig III in various tissue depths.
Figure 10B:
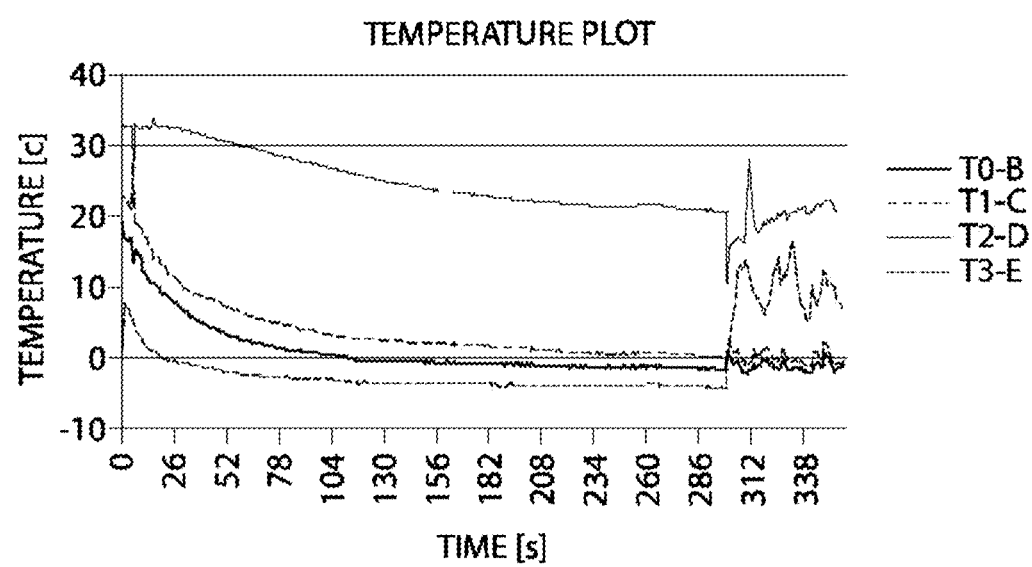
Figure 10C:
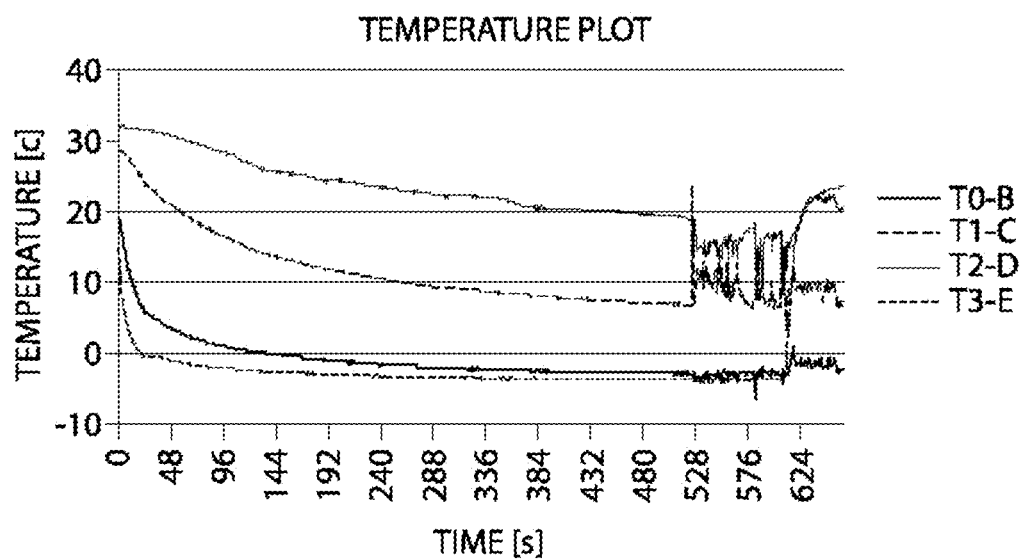
Figure 10D:
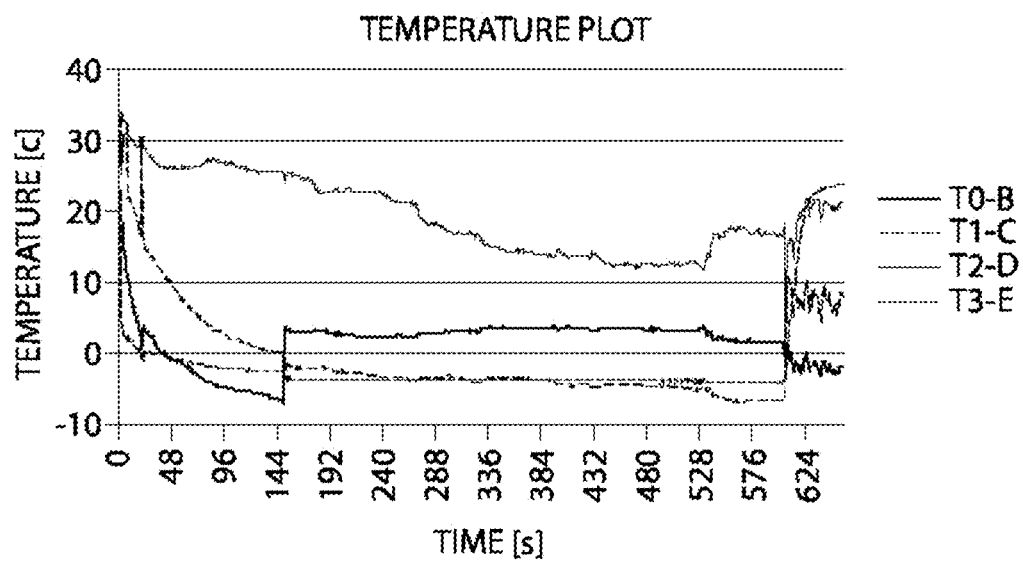
Figure 10E:
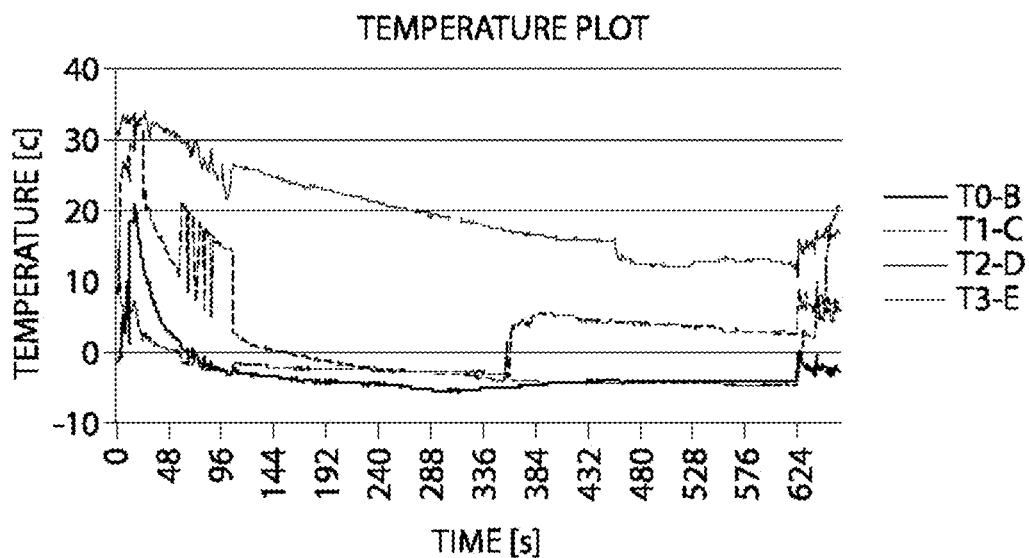
Figure 10F:
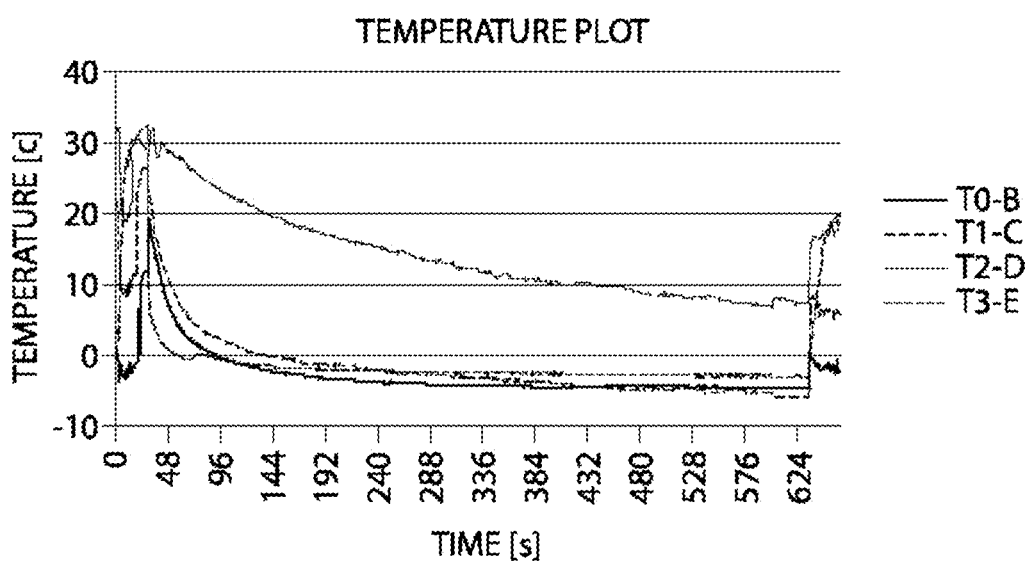
Figure 10G:
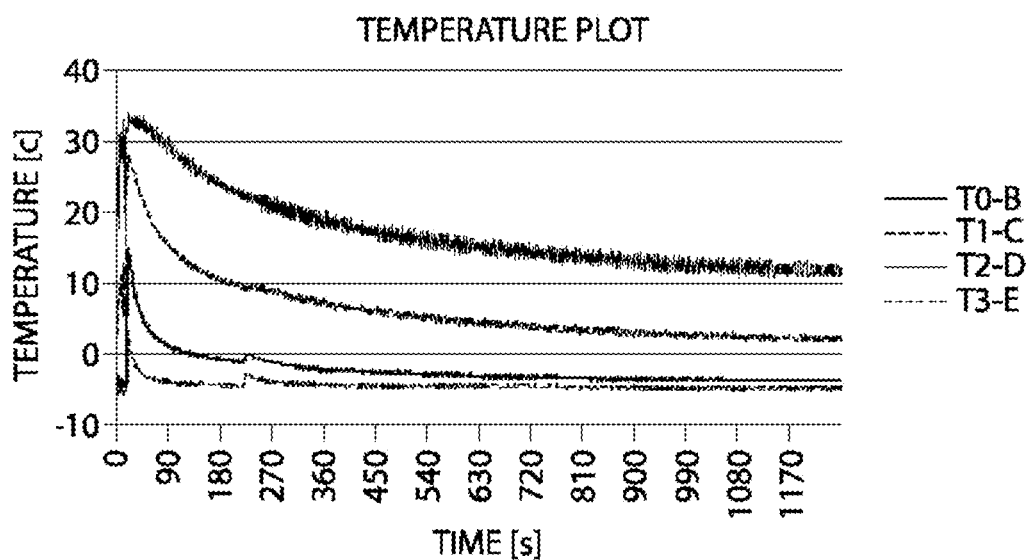
Figure 10H:
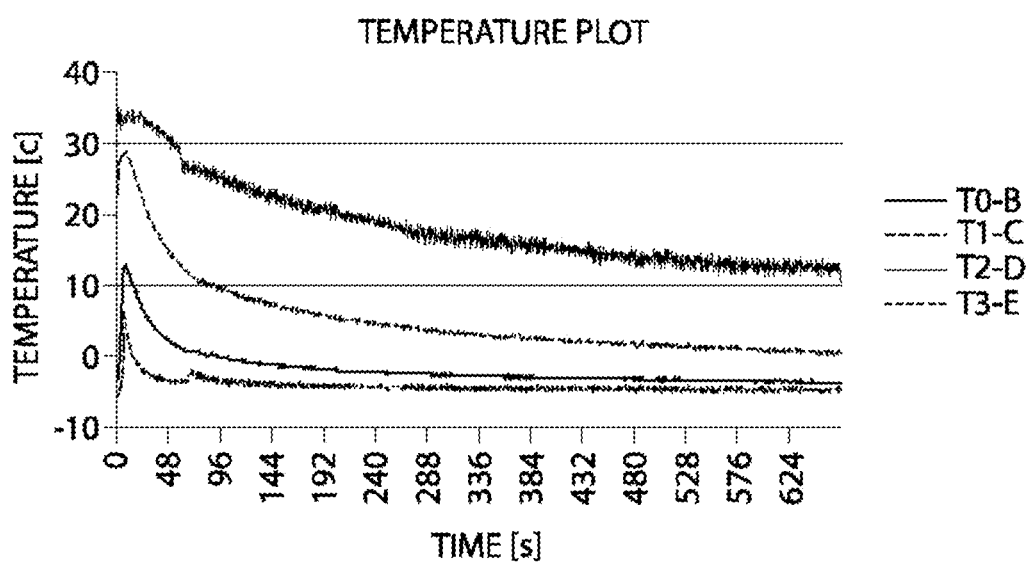
Figure 10I:
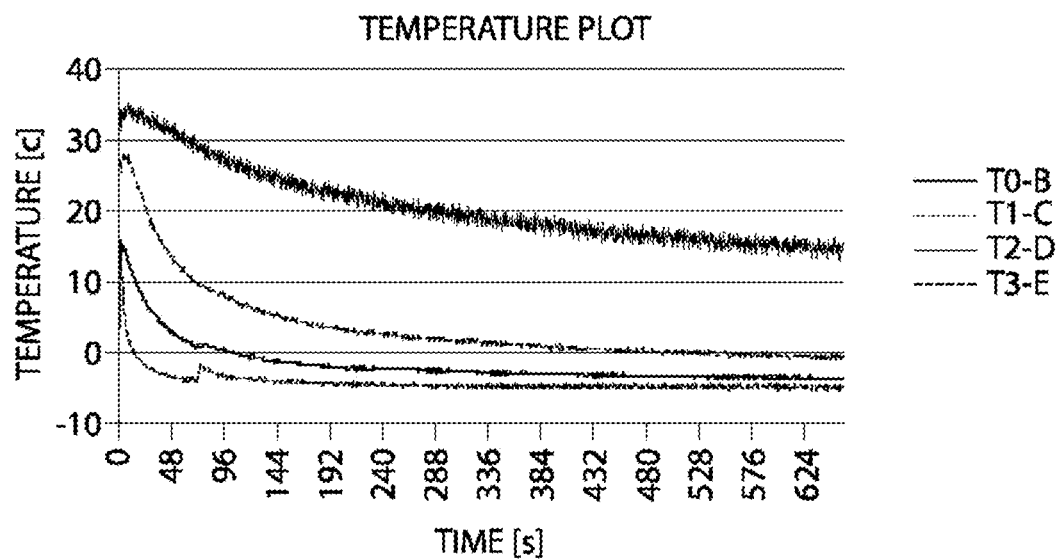
Figure 10J:
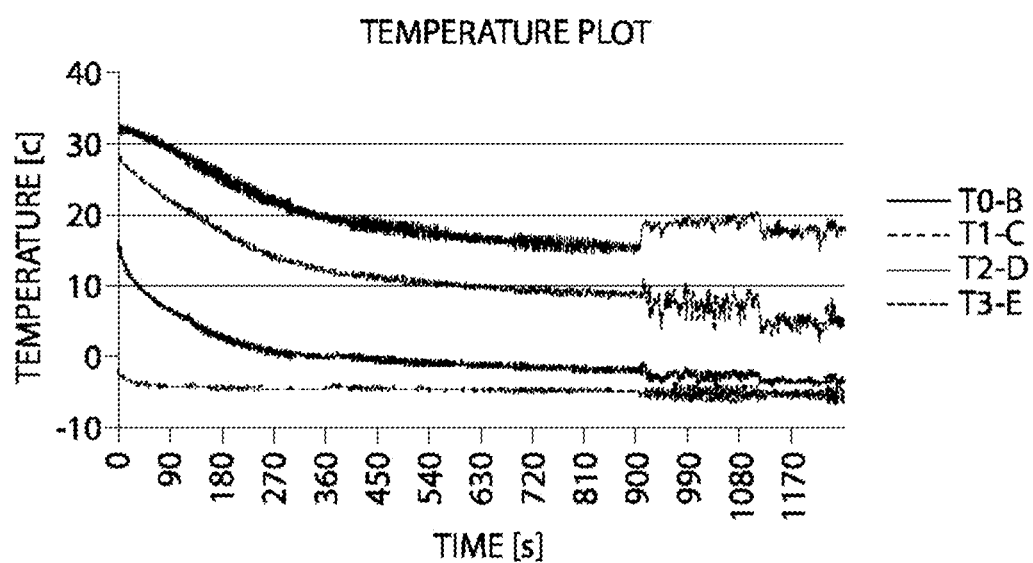

FIG. 9 depicts an image of the device for the cold exposure of Pig III. The cold copper plate 91 is brought in contact with the skin. The temperature profile within the skin during cold exposure is measured by thermocouples 92 inserted into the tissue in different depths. The device is spring loaded 93 to provide a pressure during the cold exposure.

FIGS. 10A-10J depict the temperature profile in various depths during the cold exposure of Pig III for different test Sites: 10A (Site 1), 10B (Site 2), 10C (Site 7), 10D (Site 11), 10E (Site 12), 10F (Site 13), 10G (Site 14), 10H (Site 15), 10I (Site 16) and 10J (Site 18). The temperature in various depths is labeled with T3-E (surface), T0-B (2-2.5 mm), T1-C(4-5 mm) and T2-D (8-10 mm).

FIG. 11 depicts an ultrasound image of test Site 11 taken 3½ months after exposure. The section below 1105 is outside the cold exposed area the section below 1106 is within the cold exposed area. The dermis 1102 can be clearly distinguished from the fat layer 1103 and the muscular layer 1104. Within the fat layer 1103 two distinct layers can be distinguished: the superficial fat layer 1103a and the deep fat layer 1103b. The ultrasound image matches well with the macroscopic cross section of the same tissue in FIG. 13C.

Figure 12A:
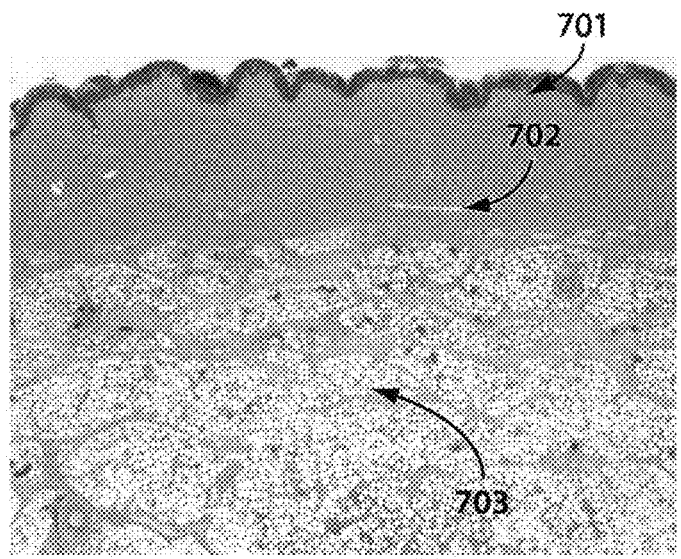
FIGS. 12A and 12B depict histology of test Site 8, 6 days after exposure.
Figure 12B:
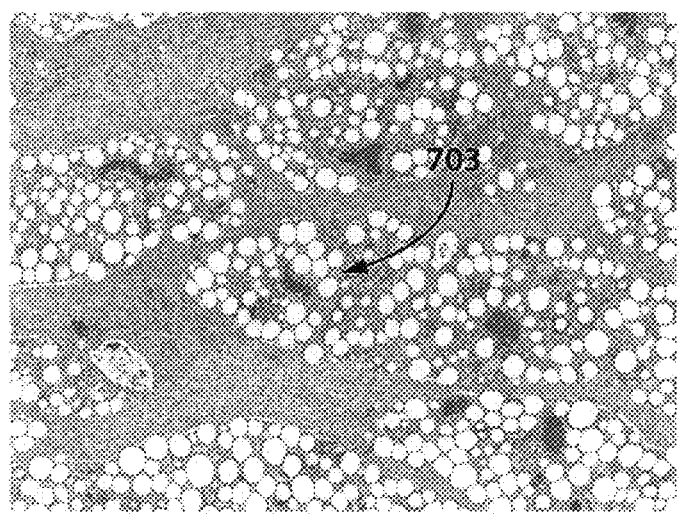
Figure 12C:
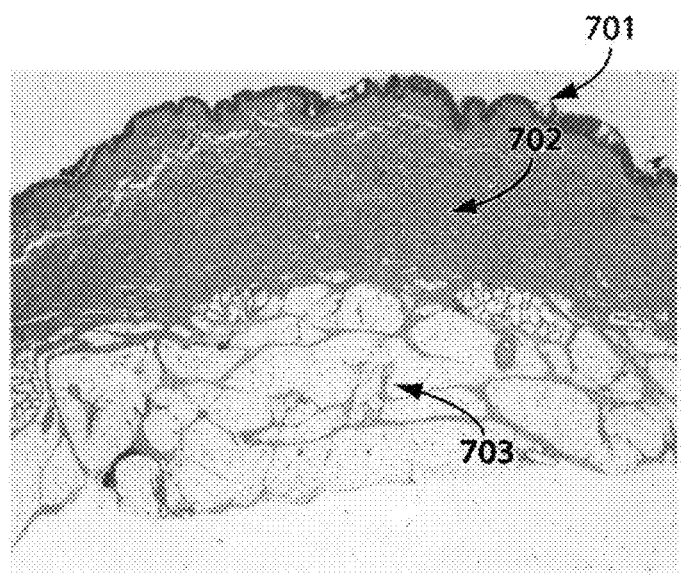
FIGS. 12C and 12D depicts histology of test Site 9 (control)
Figure 12D:
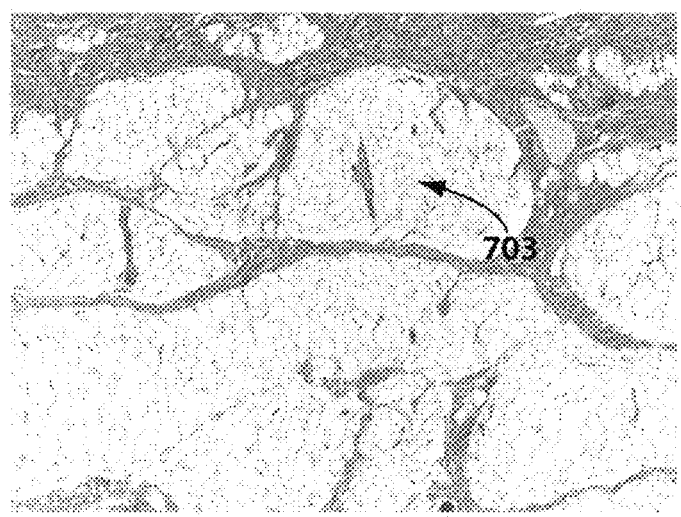

FIGS. 12A-12D depict histology of test Site 8 (FIGS. 12A and 12B) six days after cold exposure (−7° C., 600s) and test Site 9, which is an unexposed control (FIGS. 12C and 12D). The micrographs show an image of low power magnification (1.25×) in FIGS. 12A and 12C and a medium power magnification (5×) in FIGS. 12B and 12D. The images showing the epidermis 701, the dermis 702 and the subcutaneous fat 703. While the unexposed control exhibits normal tissue morphology, the cold-exposed tissue exhibits clear signs of panniculitis in the subcutaneous fat. Inflammatory cells have migrated into this area and the average fat cell size is decreased.

Figure 13A:
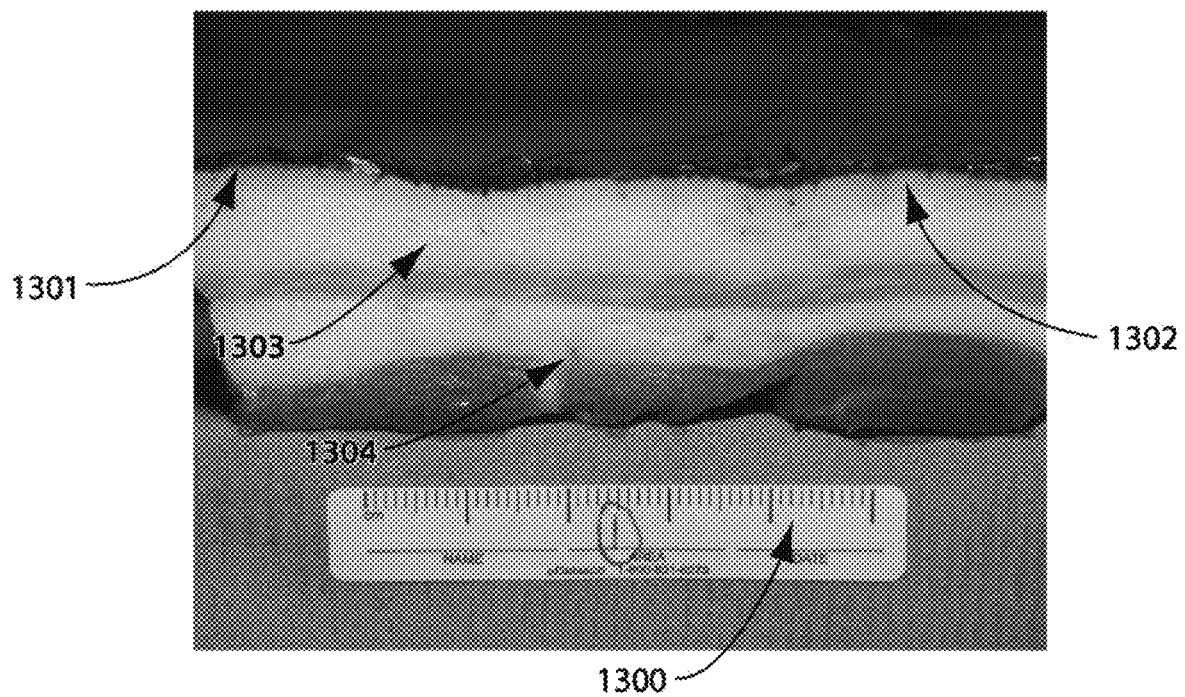
FIGS. 13A, 13B, 13C, 13D, and 13E depict macroscopic sections through the center of test Sites 1, 3, 11, 12 and 18, 3.5 months after exposure.
Figure 13B:
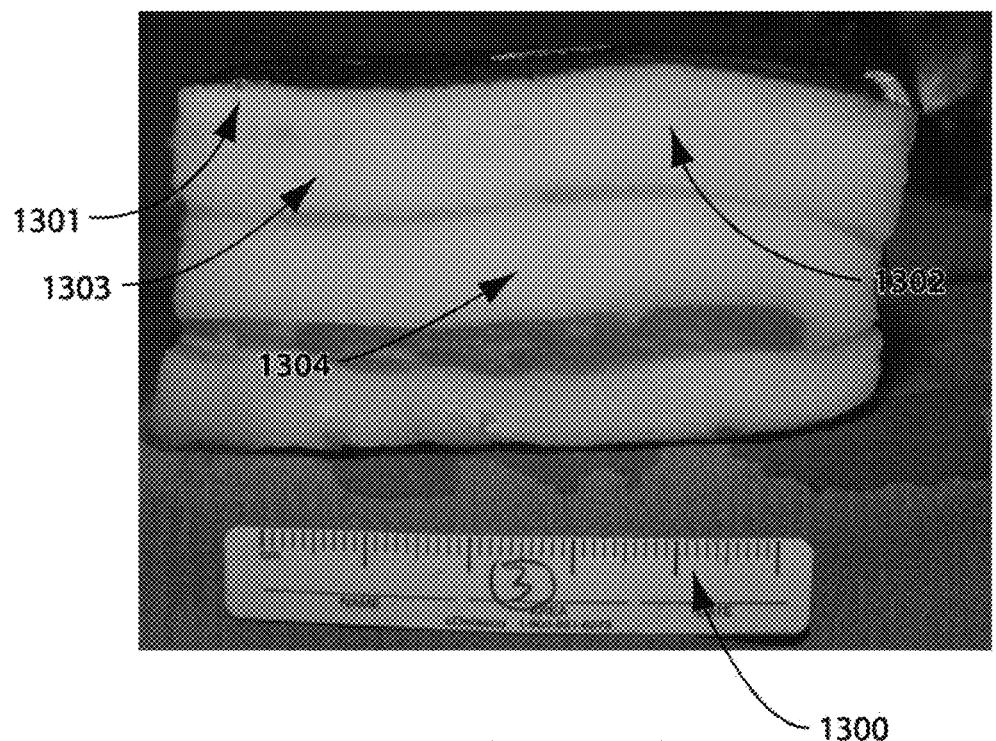
Figure 13C:
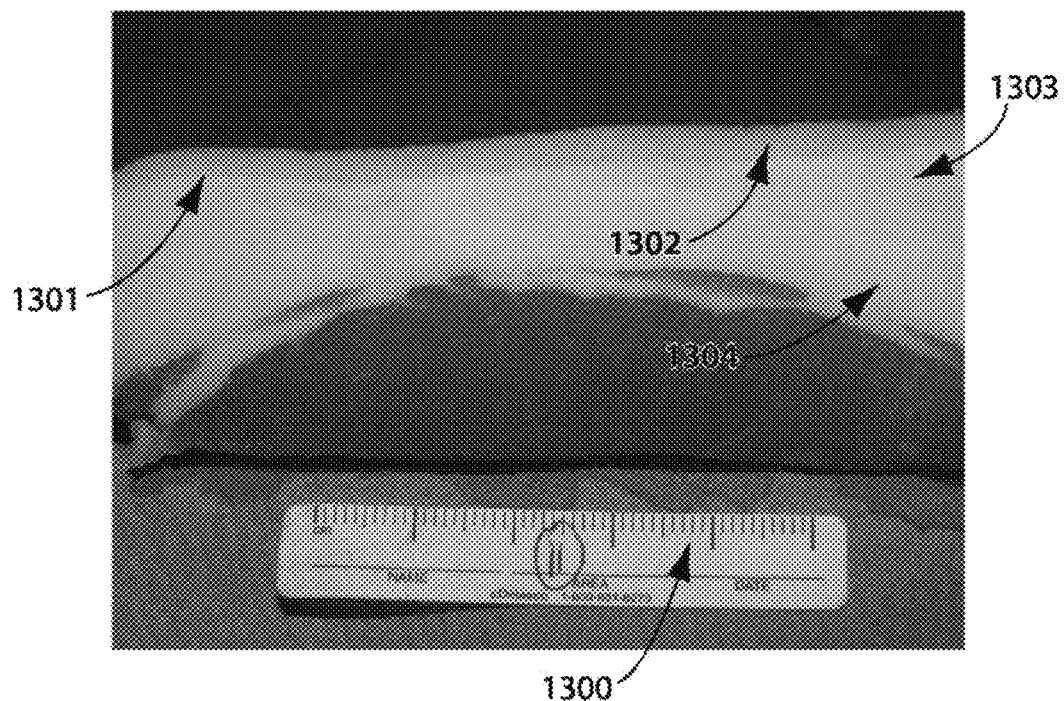
Figure 13D:
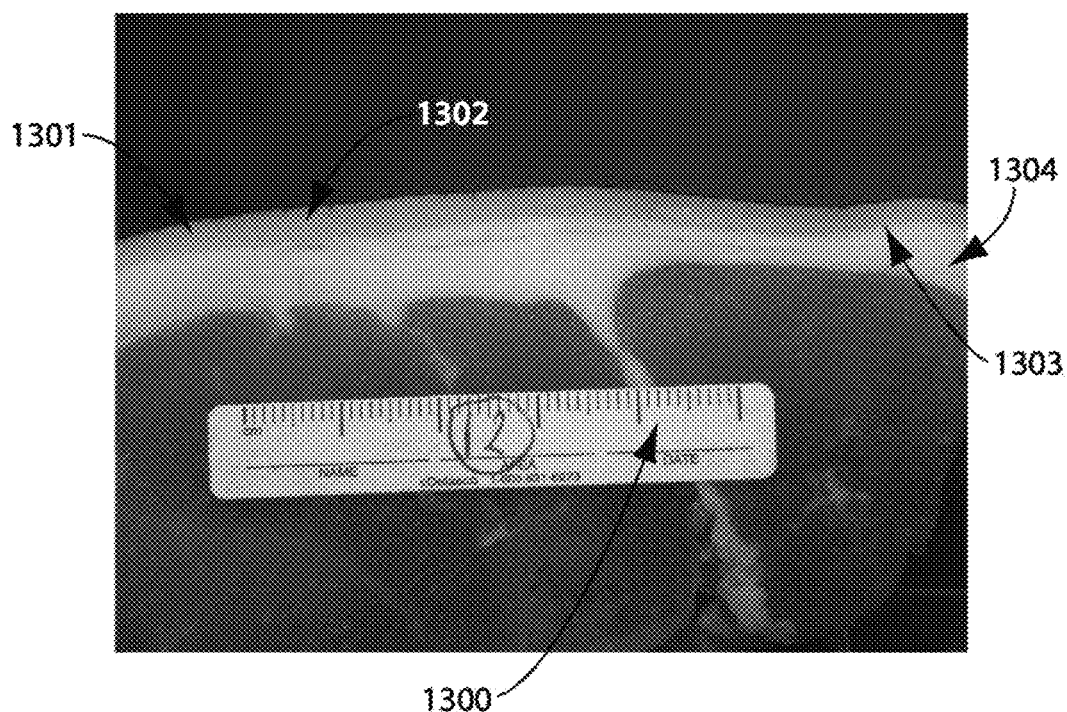
Figure 13E:
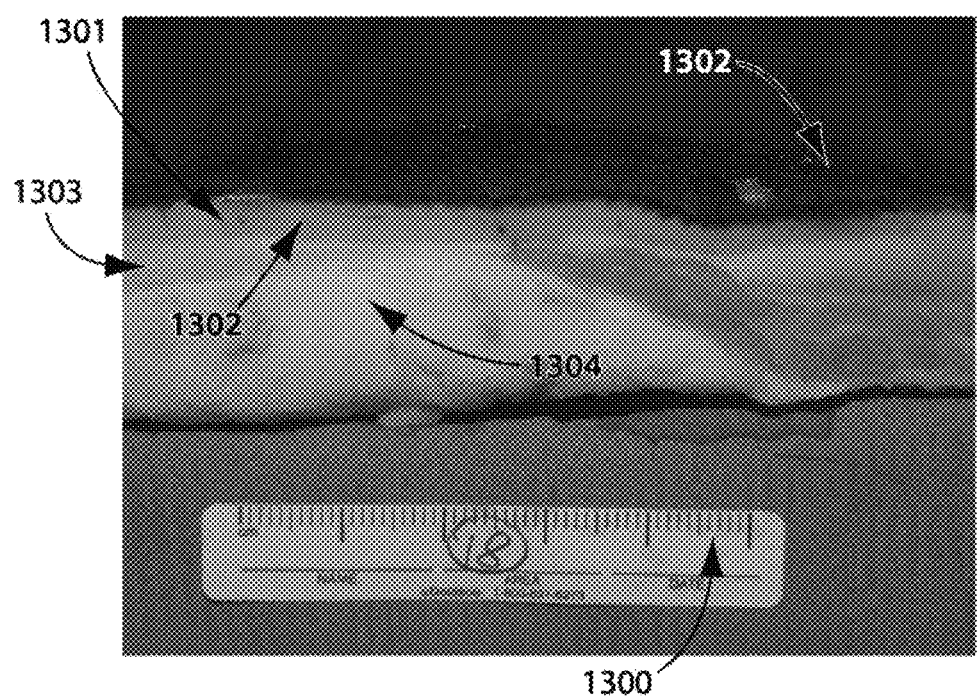

FIGS. 13A-13E depict macroscopic sections through the center of different test Sites after the pig was sacrificed, 3½ months after cold exposure: 13A (Site 1), 13B (Site 3), FIG. 13C (Site 11), FIG. 13D (Site 12) and FIG. 13E (Site 18). Each Figure exhibits a scale 1300, which has 1 cm units and 1 mm subunits. The epidermis 1301, the dermis 1302, the superficial fat layer 1303 and the deep fat layer 1304. For the unexposed control FIG. 13B, no change of thickness of different layers can be seen. FIGS. 13A, 13C, 13D and 13E show the cross section of cold exposed areas, which is matched to the central 4-5 cm of tissue and non-cold exposed areas surround. A decrease of thickness within the superficial fat layer of the cold exposed areas vs. the non-cold exposed areas can be seen in all cold exposed samples. The change in % of thickness for each of the sample is listed in Table 3.

Example 3

Selective Loss of Subcutaneous Fat Over Time

Several months after treatment, selective loss of subcutaneous fat was maintained in Pig III, which was fed a standard diet. No scarring or cutaneous damage was observed, as described in further detail herein.

Figure 14:
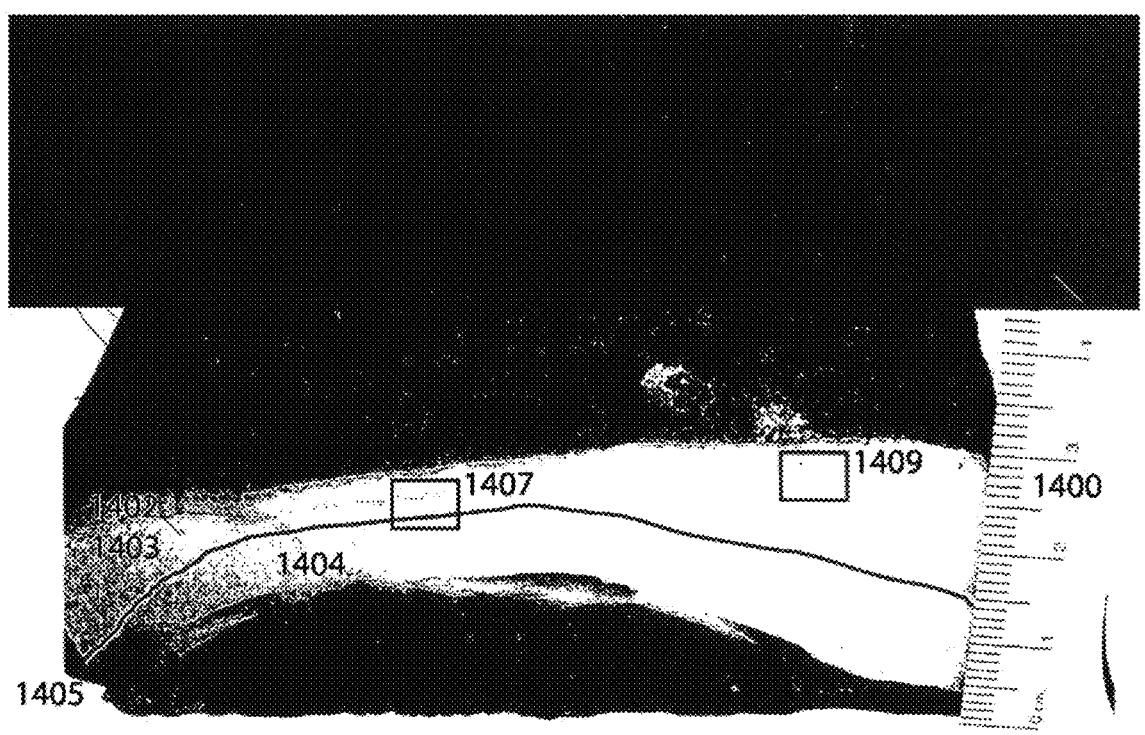
FIG. 14 depicts macroscopic sections through test site 11 (shown in FIG. 13C). Areas of indentation were evaluated by histological analysis (shown in FIGS. 15A, 15B, 16A, and 16B)

FIG. 14 indicates where samples from test site 11 (shown in FIG. 13 C) were obtained 3.5 months post-treatment. These samples were used for histologic analysis, as shown in FIGS. 15A, 15B, 16A, and 16B. A scale 1400, has 1 cm units and 1 mm subunits. The cross section depicts the epidermis 1401, the dermis 1402, the superficial fat layer 1403 and the deep fat layer 1404, which are separated by a fascia 1405 (marked by a dashed line). The treatment area 1406 contains a marked rectangle 1407 within the underlying fat, which indicates the location of the histology shown in FIGS. 15A and 15B. The area 1408, which is outside of the treatment area contains a marked rectangle 1409 within the underlying fat, which indicates the location of the histology shown in FIG. 16.

Figure 15A:
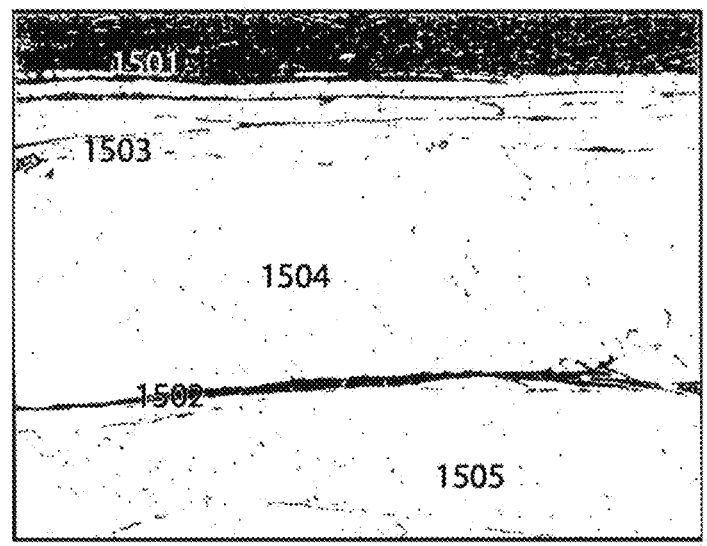
FIGS. 15A and 15B depict results of histological analysis of samples obtained from test site 11 at 3.5 months post-treatment.
Figure 15B:
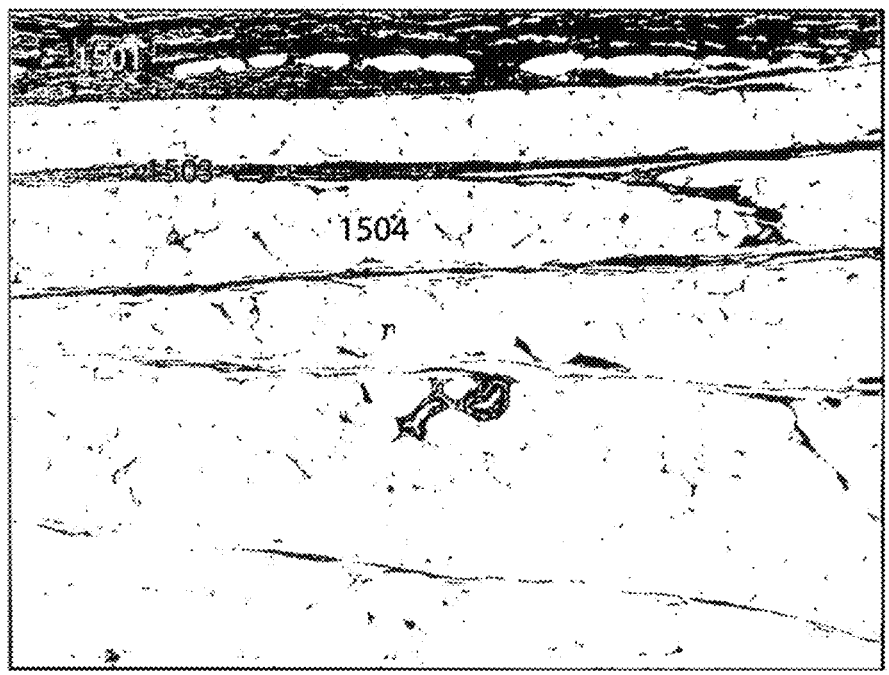
Figure 16A:
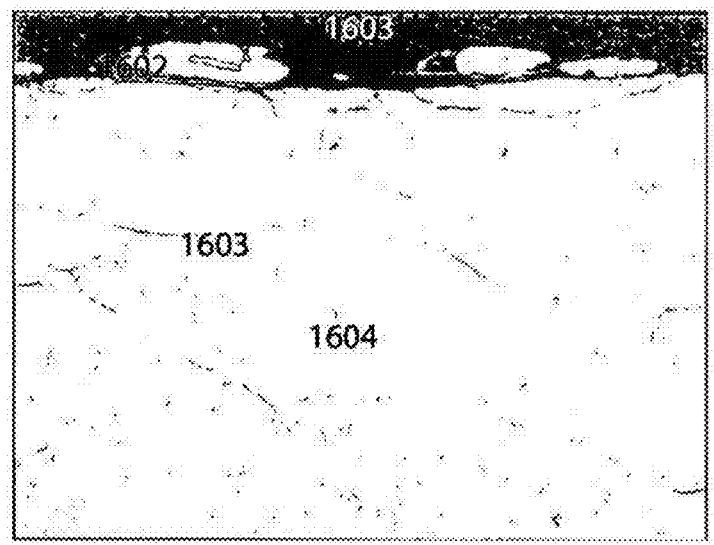
FIGS. 16A and 16B depicts results of histological analysis of samples obtained from the non-cold exposed site next to test site 11 at 3.5 months post-treatment.
Figure 16B:
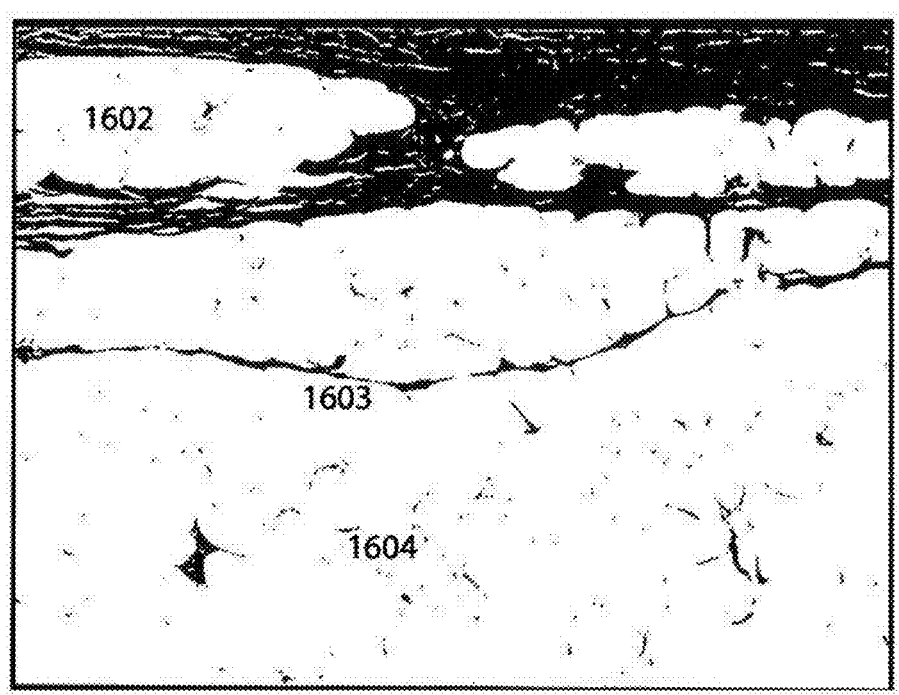
Figure 17:
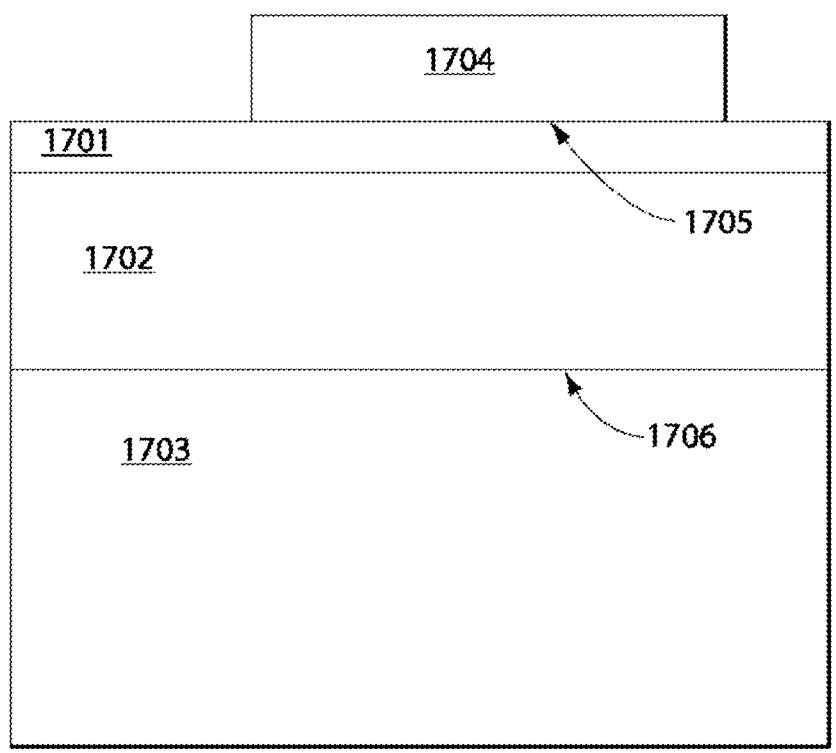
FIG. 17 depicts schematic locations of the thermocouples used to obtain the temperature plot of FIG. 18. The superficial thermocouple 1705 is located at the interface between the cooling device 1704 and the epidermis 1701. The deeper thermocouple 1706 is located below the dermis 1702 within the superficial part of the subcutaneous fatty tissue.
Figure 18:
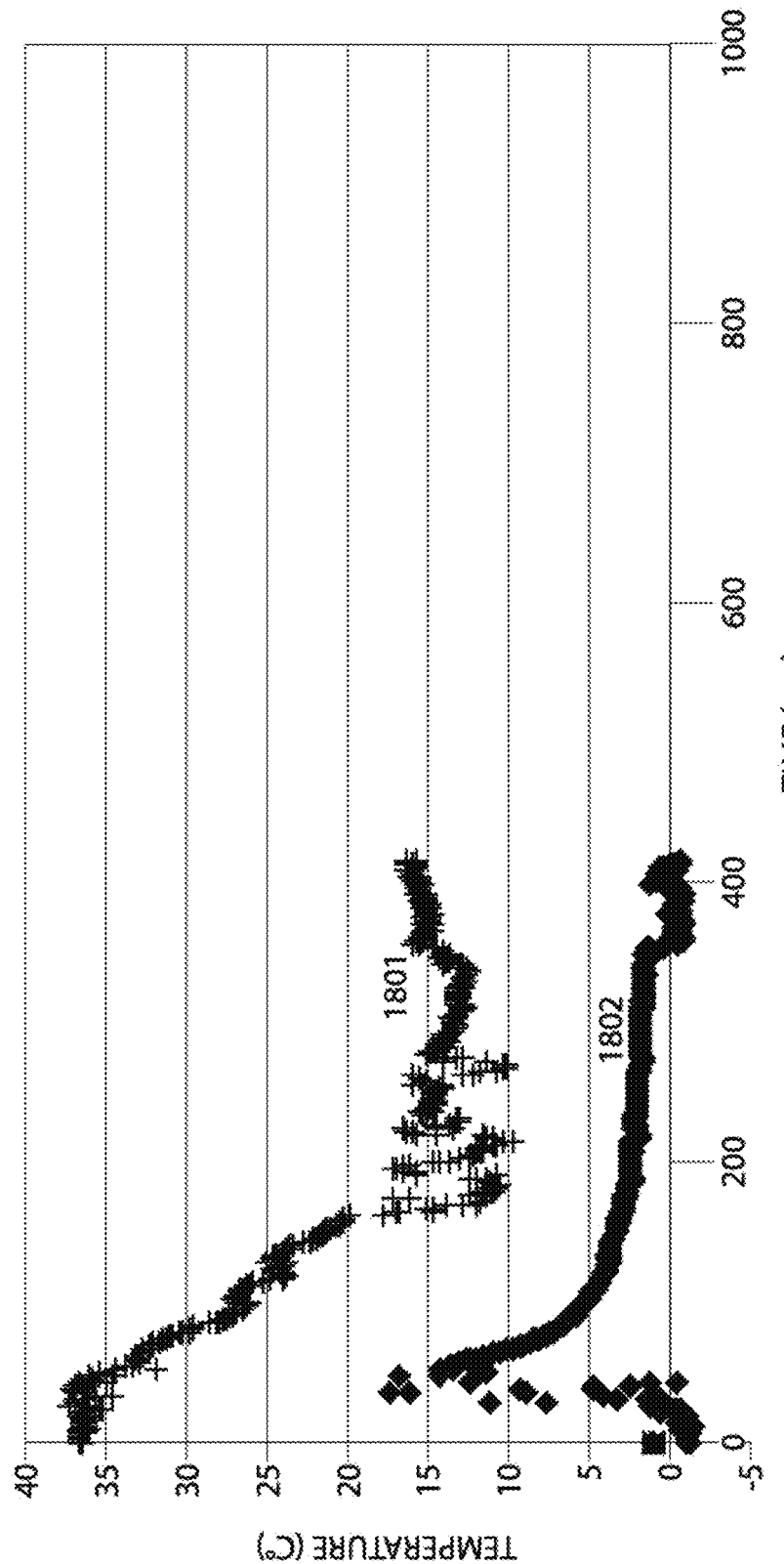
FIG. 18 depicts a temperature plot generated during in-vivo cold exposure. The temperature plot shows the temperature measured in Celsius (y-axis) over time in seconds (x-axis) as measured by two thermocouples at different locations during treatment. Graph 1801 exhibits the temperature plot as measured by a thermocouple located at the superficial fat layer just below the dermis. Graph 1802 exhibits the temperature plot as measured by a thermocouple located at interface between the cooling device and the epidermis.

Histology of a sample taken from within test site 11 at 3.5 months post-treatment is shown in FIGS. 15A and 15B. The dermis 1504 does not exhibit any inflammation or tissue damage. The septum 1502, separates the superficial fat layer 1504 from the deep fat layer 1505. Fine septae 1503 separate individual fat lobuli, which contain clusters of adipocytes. No evidence of inflammation can be observed in FIGS. 15A and 15B. There is also a decrease in average size of the adipocytes, as compared to the corresponding histology obtained from the control sites (FIGS. 16A and 16B). The comparison also demonstrates a compaction of the fine septae within the superficial fat layer. This indicates that the volume of superficial fat, number of adipocytes and also the average size of individual adipocytes is reduced as compared to the unexposed control site. There is also a fat pocket within the dermis 1504 that is decreased in volume, adipocyte number and individual adipocyte size in comparison to a control fat pocket shown in FIGS. 16A and 16B. The intradermal fat pocket shown in FIG. 15 consists of one layer of adipocytes. The number and size of adipocytes is decreased in comparison to the fat pocket of the unexposed control as shown in FIG. 16.

FIGS. 16A and 16B depict the results of histological samples obtained from the non-exposed region of test site 11, obtained at the same time as the samples in FIGS. 15A and 15B. The dermis 1601 contains fat pockets 1602. No inflammation or tissue damage is present. A fine superficial septum 1603 separates different fat lobuli within the superficial fat layer 1604. The volume of fat, and number and size of individual adipocytes is increased in comparison to the treatment site shown in FIGS. 15A and 15B. The intradermal fat pocket 1602 contains up to 3 layers of adipocytes and is increased in volume, number and size of individual adipocytes in comparison to FIGS. 15A and 15B.

In summary, selective loss of subcutaneous fat can be maintained over time without scarring or cutaneous damage.

Example 4

Selective Loss of Subcutaneous Fat Over Time

A temperature plot depicting phase transitions during a course of treatment was generated using a miniature Yucatan pig. A cooling device comprising a copper plate perfused by a cooling agent tempered at −5° C. was placed in contact with an application site for about 600 seconds. For the purposes of this experiment, the temperature of the epidermis did not fall below 0° C.

Graph 1801 depicts a temperature plot as measured by a thermocouple located at the superficial fat layer just below the dermis. During the first 10 seconds, a temperature of about 36° C. is recorded, which is essentially the body temperature of the pig.

Graph 1802 depicts a temperature plot as measured by a thermocouple located at the interface between the cooling device and the epidermis. During the first 10 seconds, a temperature of about −3° C. is recorded, which is essentially the temperature of the cooling device when not in contact with the skin. Over the course of time when the cooling device has been in contact with the application site, the temperature initially rises as a result of heat flow from the skin to the device. During further contact with the cooling device, the temperature drops to a temperature above the cooling device when not in contact with the skin. Only after removal of the cooling device at the time mark around 360 seconds does the temperature drops below 0° C.

The temperature plot 1801, as measured by the subdermal thermocouple. decreased slowly over time. The slope of the temperature decrease changed at about 180 seconds from the start of treatment. The average temperature drop became slower over time, which is indicative of the phase change. Fluctuations were observed between about 180 seconds to about 300 seconds. The fluctuations could be due to movement of the thermocouple or alternatively, by oscillations in blood flow. Oscillations in blood flow during cooling (referred to as a "hunting phenomenon") are caused by periodic changes in activity of intraluminar smooth muscles of the vessel. Following removal of the device from the skin at 360 seconds, the skin did not continuously re-warm, but instead became level within a plateau at 15° C., which is also indicative of a phase transition.

Figure 19:
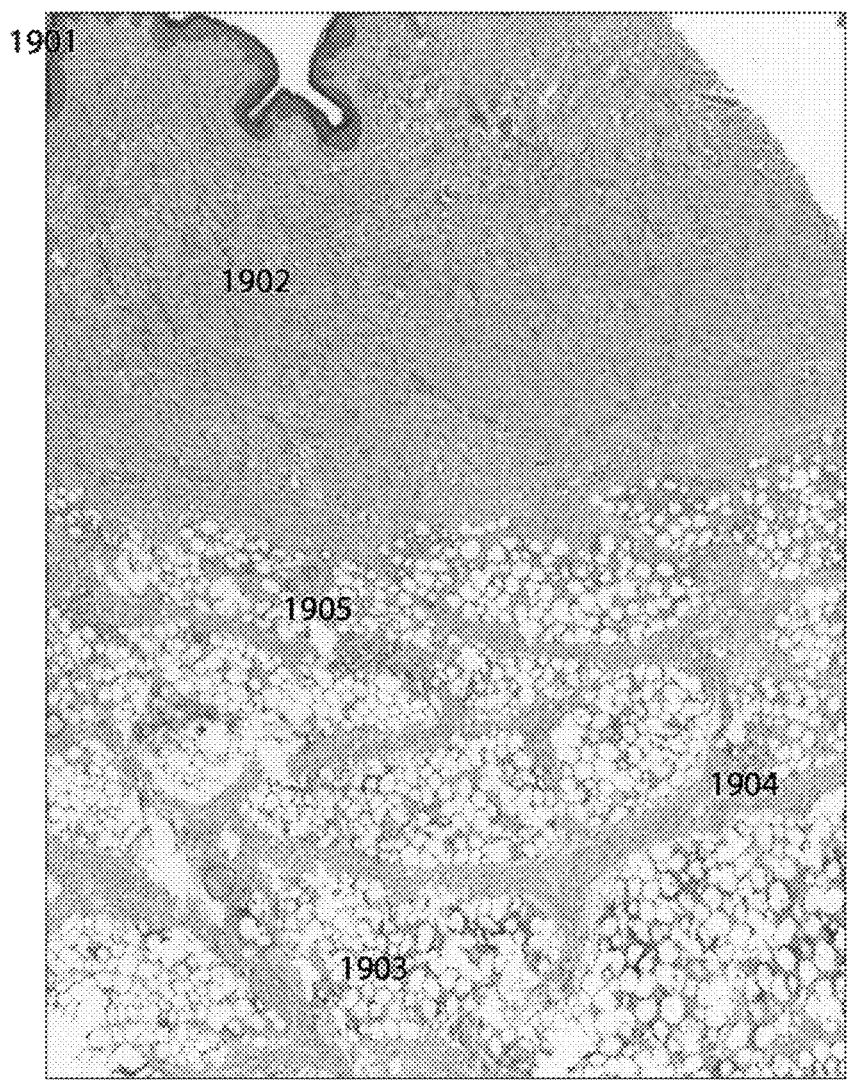
FIG. 19 depicts the results of histological analysis of samples obtained from the test site where the temperature plot of FIG. 18 was generated at 5 days post-treatment.

FIG. 19 depicts the histology of a sample obtained 5 days post-treatment from the test site from where the temperature plot was obtained. The epidermis 1901 and the dermis 1902 present as completely unchanged. Within the subcutaneous fatty tissue 1903, there is marked inflammation representing a lobular and septal panniculitis. The fat cells appear to be reduced in size as compared to non-cold exposed sites.

A number of embodiments of the invention have been described. Nevertheless, it will be understood that various modifications may be made without departing from the spirit and scope of the invention. Accordingly, other embodiments are within the scope of the following claims.

The invention claimed is:

1. A cooling method for selective disruption of lipid-rich cells in a non-infant human treatment subject comprising:
    applying at least one cooling element proximate to an application site of the treatment subject;
    utilizing the cooling element to decrease the temperature beneath the application site, wherein the temperature decrease is sufficient to disrupt and thereby reduce lipid-rich cells therein; and
    while the temperature is decreased, utilizing at least one feedback device to provide feedback information about at least one physiological parameter of the dermis or epidermis indicative of the absence of substantial crystal formation in one of the dermis or epidermis of the subject and sufficient to confirm that non-lipid-rich cells proximate to the cooling element are not disrupted, wherein the absence of substantial crystal formation is indicated by an electrical impedance of between about 10 k$\Omega$/mm to about 50 k$\Omega$/mm in one of the dermis or epidermis of the subject, thereby selectively disrupting lipid-rich cells in the subject.

2. The method of claim 1, wherein the temperature decrease creates a local temperature gradient through the dermis, epidermis and subcutaneous adipose tissue of the subject.

3. The method of claim 1, wherein the lipid-rich cells are adipocytes within subcutaneous adipose tissue.

4. The method of claim 1, wherein the cooling element contacts the application site.

* * * * *

UNITED STATES PATENT AND TRADEMARK OFFICE
CERTIFICATE OF CORRECTION

PATENT NO. : 11,590,020 B2
APPLICATION NO. : 14/493333
DATED : February 28, 2023
INVENTOR(S) : Richard R. Anderson et al.

It is certified that error appears in the above-identified patent and that said Letters Patent is hereby corrected as shown below:

In the Specification

Column 4, Line 64, "of or" consists" should be --of" or "consists--.

Signed and Sealed this
Eighteenth Day of April, 2023

*Katherine Kelly Vidal*

Katherine Kelly Vidal
*Director of the United States Patent and Trademark Office*